(12) United States Patent
Jung et al.

(10) Patent No.: US 8,648,105 B2
(45) Date of Patent: *Feb. 11, 2014

(54) DIARYLTHIOHYDANTOIN COMPOUNDS

(75) Inventors: Michael E. Jung, Los Angeles, CA (US); Dongwon Yoo, Los Angeles, CA (US); Charles L. Sawyers, New York, NY (US); Chris Tran, New York, NY (US); John Wongvipat, New York, NY (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/333,543

(22) Filed: Dec. 21, 2011

(65) Prior Publication Data

US 2012/0190718 A1  Jul. 26, 2012

Related U.S. Application Data

(63) Continuation of application No. 11/730,168, filed on Mar. 29, 2007, now Pat. No. 8,110,594.

(60) Provisional application No. 60/786,837, filed on Mar. 29, 2006.

(51) Int. Cl.
*A61K 31/4166* (2006.01)
*C07D 233/86* (2006.01)

(52) U.S. Cl.
USPC ............ 514/389; 548/301.4; 548/317.1

(58) Field of Classification Search
None
See application file for complete search history.

(56) References Cited

U.S. PATENT DOCUMENTS

| | | | |
|---|---|---|---|
| 3,823,240 A | 7/1974 | Sauli | |
| B379,038 I5 | 1/1975 | Magnani | |
| 3,923,994 A | 12/1975 | Magnani | |
| 3,984,430 A | 10/1976 | Curran | |
| 4,097,578 A | 6/1978 | Perronnet et al. | |
| 4,234,736 A | 11/1980 | Bernauer et al. | |
| 4,304,782 A | 12/1981 | Dumont et al. | |
| 4,312,881 A | 1/1982 | Wootton | |
| 4,399,216 A | 8/1983 | Axel et al. | |
| 4,407,814 A | 10/1983 | Bernauer et al. | |
| 4,427,438 A | 1/1984 | Nagano et al. | |
| 4,473,393 A | 9/1984 | Nagpal | |
| 4,482,739 A | 11/1984 | Bernauer et al. | |
| 4,559,157 A | 12/1985 | Smith et al. | |
| 4,608,392 A | 8/1986 | Jacquet et al. | |
| 4,636,505 A | 1/1987 | Tucker | |
| 4,749,403 A | 6/1988 | Liebl et al. | |
| 4,753,957 A | 6/1988 | Chan | |
| 4,820,508 A | 4/1989 | Wortzman | |
| 4,859,228 A | 8/1989 | Prisbylla | |
| 4,873,256 A | 10/1989 | Coussediere et al. | |
| 4,938,949 A | 7/1990 | Borch et al. | |
| 4,944,791 A | 7/1990 | Schroder et al. | |
| 4,992,478 A | 2/1991 | Geria | |
| 5,010,182 A | 4/1991 | Brake et al. | |
| 5,069,711 A | 12/1991 | Fischer et al. | |
| 5,071,773 A | 12/1991 | Evans et al. | |
| 5,084,472 A | 1/1992 | Moguilewsky et al. | |
| 5,166,358 A | 11/1992 | Seuron et al. | |
| 5,411,981 A | 5/1995 | Gaillard-Kelly et al. | |
| 5,434,176 A | 7/1995 | Claussner et al. | |
| 5,554,607 A | 9/1996 | Elokdah et al. | |
| 5,556,983 A | 9/1996 | Claussner et al. | |
| 5,589,497 A | 12/1996 | Claussner et al. | |
| 5,614,620 A | 3/1997 | Liao et al. | |
| 5,627,201 A | 5/1997 | Gaillard-Kelly et al. | |
| 5,646,172 A | 7/1997 | Claussner et al. | |
| 5,656,651 A | 8/1997 | Sovak et al. | |
| 5,705,654 A | 1/1998 | Claussner et al. | |
| 5,726,061 A | 3/1998 | Robbins et al. | |
| 5,750,553 A | 5/1998 | Claussner et al. | |
| 5,783,707 A | 7/1998 | Elokdah et al. | |
| RE35,956 E | 11/1998 | Gaillard-Kelly et al. | |
| 5,958,936 A | 9/1999 | Claussner et al. | |
| 5,985,868 A | 11/1999 | Gray | |
| 6,087,509 A | 7/2000 | Claussner et al. | |
| 6,107,488 A | 8/2000 | Bouchet et al. | |
| 6,172,076 B1 | 1/2001 | Embrey et al. | |
| 6,235,910 B1 | 5/2001 | Beller et al. | |
| 6,242,611 B1 | 6/2001 | Claussner et al. | |
| 6,307,030 B1 | 10/2001 | French et al. | |
| 6,350,763 B1 | 2/2002 | Kelly et al. | |
| 6,472,415 B1 | 10/2002 | Sovak et al. | |
| 6,479,063 B2 | 11/2002 | Weisman et al. | |
| 6,489,163 B1 | 12/2002 | Roy et al. | |
| 6,506,607 B1 | 1/2003 | Shyjan | |

(Continued)

FOREIGN PATENT DOCUMENTS

AU    217893    6/1958
CN    101032483 A    9/2007

(Continued)

OTHER PUBLICATIONS

Abrahamsson, P.-A., European Urology, 48:900 (2005).*
Patani, et al., Chem. Rev., 96:3147 (1996).*
Clegg, et al. Can. Res. 72:1494 (2012).*
Office Action EP 11178889.9 (Aug. 29, 2012).*
Office Action EP 12193684.3 (Jan. 22, 2013).*
Office Action NZ 601503 (Jul. 31, 2012).*
Office Action AU2007245022 (Nov. 12, 2012).*
Office Action U.S. Appl. No. 12/257,743 (Mar. 28, 2013).*
Office Action U.S. Appl. No. 13/448,964 (Feb. 28, 2013).*
Office Action U.S. Appl. No. 13/448,964 (Sep. 18, 2012).*
Park, et al., Annu. Rev. Pharmacol. Toxicol., 41:443 (2001).*
A Textbook of Drug Design and Development, P. Krogsgaard-Larson and H. Bundgaard, eds. Ch 5, pp. 113-191 (Harwood Academic Publishers, 1991).
A.M. Soto et al. Control of Cell Proliferation: Evidence for Negative Control on Estrogen-sensitive T47D Human Breast Cancer Cells:, Cancer Rsearch, 46, (1986), pp. 2271-2275.

(Continued)

*Primary Examiner* — Michael Barker
(74) *Attorney, Agent, or Firm* — Venable LLP; Michael A. Gollin; Lars H. Genieser

(57) ABSTRACT

The present invention relates to diarylthiohydantoin compounds and methods for synthesizing them and using them in the treatment of hormone refractory prostate cancer.

27 Claims, 25 Drawing Sheets

(56) References Cited

U.S. PATENT DOCUMENTS

| | | | |
|---|---|---|---|
| 6,518,257 B1 | 2/2003 | Tasaka et al. | |
| 6,828,471 B2 | 12/2004 | Sawyers et al. | |
| 6,949,521 B2 | 9/2005 | Chu et al. | |
| 7,138,421 B2 | 11/2006 | Cleve et al. | |
| 7,271,188 B2 | 9/2007 | Tachibana et al. | |
| 7,601,748 B2 | 10/2009 | Cleve et al. | |
| 7,709,517 B2 | 5/2010 | Sawyers et al. | |
| 7,718,684 B2 | 5/2010 | Jung et al. | |
| 8,110,594 B2 * | 2/2012 | Jung et al. | 514/391 |
| 8,183,274 B2 | 5/2012 | Sawyers et al. | |
| 2002/0133833 A1 | 9/2002 | Sawyers et al. | |
| 2003/0225138 A1 | 12/2003 | Sircar et al. | |
| 2004/0009969 A1 | 1/2004 | Cleve et al. | |
| 2004/0116417 A1 | 6/2004 | Boubia et al. | |
| 2005/0153968 A1 | 7/2005 | Bi et al. | |
| 2006/0127902 A1 | 6/2006 | Madden et al. | |
| 2007/0004753 A1 | 1/2007 | Sawyers et al. | |
| 2007/0166717 A1 | 7/2007 | Sawyer et al. | |
| 2007/0249697 A1 | 10/2007 | Tachibana et al. | |
| 2007/0254933 A1 | 11/2007 | Jung et al. | |
| 2008/0139634 A2 | 6/2008 | Jung et al. | |
| 2009/0111864 A1 | 4/2009 | Jung et al. | |
| 2010/0172975 A1 | 7/2010 | Sawyers et al. | |
| 2010/0210665 A1 | 8/2010 | Sawyers et al. | |
| 2011/0003839 A1 | 1/2011 | Jung et al. | |

FOREIGN PATENT DOCUMENTS

| | | |
|---|---|---|
| DE | 2102605 | 7/1971 |
| DE | 2126187 A1 | 12/1971 |
| DE | 2614831 A1 | 10/1977 |
| EP | 0 001 813 A1 | 5/1979 |
| EP | 0002259 A2 | 6/1979 |
| EP | 0017976 B1 | 10/1980 |
| EP | 0 091 596 A2 | 10/1983 |
| EP | 0144098 A1 | 6/1985 |
| EP | 0331232 A2 | 9/1989 |
| EP | 362179 A2 | 4/1990 |
| EP | 0 436 426 A1 | 7/1991 |
| EP | 0494819 A1 | 7/1992 |
| EP | 0572191 A1 | 12/1993 |
| EP | 0578516 A1 | 1/1994 |
| EP | 0580459 A1 | 1/1994 |
| EP | 0721944 A1 | 7/1996 |
| EP | 0770613 A1 | 5/1997 |
| EP | 1790640 A1 | 5/2007 |
| EP | 2400847 | 1/2012 |
| EP | 2400847 A1 * | 1/2012 |
| FR | 2 075 751 A5 | 10/1971 |
| FR | 2 329 276 A1 | 5/1977 |
| FR | 2693461 A1 | 1/1994 |
| FR | 2715402 A1 | 7/1995 |
| FR | 2845384 A1 | 4/2004 |
| JP | 48087030 U | 10/1973 |
| JP | 59210083 A | 11/1984 |
| JP | 1009978 A | 1/1989 |
| JP | 2019363 A | 1/1990 |
| JP | 6-073017 A | 3/1994 |
| JP | 19946073017 A * | 3/1994 |
| JP | 10-510845 A | 10/1998 |
| JP | 3845455 B2 | 11/2006 |
| JP | 2009-531449 A | 9/2009 |
| WO | WO-9013646 A1 | 11/1990 |
| WO | WO-9518794 A1 | 7/1995 |
| WO | WO-9700071 A1 | 1/1997 |
| WO | WO-9719064 A1 | 5/1997 |
| WO | WO-9719931 A1 | 6/1997 |
| WO | WO-0017163 A1 | 3/2000 |
| WO | WO-0026195 A1 | 5/2000 |
| WO | WO-0044731 A1 | 8/2000 |
| WO | WO-0107048 A1 | 2/2001 |
| WO | WO-0192253 A2 | 12/2001 |
| WO | WO-0194346 A1 | 12/2001 |
| WO | WO-0242488 A1 | 5/2002 |
| WO | WO-02053155 A1 | 7/2002 |
| WO | WO-02081453 A1 | 10/2002 |
| WO | WO-03029245 A1 | 4/2003 |
| WO | WO-03032994 A2 | 4/2003 |
| WO | WO-03057220 A1 | 7/2003 |
| WO | WO-03093243 A1 | 11/2003 |
| WO | WO-03096980 A2 | 11/2003 |
| WO | WO-2004022572 A1 | 3/2004 |
| WO | WO-2004031160 A2 | 4/2004 |
| WO | WO-2004070050 A2 | 8/2004 |
| WO | WO-2004111031 A1 | 12/2004 |
| WO | WO-2005042488 A1 | 5/2005 |
| WO | WO-2005059109 A2 | 6/2005 |
| WO | WO-2005060661 A2 | 7/2005 |
| WO | WO-2005089752 A2 | 9/2005 |
| WO | WO-2005099693 A2 | 10/2005 |
| WO | WO-2006010642 A1 | 2/2006 |
| WO | WO-2006028226 A1 | 3/2006 |
| WO | WO-2006124118 A1 | 11/2006 |
| WO | WO 2006124118 A1 * | 11/2006 |
| WO | WO-2007045877 A1 | 4/2007 |
| WO | WO-2007126765 A2 | 11/2007 |
| WO | WO-2007127010 A2 | 11/2007 |
| WO | WO-2008119015 A2 | 10/2008 |
| WO | WO-2009055053 A2 | 4/2009 |
| WO | WO-2009076408 A2 | 6/2009 |
| WO | WO-2010/099238 A1 | 9/2010 |
| WO | WO 2010099238 A1 * | 9/2010 |

OTHER PUBLICATIONS

Abstract submitted by Samedy Ouk, Prostate Cancer Foundation Scientific Retreat, Scottsdale, Arizona, Sep. 29-Oct. 1, 2005.

Aly et al., "Functionality of amidines and amidrazones," ARKIVOC (i), pp. 153-194 (2008).

Ametamey et al., "Reaktionen von 3-(Dimethylamino)-2H-azirinen mit 1,3-Benzoxazol-2(3H)-thion," Helvetica Chima Acta, vol. 73, No. 3, pp. 599-607 & title page (1990).

Ausubel et al., Current Protocols in Molecular Biology, Wiley Interscience Publishers, (1995).

Baek, S.H. et al. Exchange of N-CoR corepressor and Tip60 coactivator complexes links gene expression by NF-kappaB and beta-amyloid precursor protein. Cell 110, 55-67 (2002).

Balk, S.P. Androgen receptor as a target in androgen-independent prostate cancer. Urology 60, 132-8; discussion 138-9 (2002).

Batch, J.A., et al., "Androgen receptor gene mutations identified by SSCP in fourteen subjects with androgen insensitivity syndrome", Hum. Mol. Genet. 1 (7), 497-503 (1992).

Bohl et al., "Structural basis for antagonism and resistance of bicalutamide in prostate cancer", Proc. Nat. Acad. Sci., 2005, v. 102(17), pp. 6201-6206.

Brockschmidt, F.F., et al., "The two most common alleles of the coding GGN repeat in the androgen receptor gene cause differences in protein function", J. Mol. Endocrinol. 39 (1), 1-8 (2007).

Burnstein et al. Androgen Glucocorticoid Regulation of Androgen Receptor cDNA Expression. Molecular and Cellular Endocrinology. 1995. v. 115, pp. 177-186.

Cai, C., et al., "c-Jun has multiple enhancing activities in the novel cross talk between the androgen receptor and Ets variant gene 1 in prostate cancer", Mol. Cancer Res. 5 (7), 725-735 (2007).

Chang et al., Science 240 (4850), 324-326 (1988).

Chemical Abstracts Search provided with Oct. 8, 2010 Office Action in U.S. Appl. No. 11/730,168.

Chemical Abstracts, vol. 114, p. 185368 (May 13, 1991).

Chen, C.D. et al., "Molecular determinants of resistance to antiandrogen therapy", Nature Medicine, vol. 10, No. 1 (Jan. 2004) pp. 33-39.

Cinar et al. Androgen Receptor Mediates the Reduced Tumor Growth, Enhanced Androgen Responsiveness, and Selected Target Gene Transactivation in Human Prostate Cancer Cell Line. Cancer Research. 2001. v. 61. pp. 7310-7317.

Corrected Notice of Allowability issued in U.S. Appl. No. 11/730,168 mailed Jan. 19, 2012.

Corrected Notice of Allowability issued in U.S. Appl. No. 11/730,168 mailed Dec. 22, 2011.

(56) References Cited

OTHER PUBLICATIONS

Cousty-Berlin, et al., "Preliminary Pharmacokinetics and Metabolism of Novel Non-steroidal Antiandrogens in the Rat: Relation of their Systemic Activity to the Formation of a Common Metabolite," *J. Steroid Biochem. Molec. Biol.*, vol. 51, No. 1/2, pp. 47-55 (1994).
Craft, N. et al. Evidence for clonal outgrowth of androgen-independent prostate cancer cells from androgen-dependent tumors through a two-step process. Cancer Res 59,5030-6 (1999).
Craft, N., Shostak, Y., Carey, M. & Sawyers, C.L. A mechanism for hormone-independent prostate cancer through modulation of androgen receptor signaling by the HER-2/neu tyrosine kinase. Nat Med 5, 280-5 (1999).
Creaven, P.J. et al., "Pharmacokinetics and Metabolism of Nilutamide", Supp. Urology, vol. 37, No. 2 (Feb. 1991) pp. 13-19.
Crooks et al., "The Structure of Some Reaction Products of 2,3-Dihydrophenalene-1,2,3-Trione with Urea and its Homologues," Gazzetta Chimica Italiana, vol. 107, No. 5-6, pp. 353-354 & title page (1977).
Data Sheet from U.S. Patent and Trademark Office (USPTO) for U.S. Appl. No. 08/807,760, (1998).
Database CA Chemical Abstracts Service, Columbus, Ohio, US; Jan. 1, 1994. Dhal, P. N. et al. Synthesis of thiohydantoins, thiazolidones, and their derivatives from N1-(4'-arylthiazol-2'-yl)thioureas. J Ind Chem Soc. 50:680-684. 1973.
DePrimo, S.E. et al. Transcriptional programs activated by exposure of human prostate cancer cells to androgen. Genome Biol 3, RESEARCH0032 (2002).
Design of Prodrugs, edited by H. Bundgaard, (Elsevier, 1985).
Dhal et al., "Synthesis of Thiohydantoins, Thiazolidones and Their Derivatives from N-(4'-Aryl Thiazole 2'-YL) Thioureas," J. Indian Chem. Soc., vol. L, pp. 680-684 (Oct. 1973).
Dyer et al., "Preparation of Polyhydrouracils and Polyiminoimidazolidinones," Journal of Polymer Science, Part A-1, vol. 7, pp. 833-849 & title page (1969).
Edwards, J., Krishna, N.S., Grigor, K.M. & Bartlett, J.M. Androgen receptor gene amplification and protein expression in hormone refractory prostate cancer. Br J Cancer 89, 552-6 (2003).
Ellis, W.J. et al. Characterization of a novel androgen-sensitive, prostate-specific antigen-producing prostatic carcinoma xenograft: LuCaP 23. Clin Cancer Res 2, 1039-48 (1996).
Ellwood-Yen, K. et al. Myc-driven murine prostate cancer shares molecular features with human prostate tumors. Cancer Cell 4, 223-38 (2003).
Elokdah Hassan et al. Design, synthesis, and biological evaluation of thio-containing compounds with serum HDL-cholesterol-elevating properties. J Med Chem. 47(29): 681-695, (2004).
Espada et al.,"N$_3$-Arylspiroimidazolidine-2,4-Diones, N$_3$-Arylspiroimidazolidine-2-Thio-4-ones and 4-Hydroxy Derivatives. Synthesis and Anthelminitic Activity," IL Farmaco, vol. 45, No. 11, pp. 1237-1243 & title page (1990).
European Search Report dated Jul. 20, 2011 for European Application No. 07754060.7, 7 pages.
European Search Report issued in counterpart application, EP80102042 (1981).
European Search Report issued in counterpart application, EP78101244.8 (1979).
European Search Report issued in counterpart Euopean application No. 90403725.6, 1991.
Extended European Search Report issued in European Patent Application No. EP 06748863.5, mailed on Feb. 12, 2009.
Extended European Search Report dated Aug. 8, 2011 (search completed Jul. 12, 2011) for European Application No. 11163948.0, 10 pages.
Feher, et al., "BHB: A Simple Knowledge-Based Scoring Function to Improve the Efficiency of Database Screening," *J. Chem. Inf. Comput. Sci.*, vol. 43, pp. 1316-1327 (2003).
Feldman, B.J. & Feldman, D. The development of androgen-independent prostate cancer. Nat Rev Cancer 1, 34-45 (2001).
Final Office Action in U.S. Appl. No. 12/708,523 mailed on May 5, 2011.
Font de Mora, J. & Brown, M. AIB1 is a conduit for kinase-mediated growth factor signaling to the estrogen receptor. Mol Cell Biol 20, 5041-7 (2000).
Foury, et al., "Control of the Proliferation of Prostate Cancer Cells by an Androgen and Two Antiandrogens. Cell Specific Sets of Responses," *J. Steroid Biochem. Molec. Biol.*, vol. 66, No. 4, pp. 235-240 (1998).
Gelmann, E.P. Molecular biology of the androgen receptor. J Clin Oncol 20, 3001-15 (2002).
Gioeli, D. et al. Androgen receptor phosphorylation. Regulation and identification of the phosphorylation sites. J Biol Chem 277, 29304-14 (2002).
Glass, C.K. & Rosenfeld, M.G. The coregulator exchange in transcriptional functions of nuclear receptors. Genes Dev 14, 121-41 (2000).
Goubet, et al., Conversion of a Thiohydantoin to he Corresponding Hydantoin via a Ring-Opening/Ring Closure Mechanism, *Tetrahedron Letters*, vol. 37, No. 43, pp. 7727-7730 (1996).
Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).
Graham and van der Eb, "A new technique for the assay of infectivity of human adenovirus 5 DNA", Virology, v. 52(2) (Apr. 1973) pp. 456-467.
Gregory, C.W. et al. A mechanism for androgen receptor-mediated prostate cancer recurrence after androgen deprivation therapy. Cancer Res 61, 4315-9 (2001).
Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8. (2001).
Günzl et al., "Zur Chemie der vicinalen Triketone, XIII, Versuche zur Darstellung von *Schiff*schen Basen aus cyclischen, vicinalen Triketonen," Monatshefte für Chemie, vol. 113, No. 11, pp. 1299-1310 & title page (1982).
Hamilton-Reeves, J.M., et al, "Isoflavone-rich soy protein isolate suppresses androgen receptor expression without altering estrogen receptor-beta expression or serum hormonal profiles in men at high risk of prostate cancer", J. Nutr. 137 (7), 1769-1775 (2007).
Holzbeierlein, J. et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.
Homma,S., et al., "Differential levels of human leukocyte antigen-class I, multidrug-resistance 1 and androgen receptor expressions in untreated prostate cancer cells: the robustness of prostate cancer", Oncol. Rep. 18 (2), 343-346 (2007).
Horig et al. From bench to clinic and back: Perspective on 1$^{st}$ IQPC Translational Research Conference. 2004. Journal of Translational Medicine. 2:44.
Horoszewicz, J.S. et al. LNCaP model of human prostatic carcinoma. Cancer Res 43, 1809-18 (1983).
Hough, "Synthesis of Imidazolin-2-ones by Rearrangement of N-Carbamoyliminium Salts Derived From 4-Hydroxyimidazolidin-2-ones," Journal of Heterocyclic Chemistry, vol. 26, No. 6, pp. 1523-1525 & title page (1989).
Huang, Z.Q., Li, J. & Wong, J. AR possess an intrinsic hormone-independent transcriptional activity. Mol Endocrinol 16, 924-37 (2002).
International Search Report issued in International Application No. PCT/US2007/007854, mailed on Apr. 15, 2008.
International Search Report issued in International Application No. PCT/US2008/012149 mailed on Apr. 29, 2009.
International Search Report issued in PCT Application No. PCT/US06/11417 dated Jul. 3, 2006.
International Search Report issued in PCT Application No. PCT/US2003/015375, mailed Dec. 3, 2003.
International Search Report issued in PCT Application PCT/US2004/042221, mailed on Jun. 20, 2005.
International Search Report issued in PCT Application PCT/US2005/005529, mailed on Nov. 10, 2005.

(56) References Cited

OTHER PUBLICATIONS

International Search Report issued in PCT Application PCT/US2007/07485, mailed on Sep. 4, 2008.
International Search Report issued in PCT Application PCT/US96/10286, (1996).
Jones, Genetics, 85: 23 (1977).
Jung et al. Structure—Activity Relationship for Thiohydantoin Androgen Receptor Antagonists for Castration-Resistant Prostate Cancer (CRPC). 2010. J Med Chem. 53:2779-2796.
Karp et al., "Prostate Cancer Prevention: Investigational Approaches and Opportunities", Cancer Res., v. 56 (Dec. 15, 1996) pp. 5547-5556.
Karvonen, et al., "Interaction of Androgen Receptors with Androgen Response Element in Intact Cells," *The Journal of Biological Chemistry*, vol. 272, No. 25, pp. 15973-15979 (1997).
Kato, S. et al. Activation of the estrogen receptor through phosphorylation by mitogen-activated protein kinase. Science 270, 1491-4 (1995).
Kemppainen, et al., "Distinguishing Androgen Receptor Agonists and Antagonists: Distinct Mechanisms of Activation by Medroxyprogesterone Acetate and Dihydrotestosterone," *Mol. Endocrinol.*, vol. 13, pp. 440-454 (1999); mend.endojournals.org.
Keown et al., Methods in Enzymology, 185:527-537 (1990).
Kingsman et al., Gene, 7: 141 (1979).
Kinoshita, H. et al. Methylation of the androgen receptor minimal promoter silences transcription in human prostate cancer. Cancer Res 60, 3623-30 (2000).
Klein, K.A. et al. Progression of metastatic human prostate cancer to androgen independence in immunodeficient SCID mice. Nat Med 3, 402-8 (1997).
Kousteni, S. et al. Nongenotropic, sex-nonspecific signaling through the estrogen or androgen receptors: dissociation from transcriptional activity. Cell 104, 719-30 (2001).
Krüger et al., "Synthese and Reaktionen von 1-(1-Cyanoalkyl)-1-hydroxyharnstoffen," Arch. Pharm. (Weinheim), vol. 311, pp. 39-47 (1978).
Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).
Li, P. et al. Heterogeneous expression and functions of androgen receptor co-factors in primary prostate cancer. Am J Pathol 161, 1467-74 (2002).
Linja, M.J. et al., "Amplification and overexpression of androgen receptor gene in hormone-refractory prostate cancer", Cancer Research, vol. 61 (May 1, 2001) pp. 3550-3555.
Lobaccaro, J.M. et al. Molecular modeling and in vitro investigations of the human androgen receptor DNA-binding domain: application for the study of two mutations. Mol Cell Endocrinol 116, 137-47 (1996).
Lu et al. "Molecular Mechanisms of Androgen-Independent Growth of Human Prostate Cancer LNCaP-AI Cells", Endocrinology 1999, vol. 140, No. 11, pp. 5054-5059.
Mammalian Cell Biotechnology: a Practical Approach, M. Butler, ed. (IRL Press, 1991).
Mancheva et al., "Preparation and Characterization of Diphenylindenonylthiohydantoin Derivatives of Non-Protein Cycloaliphatic Amino Acids," Dokladi na Bulgarskata Akademiya na Naukite (Comptes rendu de l'Academie bulgare des Sciences),vol. 45, No. 11, pp. 67-70 & title page (1992).
Manolagas, S.C., Kousteni, S. & Jilka, R.L. Sex steroids and bone. Recent Prog Horm Res 57, 385-409 (2002).
Mansour et al., Nature, 336:348-352 (1988).
Marhefka, et al., "Homology Modeling Using Multiple Molecular Dynamics Simulations and Docking Sudies of the Human Androgen Receptor Ligand Binding Domain Bound to Testosterone and Nonsteroidal Ligands," *J. Med. Chem.*, vol. 44, No. 11, pp. 1729-1740 (2001).
Masiello, D., Cheng, S., Bubley, G.J., Lu, M.L. & Balk, S.P. Bicalutamide functions as an androgen receptor antagonist by assembly of a transcriptionally inactive receptor. J Biol Chem 277, 26321-6 (2002).
Matias, et al., "Local Inhibition of Sebaceous Gland Growth by Topically Applied RU 58841,"*NY Acad. Sci.*, vol. 761, pp. 56-65 (1995).
Matias, P.M. et al. Structural basis for the glucocorticoid response in a mutant human androgen receptor (AR(ccr)) derived from an androgen-independent prostate cancer. J Med Chem 45, 1439-46 (2002).
Matias, P.M. et al. Structural evidence for ligand specificity in the binding domain of the human androgen receptor. Implications for pathogenic gene mutations. J Biol Chem 275, 26164-71 (2000).
McDonnell, T.J. et al. Expression of the protooncogene bcl-2 in the prostate and its association with emergence of androgen-independent prostate cancer. Cancer Res 52, 6940-4 (1992).
Migliaccio, A. et al. Steroid-induced androgen receptor-oestradiol receptor beta-Src complex triggers prostate cancer cell proliferation. Embo J 19, 5406-17 (2000).
Muller et al., 1991, Mol. & Cell. Bio. 11:1785.
N. Nakajima et al., Tetrahedron, v.58 (2002) pp. 3561-3577.
Nakajima et al. Activated Dimethyl sulfoxide dehydration of amide and its application to one-pot preparation of benzyl-type prefluoroimidates. 2002. Tetrahedron. 58:3561-3577.
Nam et al., "*Action of the Src Family Kinase Inhibitor, Dasatinib (BMS-354825), on Human Prostate Cancer Cells*", Cancer Res., 2005, v. 65(20), pp. 9185-9189.
Navone, N. M., et al., "Model Systems of Prostate Cancer: Uses and Limitations" Cancer Metastasis, Kluwer Academic Publishers, Dordrecht, NL, 17 (4), 1999, pp. 361-371.
Nicole et al., "Synthèses D'Acides Aminés Cycliques À Partir de Dérivés de L'Acide Adipique," Canadian Journal of Chemistry, vol. 40, pp. 353-366 (1962).
NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251, printed Oct. 24, 2007.
Norris, J.D. et al. Peptide antagonists of the human estrogen receptor. Science 285, 744-6 (1999).
Notice of Allowance issued in U.S. Appl. No. 11/730,168 mailed Sep. 20, 2011.
Notice of Allowance issued in U.S. Appl. No. 11/730,168 dated Jun. 10, 2011.
Notice of Allowance issued in U.S. Appl. No. 12/294,881 mailed Jun. 25, 2012.
Notice of Allowance issued in U.S. Appl. No. 12/708,531 mailed May 25, 2012.
Notice of Allowance with Examiner's Amendment in U.S. Appl. No. 10/583,280 mailed Jun. 9, 2011.
Notice of Allowance with Examiner's Amendment in U.S. Appl. No. 11/433,829 mailed Jun. 8, 2009.
Notice of Allowance with Examiner's Amendment in U.S. Appl. No. 11/433,829 mailed Nov. 18, 2009.
Notice of Allowance with Examiner's Amendment in U.S. Appl. No. 11/433,829 mailed Nov. 18, 2011.
Notice of Allowance, issued in U.S. Appl. No. 12/708,523, dated Dec. 16, 2011.
Notice of Allowance, issued in U.S. Appl. No. 12/708,523, dated Mar. 26, 2012.
Notice of References Cited from U.S. Patent and Trademark Office (USPTO) for U.S. Appl. No. 08/807,760, (1997).
Notice of References Cited of Jul. 24, 1992 from U.S. Patent and Trademark Office for U.S. Appl. No. 07/819,110.
Office Action (paper No. 10) from U.S. Patent and Trademark Office (USPTO) for U.S. Appl. No. 08/064,257 (mailed Sep. 27, 1994).
Office Action (paper No. 10) from U.S. Patent and Trademark Office for U.S. Appl. No. 08/064,257 (mailed Jan. 18, 1994).
Office Action (paper No. 7) from U.S. Patent and Trademark Office (USPTO) for U.S. Appl. No. 08/064,257 (mailed Aug. 31, 1994).
Office Action in U.S. Appl. No. 10/583,280 mailed on Apr. 2, 2010.
Office Action in U.S. Appl. No. 10/583,280 mailed on Nov. 29, 2010.
Office Action in U.S. Appl. No. 12/257,743 mailed on Nov. 20, 2009.

(56) References Cited

OTHER PUBLICATIONS

Office Action in U.S. Appl. No. 12/708,523, mailed on Oct. 1, 2010.
Office Action issued in U.S. Appl. No. 10/590,445, mailed on Mar. 2, 2009.
Office Action issued in U.S. Appl. No. 11/433,829 mailed on Jan. 27, 2009.
Office Action issued in U.S. Appl. No. 12/708,531 mailed Nov. 14, 2011.
Office Action mailed Oct. 1, 2010 in U.S. Appl. No. 12/708,523.
Office Action mailed Oct. 8, 2010 in U.S. Appl. No. 11/730,168.
Office Action of Nov. 14, 2011 from U.S. Pat. & Trademark Office for U.S. Appl. No. 12/708,531.
Office Action of Feb. 22, 1993 from U.S. Patent and Trademark Office for U.S. Appl. No. 07/819,110.
Office Action of Jun. 1, 1994 from U.S. Patent and Trademark Office for U.S. Appl. No. 07/819,110.
Office Action of Jun. 29, 2010 from U.S. Patent and Trademark Office for U.S. Appl. No. 12/257,743.
Office Action of Jul. 23, 2008 from U.S. Patent and Trademark Office for U.S. Appl. No. 10/590,445.
Office Action of Aug. 11, 2009 from U.S. Patent and Trademark Office for U.S. Appl. No. 10/583,280.
Office Action of Aug. 14, 1992 from U.S. Patent and Trademark Office for U.S. Appl. No. 07/819,110.
Office Action of Sep. 2, 1993 from U.S. Patent and Trademark Office for U.S. Appl. No. 07/819,110.
Oldfield et al., "The Chemistry and Pharmacology of a Ser4ies of Cycloalkanespiro-5'-hydantoins," Journal of Medical Chemistry, vol. 8, No. 2, pp. 239-249 (1965).
Ouk, S. et al., "Development of Androgen Receptor Inhibitors for Hormone-refractory Prostate Cancer", Prostate Cancer Foundation Meeting, Scottsdale, AZ, Sep. 29-Oct. 1, 2005.
Perou, C.M. et al. Molecular portraits of human breast tumors. Nature 406, 747-52 (2000).
Presentation of Charles Sawyers, Prostate Cancer Foundation Scientific Retreat, Scottsdale, Arizona, Sep. 29-Oct. 1, 2005.; C141.
Raffo et al. Overexpression of bcl-2 Protects Prostate Cancer Cells from Apoptosis in Vitro and Confers Resistance to Androgen Depletion in Vivo. Cencer Research. 1995. v. 55. 4438-4445.
Rao et al., "Merits and Considerations in the Use of Anti-Androgen," J. Steroid Biochem. 31 (4B), pp. 731-737 (1988).
Raynaud, J Steroid Biochem, 11 (1979) 93-99.
Remington: The Science and Practice of Pharmacy, 19th Edition, Gennaro (ed.) 1995, Mack Publishing Company, Easton, PA.
Restriction Requirement in U.S. Appl. No. 10/583,280 mailed on Aug. 11, 2009.
Restriction Requirement in U.S. Appl. No. 10/590,445 mailed on Jun. 5, 2008.
Restriction Requirement in U.S. Appl. No. 10/590,445 mailed on Mar. 26, 2008.
Restriction Requirement in U.S. Appl. No. 11/433,829 mailed on Nov. 3, 2008.
Restriction Requirement in U.S. Appl. No. 12/257,743 mailed on Jul. 6, 2009.
Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).
Sambrook et al., Molecular Cloning: A Laboratory Manual 2nd edition (1989) Cold Spring Harbor Laboratory Press, Cold Spring Harbor, N.Y.
Saunders, P.T., et al., "Point mutations detected in the androgen receptor gene of three men with partial androgen insensitivity syndrome", Clin. Endocrinol. (Oxf) 37 (3), 214-220 (1992).
Schaefer et al., Drug Discovery Today, 13:913-916 (2008).
Schafer et al. Failure is an Option: ; learning from Unsuccessful Proof-of-Concept trials. 2008. Drug Discovery Today. 13:913-916.
Schellhammer, P.F. et al. Prostate specific antigen decreases after withdrawal of antiandrogen therapy with bicalutamide or flutamide in patients receiving combined androgen blockade. J Urol 157, 1731-5 (1997).
Scher et al. Antitumour activity of MDV3100 in castration-resistant prostate cancer: a phase 1-2 study. 2010. Lancet. 375:1437-1446.
Sderholm, et al., "Three-Dimensional Structure—Activity Relationships of Nonsteroidal Ligands in Complex with Androgen Receptor Ligand-Binding Domain," J. Med. Chem., vol. 48, No. 4, pp. 917-925 (2005).
Shang, Y. & Brown, M. Molecular determinants for the tissue specificity of SERMs. Science 295, 2465-8 (2002).
Shang, Y., Myers, M. & Brown, M. Formation of the androgen receptor transcription complex. Mol Cell 9, 601-10 (2002).
Shi, Xu-Bao, et al., "Functional analysis of 44 mutant androgen receptors from human prostate cancer", Cancer Research 62 (5), pp. 1496-1502 (Mar. 1, 2002).
Shiau, A.K. et al. The structural basis of estrogen receptor/coactivator recognition and the antagonism of this interaction by tamoxifen. Cell 95, 927-37 (1998).
Singh et al., "*Androgen Receptor Antagonists (Antiandrogens): Structure-Activity Relationships*", Current Medicinal Chemistry, 2000, 7, pp. 211-247.
Singh, "Amidine: Structure, Reactivity and Complexation Behaviour," Int'l J.of Chem. Tech. Res., vol. 1(2), pp. 250-264 (2009).
Sperry, et al., Androgen binding profiles of two distinct nuclear androgen receptors in Atlantic croaker (*Micropogonias undulates*), Journal of Steroid Biochemistry & Molecular Biology, vol. 73, pp. 93-103 (2000).
Stinchcomb et al., Nature, 282:39 (1979).
Su,Q.R., et al., "Polymorphisms of androgen receptor gene in childhood and adolescent males with first-onset major depressive disorder and associationwith related symptomatology", Int. J. Neurosci. 117 (7), 903-917 (2007).
Supplementary European Search in EP 07754060 mailed on Oct. 11, 2010.
Sweet,C.R., et al., "A unique point mutation in the androgen receptor gene in a family with complete androgen insensitivity syndrome", Fertil. Steril. 58 (4), 703-707 (1992).
Szelei et al. Androgen-Induced Inhibition of Proliferation in Human Breast Cancer MCF7 Cells Transfected with Androgen Receptor. Endocrinology. 1997. v. 138 (4). pp. 1406-1412.
Taplin, M.E. et al. Androgen receptor mutations in androgen-independent prostate cancer: Cancer and Leukemia Group B Study 9663. J Clin Oncol 21, 2673-8 (2003).
Taplin, M.E. et al. Mutation of the androgen-receptor gene in metastatic androgen-independent prostate cancer. N Engl J Med 332, 1393-8 (1995).
Taplin, M.E. et al. Selection for androgen receptor mutations in prostate cancers treated with androgen antagonist. Cancer Res 59, 2511-5 (1999).
Teutsch, G.; Goubet, F.; Battmann, T.; Bonfils, A.; Bouchoux, F.; Cerede, E.; Gofflo, D.; Gaillard-Kelly, M.; Philibert. D. ..J. Steroid Biochem. Molec. Biol. 1994, 48, 111-119.
*The Pharmacological Basis of Therapeutics*, Goodman and Gilman, eds., Macmillan Publishing Co., New York, 1980.
The Practice of Medicinal Chemistry, Camille G. Wermuth et al., Ch 31, (Academic Press, 1996).
Tremblay, A., Tremblay, G.B., Labrie, F. & Giguere, V. Ligand-independent recruitment of SRC-1 to estrogen receptor beta through phosphorylation of activation function AF-1. Mol Cell 3, 513-9 (1999).
Tschumper et al., Gene, 10: 157 (1980).
Umezawa et al., "The Synthesis of Cyclic α-Amino Acids," Bulletin of the Chemical Society of Japan, vol. 40, No. 1, pp. 209-214 & title page (1967).
Urlaub et al., Proc. Natl. Acad. Sci. USA, 77:4216 (1980).
Van Dort, M. E.; Robins, D. M.; Wayburn, B. J. Med. Chem. 2000, 43, 3344-3347.
Veldscholte, J. et al. A mutation in the ligand binding domain of the androgen receptor of human LNCaP cells affects steroid binding

(56) References Cited

OTHER PUBLICATIONS characteristics and response to anti-androgens. Biochem Biophys Res Commun 173, 534-40 (1990).

Visakorpi, T. et al. In vivo amplification of the androgen receptor gene and progression of human prostate cancer. Nat Genet 9, 401-6 (1995).

Wainstein, M.A. et al. CWR22: androgen-dependent xenograft model derived from a primary human prostatic carcinoma. Cancer Res 54, 6049-52 (1994).

Wallen et al., "Androgen Receptor Gene Mutations in Hormone-Refractory Prostate Cancer", J. Pathology 1999, vol. 189, pp. 559-563.

Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).

Wang, S. et al. Prostate-specific deletion of the murine Pten tumor suppressor gene leads to metastatic prostate cancer. Cancer Cell 4, 209-21 (2003).

Wooster,R., et al., "A germline mutation in the androgen receptor gene in two brothers with breast cancer and Reifenstein syndrome", Nat. Genet. 2 (2), 132-134 (1992).

Written Opinion issued in International Application No. PCT/US2007/007854, mailed on Apr. 15, 2008.

Written Opinion issued in International Application No. PCT/US2008/012149, mailed on Apr. 29, 2009.

Written Opinion issued in PCT Application No. PCT/US2004/042221, mailed on Jun. 20, 2005.

Written Opinion issued in PCT Application No. PCT/US2005/005529, mailed on Nov. 10, 2005.

Written Opinion issued in PCT Application No. PCT/US2006/011417, mailed on Jul. 3, 2006.

Written Opinion issued in PCT Application PCT/US2007/07485, mailed on Sep. 4, 2008.

Zajchowski et al. Estrogen inhibits the growth of estrogen receptor-negative, but not estrogen receptor-positive, human mammary epithelial cells expressing a recombinant estrogen receptor. 1993. Cancer Research. 53:5004-5011.

Zarghami, et al., "Steroid hormone regulation of prostate-specific antigen gene expression in breast cancer," *British Journal of Cancer*, vol. 75, No. 4, pp. 579-588 (1997).

Zhau, H.Y. et al. Androgen-repressed phenotype in human prostate cancer. Proc Natl Acad Sci U S A 93,15152-7 (1996).

Zhou, Z.X., Sar, M., Simental, J.A., Lane, M.V. & Wilson, E.M. A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).

Zoppi,S., et al. "Amino acid substitutions in the DNA-binding domain of the human androgen receptor are a frequent cause of receptor-binding positive androgen resistance", Mol. Endocrinol. 6 (3), 409-415 (1992).

Statement by Applicant of Jan. 15, 2013 (incorporated into filed IDS Transmittal Letter).

Clegg et al., "ARN-509: A Novel Antiandrogen for Prostate Cancer Treatment," *Cancer Res*. 2012; 72:1494-1503.

European Office Action issued in European Application No. 11 178 889.9 dated Aug. 29, 2012.

European Search Report issued in Application No. 12193684.3 dated Jan. 22, 2013.

Examination Report issued in New Zealand Application No. 601503 dated Jul. 31, 2012.

Examination Report issued in Australian Application No. 2007245022 dated Nov. 12, 2012.

Notice of Allowance issued in U.S. Appl. No. 12/257,743 dated Mar. 28, 2013.

Notice of Allowance issued in U.S. Appl. No. 13/448,964 dated May 31, 2013.

Office Action from the U.S. Patent & Trademark Office issued in U.S. Appl. No. 13/448,964 dated Feb. 28, 2013.

Office Action from the US Patent and Trademark Office (USPTO) issued in U.S. Appl. No. 13/448,964 dated Sep. 18, 2012.

Park et al., "Metabolism of Fluorine-Containing Drugs," Annu. Rev. Pharmacol. Toxicol. 2001, vol. 41, pp. 443-70.

Patani et al., "Bioisosterism: A Rational Approach in Drug Design," Chem. Rev. 1996, vol. 96, pp. 3147-3176.

Paul et al., "Antiandrogen Withdrawal Syndrome Associated with Prostate Cancer Therapies: Incidence and Clinical Significance," Drug Safety, 2000 (5): 381-390.

Office Action issued in U.S. Appl. No. 13/619,280 dated Oct. 28, 2013.

* cited by examiner

DIARYLTHIOHYDANTOIN COMPOUNDS

FIELD OF THE INVENTION

The present invention relates to diarylhydantoin compounds including diarylthiohydantoins, and methods for synthesizing them and using them in the treatment of hormone refractory prostate cancer. This application is a continuation of U.S. application Ser. No. 11/730,168 filed Mar. 29, 2007, which claims the benefit of U.S. Provisional Application No. 60/786,837, filed Mar. 29, 2006, the specifications of which are hereby incorporated by reference in their entirety. This application hereby incorporates by reference international application number PCT/US2006/011417 by the same assignee in its entirety.

This invention was made with Government support under Grant No. W81XWH-04-1-0129, awarded by the U.S. Army, Medical Research and Materiel Command and Grant No. CA092131, awarded by the National Institutes of Health. The Government has certain rights in this invention.

BACKGROUND OF THE INVENTION

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, therefore, reducing the AR activity. Although initially effective, these treatments quickly fail and the cancer becomes hormone refractory.

Recently, overexpression of AR has been identified and validated as a cause of hormone refractory prostate cancer. See Chen, C. D., Welsbie, D. S., Tran, C., Baek, S. H., Chen, R., Vessella, R., Rosenfeld, M. G., and Sawyers, C. L., Molecular determinants of resistance to antiandrogen therapy, Nat. Med., 10: 33-39, 2004, which is hereby incorporated by reference. Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explains why castration and anti-androgens fail to prevent prostate cancer progression and reveals unrecognized properties of hormone refractory prostate cancer.

Bicalutamide (brand name: Casodex) is the most commonly used anti-androgen. While it has an inhibitory effect on AR in hormone sensitive prostate cancer, it fails to suppress AR when cancer becomes hormone refractory. Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Therefore, better AR inhibitors with more potent antagonistic activities and minimal agonistic activities are needed to delay disease progression and to treat the fatal hormone refractory prostate cancer.

Nonsteroidal anti-androgens, such as bicalutamide, have been preferred over steroidal compounds for prostate cancer because they are more selective and have fewer side effects. This class of compounds has been described in many patents such as U.S. Pat. No. 4,097,578, U.S. Pat. No. 5,411,981, U.S. Pat. No. 5,705,654, PCT International Applications WO 97/00071 and WO 00/17163, and U.S. Published Patent Application Number 2004/0009969, all of which are hereby incorporated by reference.

U.S. Pat. No. 5,434,176 includes broad claims which encompass a very large number of compounds, but synthetic routes are only presented for a small fraction of these compounds and pharmacological data are only presented for two of them, and one skilled in the art could not readily envision other specific compounds.

Because the mechanism of hormone refractory prostate cancer was not known, there was no biological system to test these compounds described in these patents for their effect on hormone refractory prostate cancer. Particularly, the ability of AR overexpression in hormone refractory prostate cancer to switch inhibitors from antagonists to agonists was not recognized. Some new properties of hormone refractory prostate cancer are reported in PCT applications US04/42221 and US05/05529, which are hereby incorporated by reference. PCT International Application US05/05529 presented a methodology for identifying androgen receptor antagonist and agonist characteristics of compounds. However, for each compound produced, the time consuming process of determining the antagonist and agonist characteristics of a compound must be determined. That is, there is no method to accurately predict characteristics relevant to treating prostate cancer from the chemical structure of a compound alone.

Some compounds have been reported to be inhibitors of the ligand binding domain (LBD) androgen receptor (AR). Several have been used as drugs to treat prostate cancer, e.g., bicalutamide (Casodex). Several binders of the AR LBD have been identified, e.g., the thiohydantoins, RU59063 and BTID. (Teutsch, G.; Goubet, F.; Battmann, T.; Bonfils, A.; Bouchoux, F.; Cerede, E.; Gofflo, D.; Gaillard-Kelly, M.; Philibert. D. *J. Steroid Biochem. Molec. Biol.* 1994, 48, 111-119; Van Dort, M. E.; Robins, D. M.; Wayburn, B. *J. Med. Chem.* 2000, 43, 3344-3347)

There is a need for new thiohydantoin compounds having desirable pharmacological properties, and synthetic pathways for preparing them. Because activities are sensitive to small structural changes, one compound may be effective in treating prostate cancer, whereas a second compound may be ineffective, even if it differs from the first compound only slightly, say by the replacement of a single substituent.

Identification of compounds which have high potency to antagonize the androgen activity, and which have minimal agonistic activity should overcome hormone refractory prostate cancer (HRPC) and avoid or slow down the progression of hormone sensitive prostate cancer (HSPC). Therefore, there is a need in the art for the identification of selective modulators of the androgen receptor, such as modulators which are non-steroidal, non-toxic, and tissue selective.

SUMMARY OF THE INVENTION

The invention provides a series of compounds having strong antagonistic activities with minimal agonistic activities against AR. These compounds inhibit the growth of hormone refractory prostate cancer.

Particular compounds of the invention include

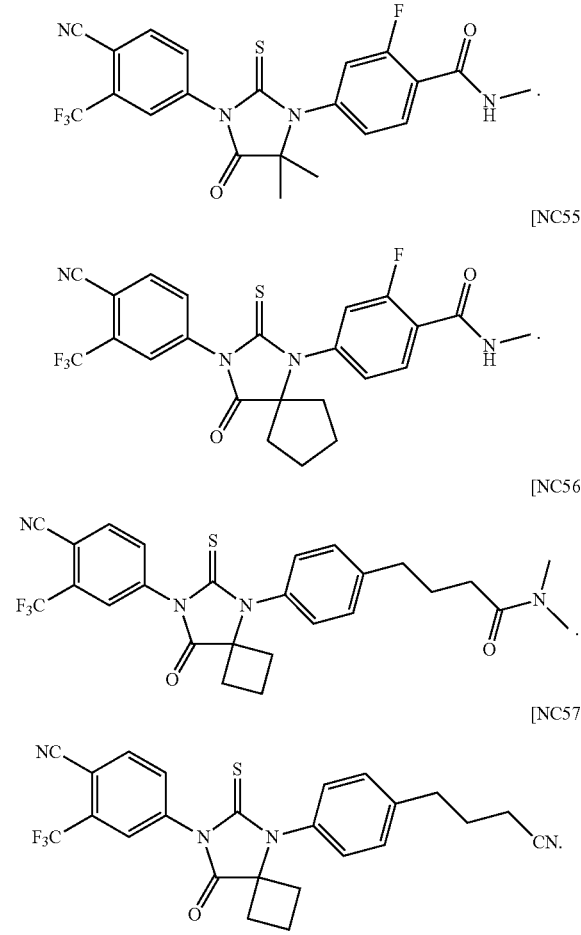

The invention also provides a pharmaceutical composition comprising a therapeutically effective amount of a compound according to any of the preceding compounds or a pharmaceutically acceptable salt thereof, and a pharmaceutically acceptable carrier or diluent.

The invention encompasses a method for treating a hyperproliferative disorder comprising administering such a pharmaceutical composition to a subject in need of such treatment, thereby treating the hyperproliferative disorder. The hyperproliferative disorder may be hormone refractory prostate cancer. The dosage may be in the range of from about 0.001 mg per kg body weight per day to about 100 mg per kg body weight per day, about 0.01 mg per kg body weight per day to about 100 mg per kg body weight per day, about 0.1 mg per kg body weight per day to about 10 mg per kg body weight per day, or about 1 mg per kg body weight per day.

The compound may be administered by intravenous injection, by injection into tissue, intraperitoneally, orally, or nasally. The composition may have a form selected from the group consisting of a solution, dispersion, suspension, powder, capsule, tablet, pill, time release capsule, time release tablet, and time release pill.

The administered compound may be selected from the group consisting of NC54, NC55, NC56, or NC57, or a pharmaceutically acceptable salt thereof. The administered compound may be NC53 or a pharmaceutically acceptable salt thereof.

The invention provides a method of synthesizing NC54 comprising mixing N-Methyl-2-fluoro-4-(1,1-dimethyl-cyanomethyl)-aminobenzamide and 4-Isothiocyanato-2-trifluoromethylbenzonitrile in DMF and heating to form a first mixture, and processing as above.

The invention also provides a method of synthesizing NC55, comprising mixing N-Methyl-2-fluoro-4-(1-cyanocyclopentyl)aminobenzamide, 4-isothiocyanato-2-trifluoromethyl benzonitrile, and DMF and heating under reflux to form a first mixture, and processing as above.

The invention further provides a method of synthesizing NC56, comprising mixing N,N-Dimethyl 4-[4-(1-cyanocyclobutylamino)phenyl]butanamide, 4-isothiocyanato-2-trifluoromethyl benzonitrile, and DMF and heating under reflux to form a first mixture; and processing as above.

The invention provides a method of synthesizing NC57, comprising mixing DMSO, dichloromethane, and oxalyl chloride to form a first mixture, adding 4-(4-(7-(4-Cyano-3-(trifluoromethyl)phenyl)-8-oxo-6-thioxo-5,7-diazaspiro[3,4]octan-5-yl)phenyl)butanamide to the first mixture to form a second mixture; adding triethylamine to the second mixture to form a third mixture; warming the third mixture and quenching with aqueous NH$_4$Cl to form a fourth mixture; extracting an organic layer from the fourth mixture; and isolating the compound from the organic layer.

In an embodiment, a compound has the formula

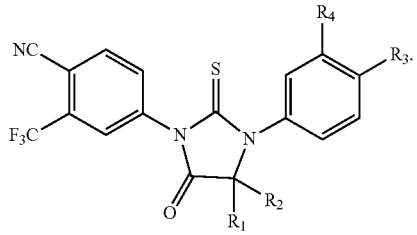

R1 and R2 are independently methyl or, together with the carbon to which they are linked, a cycloalkyl group of 4 to 5 carbon atoms, R3 is selected from the group consisting of carbamoyl, alkylcarbamoyl, carbamoylalkyl, alkylcarbamoylalkyl, cyano, and cyanoalkyl, and R4 is hydrogen or fluorine.

In an embodiment a pharmaceutical composition comprises a therapeutically effective amount of a compound according to claim 1 or a pharmaceutically acceptable salt thereof, and a pharmaceutically acceptable carrier or diluent.

The compound can, for example, have the formula

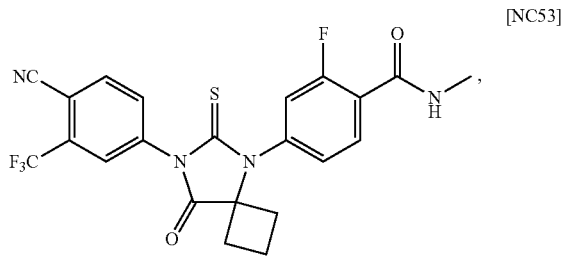

[NC54]: (structure with NC, F₃C-phenyl, thiohydantoin with gem-dimethyl, linked to fluoro-benzamide N-methyl)

[NC55]: (structure with NC, F₃C-phenyl, thiohydantoin with spirocyclopentyl, linked to fluoro-benzamide N-methyl)

[NC56]: (structure with NC, F₃C-phenyl, thiohydantoin with spirocyclobutyl, linked to phenyl-propanamide dimethyl)

[NC57]: (structure with NC, F₃C-phenyl, thiohydantoin with spirocyclobutyl, linked to phenyl-propyl-CN)

A pharmaceutical composition can comprise a therapeutically effective amount of a compound NC54 or a pharmaceutically acceptable salt thereof, and a pharmaceutically acceptable carrier or diluent. A pharmaceutical composition can comprise a therapeutically effective amount of a compound according to claim NC55 or a pharmaceutically acceptable salt thereof, and a pharmaceutically acceptable carrier or diluent.

In an embodiment, a method for treating a hyperproliferative disorder comprises administering a pharmaceutical composition of claim 2 to a subject in need of such treatment, thereby treating the hyperproliferative disorder.

The composition can, for example, have a form selected from the group consisting of a solution, dispersion, suspension, powder, capsule, tablet, pill, time release capsule, time release tablet, and time release pill. The compound can be administered by intravenous injection, by injection into tissue, intraperitoneally, orally, or nasally. The composition can be administered at a dosage of the compound in the range of from about 0.001 mg per kg body weight per day to about 100 mg per kg body weight per day. The composition can be administered at a dosage of the compound in the range of from about 0.01 mg per kg body weight per day to about 100 mg per kg body weight per day. The composition can be administered at a dosage of the compound in the range of from about 0.1 mg per kg body weight per day to about 10 mg per kg body weight per day. The composition can be administered at a dosage of the compound of about 1 mg per kg body weight per day.

There is a method for treating prostate cancer comprising administering a pharmaceutical composition to a subject in need of such treatment, thereby treating the prostate cancer. The pharmaceutical composition can interfere with the transcription of prostate specific antigen mRNA. The pharmaceutical composition can prevent nuclear translocation of an androgen receptor protein. The pharmaceutical composition can destabilize an androgen receptor protein. The composition can be administered orally. The composition can have a form selected from the group consisting of a capsule, tablet, and pill.

In an embodiment, the compound can be NC54, NC55, NC56, NC57, a pharmaceutically acceptable salt of any of these, or combinations thereof.

A method of synthesizing a diaryl compound of formula (structure with NC, F₃C-phenyl-N, thiohydantoin with spiro-azetidine R51, linked to phenyl with R52, R53)

comprises mixing Compound I

Compound I (structure: NC, F₃C-phenyl-N=C=S)

with Compound II

Compound II (structure: cyano-azetidine R51 bearing C with NH-phenyl with R52, R53)

in a first polar solvent to form a mixture, heating the mixture, adding a second polar solvent, the same as or different from the first polar solvent, and an aqueous acid to the mixture, refluxing the mixture, cooling the mixture and combining with water, and separating the diaryl compound from the mixture. R51 can include an alkyl chain of from 1 to 4 carbon atoms. R52 can be cyano, hydroxy, methylcarbamoyl, methylcarbamoyl-substituted alkyl, methylsulfonecarbamoyl-substituted alkyl, methylaminomethyl, dimethylaminomethyl, methylsulfonyloxymethyl, methoxycarbonyl, 3-cyano-4-trifluoromethylphenylcarbamoyl, carbamoyl-substituted alkyl, carboxymethyl, methoxycarbonylmethyl, methanesulfonyl, 4-cyano-3-trifluoromethylphenylcarbamoyl-substituted alkyl, carboxy-substituted alkyl, 4-methanesulfonyl-1-piperazinyl, piperazinyl, hydroxyethylcarbamoyl-substituted alkyl, or hydroxyethoxycarbonyl-substituted alkyl. R53 can be selected from the group consisting of F and H.

In an embodiment R51, comprises an alkyl chain of from 1 to 2 carbon atoms, R52 is selected from the group consisting of carbamoyl and methylcarbamoyl, and R53 is F.

A method of synthesizing a compound of formula

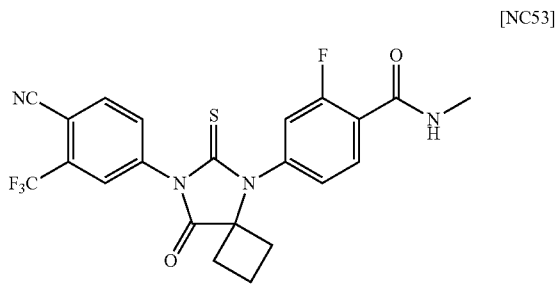 [SMILES: CNC(=O)c1ccc(N2C(=S)N(c3ccc(C#N)c(C(F)(F)F)c3)C(=O)C23CCC3)cc1F]

[NC53]

can include mixing 4-isothiocyanato-2-trifluoromethylbenzonitrile and N-methyl-4-(1-cyanocyclobutylamino)-2-fluorobenzamide in dimethylformamide to form a first mixture, heating the first mixture to form a second mixture, adding alcohol and acid to the second mixture to form a third mixture, refluxing the third mixture to form a fourth mixture, cooling the fourth mixture, combining the fourth mixture with water and extracting an organic layer, and isolating the compound from the organic layer.

A method of synthesizing the compound of claim 4 [NC54], can include mixing N-methyl-2-fluoro-4-(1,1-dimethyl-cyanomethyl)-aminobenzamide and 4-isothiocyanato-2-trifluoromethylbenzonitrile in DMF and heating to form a first mixture, adding an alcohol and an acid to the first mixture to form a second mixture, refluxing the second mixture, cooling the second mixture, combining the second mixture with water and extracting an organic layer, and isolating the compound from the organic layer.

A method of synthesizing the compound of claim 6 [NC55], can include mixing N-methyl-2-fluoro-4-(1-cyanocyclopentyl)aminobenzamide, 4-isothiocyanato-2-trifluoromethyl benzonitrile, and DMF and heating under reflux to form a first mixture, adding an alcohol and an acid to the first mixture to form a second mixture, refluxing the second mixture, cooling the second mixture, combining the second mixture with water and extracting an organic layer, and isolating the compound from the organic layer.

A method of synthesizing the compound of claim 8 [NC56], can include mixing N,N-dimethyl 4-[4-(1-cyanocyclobutylamino)phenyl]butanamide, 4-isothiocyanato-2-trifluoromethyl benzonitrile, and DMF and heating under reflux to form a first mixture, adding an alcohol and an acid to the first mixture to form a second mixture, refluxing the second mixture, cooling the second mixture, combining the second mixture with water and extracting an organic layer, and isolating the compound from the organic layer.

A method of synthesizing the compound of claim 9 [NC57] can include mixing DMSO, dichloromethane, and oxalyl chloride to form a first mixture, adding 4-(4-(7-(4-cyano-3-(trifluoromethyl)phenyl)-8-oxo-6-thioxo-5,7-diazaspiro[3.4]octan-5-yl)phenyl)butanamide to the first mixture to form a second mixture, adding triethylamine to the second mixture to form a third mixture, warming the third mixture and quenching with aqueous NH4Cl to form a fourth mixture, extracting an organic layer from the fourth mixture, isolating the compound from the organic layer.

A method can include providing at least one diarylthiohydantoin compound, measuring inhibition of androgen receptor activity for the compound and determining if the inhibition is above a first predetermined level, measuring stimulation of androgen receptor activity in hormone refractory cancer cells for the compound and determining if the stimulation is below a second predetermined level, selecting the compound if the inhibition is above the first predetermined level and the stimulation is below the second predetermined level. The predetermined levels can be those of bicalutamide. Measuring inhibition can include measuring inhibitory concentration (IC50) in an AR response reporter system or a prostate specific antigen secreting system. Measuring stimulation can include measuring fold induction by increasing concentrations in an AR response reporter system or a prostate specific antigen secreting system. Measuring inhibition and/or stimulation can include measuring an effect of the compound on tumor growth in an animal. The step of measuring inhibition and/or stimulation of androgen receptor activity can include measuring the binding affinity of an androgen receptor to the compound. The step of measuring inhibition and/or stimulation of androgen receptor activity can include measuring prevention of androgen receptor recruitment to at least one of prostate specific antigen enhancer and prostate specific antigen promoter. The step of measuring inhibition and/or stimulation of androgen receptor activity can include measuring prevention of androgen receptor nuclear translocation. The step of measuring inhibition and/or stimulation of androgen receptor activity can include measuring destabilization of an androgen receptor protein.

A method can include contacting a mammalian cell capable of expressing prostate specific antigen with a sufficient amount of a diarylthiohydantoin compound to interfere with the transcription of prostate specific antigen mRNA. The diarylthiohydantoin compound can be selected from the group consisting of NC53, NC54, NC55, NC56, and NC57. The compound can prevent formation of a transcription complex on a prostate specific antigen gene. The compound can prevent an androgen receptor protein from complexing with a prostate specific antigen gene. The compound can prevent an RNA polymerase II from complexing with a prostate specific antigen gene.

A method includes contacting a mammalian cell with a sufficient amount of a diarylthiohydantoin compound to prevent nuclear translocation of an androgen receptor protein and/or to destabilize an androgen receptor protein.

BRIEF DESCRIPTION OF THE DRAWINGS

The following Figures present the results of pharmacological examination of certain compounds.

FIG. 15 also presents a graph providing the pharmacokinetic characteristics of several compounds in terms of compound serum concentration as a function of time.

DETAILED DESCRIPTION

Figure 1:
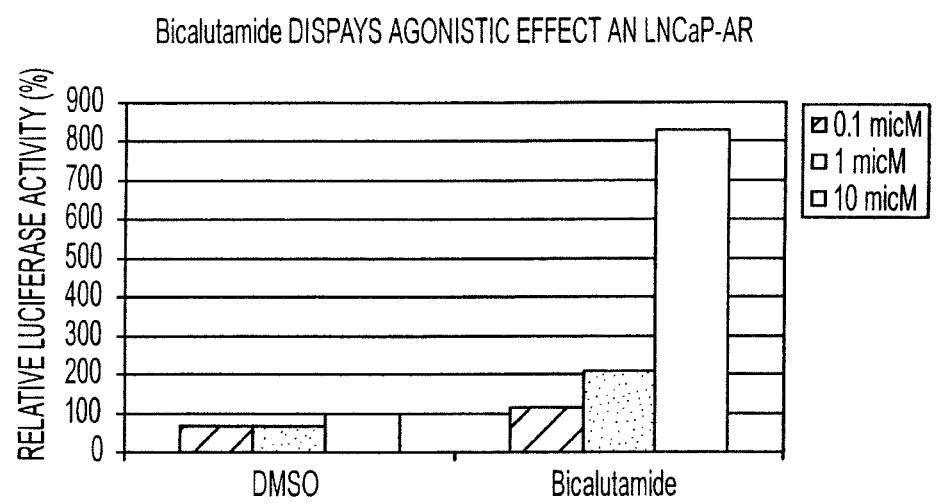
FIG. 1 is a graph depicting that bicalutamide displays an agonistic effect on LNCaP-AR. Agonistic activities of bicalutamide in AR-overexpressed hormone refractory prostate cancer. LNCaP cells with overexpressed AR were treated with increasing concentrations of DMSO as vehicle or bicalutamide in the absence of R1881. Activities of AR response reporter were measured.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Synthesis of Diarylhydantoin Compounds

Example 56

NC54

In the following, air or moisture sensitive reactions were conducted under argon atmosphere using oven-dried glassware and standard syringe/septa techniques. The reactions were monitored with a $SiO_2$ TLC plate under UV light (254 nm) followed by visualization with a p-anisaldehyde or ninhydrin staining solution. Column chromatography was performed on silica gel 60. $^1H$ NMR spectra were measured at 400 MHz in $CDCl_3$ unless stated otherwise and data were reported as follows in ppm (δ) from the internal standard (TMS, 0.0 ppm): chemical shift (multiplicity, integration, coupling constant in Hz.).

Formula 37

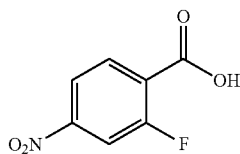

Periodic acid (1.69 g, 7.41 mmol) was dissolved in acetonitrile (25 mL) by vigorous stirring, and then chromium trioxide (0.16 g, 1.60 mmol) was dissolved into the solution. 2-Fluoro-4-nitrotoluene (0.33 g, 2.13 mmol) was added to the above solution with stirring. A white precipitate formed immediately with exothermic reaction. After 1 h of stirring, the supernatant liquid of the reaction mixture was decanted to a flask, and the solvent was removed by evaporation. The residues were extracted with methylene chloride (2×30 mL) and water (2×30 mL). The organic layer was dried over $MgSO_4$, and concentrated to give 2-Fluoro-4-nitrobenzoic acid (Formula 37) (0.32 mg, 81%) as a white solid. $^1$H NMR δ 8.06 (ddd, 1H, J=9.9, 2.2 and 0.3), 8.13 (ddd, 1H, J=8.6, 2.2 and 0.9), 8.25 (ddd, 1H, J=8.6, 7.0 and 0.3).

Formula 38

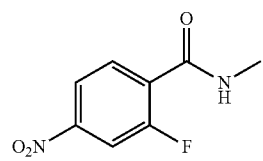

Thionyl chloride (0.15 g, 1.30 mmol) was added slowly to a solution of 2-fluoro-4-nitrobenzoic acid (Formula 37) (0.20 g, 1.10 mmol) in DMF (5 mL) cooled at −5° C. The mixture was stirred for an additional 1 hour at −5° C. Excess methylamine (freshly distilled from its 40% aqueous solution) was added to the reaction medium. The second mixture was stirred for an additional 1 hour. Ethyl acetate (50 mL) was added to the mixture, which was washed with brine (2×50 ml). The organic layer was dried over $MgSO_4$, and concentrated to yield N-Methyl-2-fluoro-4-nitrobenzamide (Formula 38) (0.18 g, 85%) as a yellowish solid. $^1$H NMR (acetone-$d_6$) δ 3.05 (d, 3H, J=4.3), 6.31 (dd, 1H, J=13.5 and 2.1), 6.40 (dd, 1H, J=8.6 and 2.1), 7.64 (dd, 1H, J=8.6 and 8.6).

Formula 39

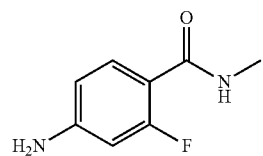

A mixture of N-Methyl-2-fluoro-4-nitrobenzamide (Formula 38) (0.18 g, 0.91 mmol) and iron (0.31 g, 5.60 mmol) in ethyl acetate (5 mL) and acetic acid (5 mL) was refluxed for 1 h. The solid particles were filtered off. The filtrate was washed with water and extracted with ethyl acetate. The organic layer was dried over $MgSO_4$, concentrated and the residue was purified with $SiO_2$ column chromatography (dichloromethane:acetone, 95:5) to give N-Methyl-2-fluoro-4-aminobenzamide (Formula 39) (0.14 g, 92%) as an off-white solid. $^1$H NMR (acetone-$d_6$) δ 2.86 (d, 3H, J=4.3), 5.50 (br s, 2H), 6.37 (dd, 1H, J=14.7 and 2.1), 6.50 (dd, 1H, J=8.6 and 2.1), 7.06 (br s, 1H), 7.68 (dd, 1H, J=8.8 and 8.8).

Formula 40

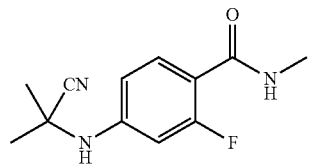

A mixture of N-Methyl-2-fluoro-4-aminobenzamide (Formula 39) (96 mg, 0.57 mmol), acetone cyanohydrin (0.3 mL, 3.14 mmol) and magnesium sulfate (50 mg) was heated to 80° C. and stirred for 12 h. To the medium was added ethyl acetate (25 mL) and then washed with water (2×25 mL). The organic layer was dried over $MgSO_4$ and concentrated and the residue was purified with $SiO_2$ column chromatography (dichloromethane:acetone, 95:5) to give N-Methyl-2-fluoro-4-(1,1-dimethyl-cyanomethyl)-aminobenzamide (Formula 40) (101 mg, 75%) as a white solid. $^1$H NMR δ 1.74 (s, 6H), 2.98 (dd, 3H, J=4.8 and 1.1), 6.58 (dd, 1H, J=14.6 and 2.3), 6.63 (dd, 1H, J=8.7 and 2.3), 6.66 (br s, 1H), 7.94 (dd, 1H, J=8.7 and 8.7).

Formula 41

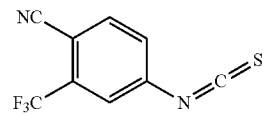

4-Amino-2-trifluoromethylbenzonitrile (2.23 g, 12 mmol) was added portionwise over 15 min into a well-stirred heterogeneous mixture of thiophosgene (1 mL, 13 mmol) in water (22 mL) at room temperature. Stirring was continued for an additional 1 h. The reaction medium was extracted with chloroform (3×15 ml). The combined organic phase was dried over $MgSO_4$ and evaporated to dryness under reduced pressure to yield desired product 4-Isothiocyanato-2-trifluoromethylbenzonitrile (Formula 41) as brownish solid and was used as such for the next step (2.72 g, 11.9 mmol, 99%). $^1$H NMR δ 7.49 (dd, 1H, J=8.3 and 2.1), 7.59 (d, 1H, J=2.1), 7.84 (d, 1H, J=8.3).

NC54 (Formula 42)

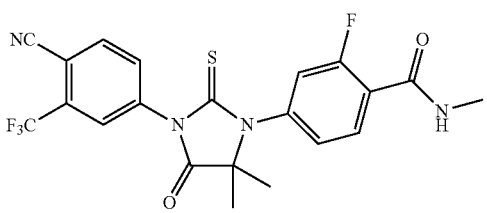

56-1) NC54

A mixture of N-Methyl-2-fluoro-4-(1,1-dimethyl-cyanomethyl)-aminobenzamide (Formula 40) (30 mg, 0.13 mmol) and 4-Isothiocyanato-2-trifluoromethylbenzonitrile (Formula 41) (58 mg, 0.26 mmol) in DMF (1 mL) was heated under microwave irradiation at 100° C. for 11 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO₄, concentrated and the residue was purified with SiO₂ column chromatography (dichloromethane:acetone, 95:5) to give NC54 (Formula 42) (15 mg, 25%) as a colorless crystal. ¹H NMR δ 1.61 (s, 6H), 3.07 (d, 3H, J=4.1), 6.71 (m, 1H), 7.15 (dd, 1H, J=11.7 and 2.0), 7.24 (dd, 1H, J=8.4 and 2.0), 7.83 (dd, 1H, J=8.2 and 2.1), 7.95 (d, 1H, J=2.1), 7.99 (d, 1H, J=8.2), 8.28 (dd, 1H, J=8.4 and 8.4).

Example 57

Formula 43

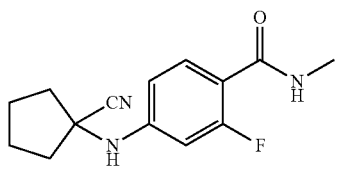

A mixture of N-Methyl-2-fluoro-4-aminobenzamide (Formula 39) (62 mg, 0.37 mmol), cyclopentanone (0.07 mL, 0.74 mmol) and TMSCN (0.1 mL, 0.74 mmol) was heated to 80° C. and stirred for 13 h. To the medium was added ethyl acetate (2×20 mL) and then washed with water (2×20 mL). The organic layer was dried over MgSO₄ and concentrated and the residue was purified with silica gel column chromatography (dichloromethane:acetone, 95:5) to give N-Methyl 2-fluoro-4-(1-cyanocyclopentyl)aminobenzamide (Formula 43) (61 mg, 63%) as a white solid. ¹H NMR δ 7.95 (dd, 1H, J=8.8, 8.8 Hz), 6.65 (br s, 1H), 6.59 (dd, 1H, J=8.8, 2.3 Hz), 6.50 (dd, 1H, J=14.6, 2.3 Hz), 4.60 (br s, 1H), 2.99 (dd, 3H, J=4.8, 1.1 Hz), 2.36-2.45 (m, 2H), 2.10-2.18 (m, 2H), 1.82-1.95 (m, 4H).

NC55 (Formula 44)

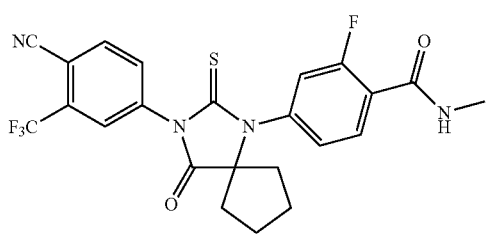

57-1) NC55

A mixture of N-Methyl 2-fluoro-4-(1-cyanocyclopentyl) aminobenzamide (Formula 43) (57 mg, 0.22 mmol) and 4-isothiocyanato-2-trifluoromethyl benzonitrile (0.15 g, 0.65 mmol) in DMF (3 mL) was heated under microwave irradiation (open vessel) at 130° C. for 12 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO₄, concentrated and the residue was purified with silica gel column chromatography (dichloromethane:acetone, 95:5) to give 4-(3-(4-Cyano-3-(trifluoromethyl)phenyl)-4-oxo-2-thioxo-1,3-diazaspiro [4.4]nonan-1-yl)-2-fluoro-N-methylbenzamide, NC55 (Formula 44) (8 mg, 7%) as a pale yellowish solid. ¹H NMR δ 8.28 (dd, 1H, J=8.4, 8.4 Hz), 7.98 (d, 1H, J=8.3 Hz), 7.96 (d, 1H, J=1.8 Hz), 7.84 (dd, 1H, J=8.3, 1.8 Hz), 7.27 (dd, 1H, J=8.4, 1.8 Hz), 7.17 (dd, 1H, J=11.7, 1.8 Hz), 6.67-6.77 (m, 1H), 3.07 (d, 3H, J=4.3 Hz), 2.32-2.41 (m, 2H), 2.13-2.21 (m, 2H), 1.85-1.96 (m, 2H), 1.49-1.59 (m, 2H).

Example 58

Formula 45

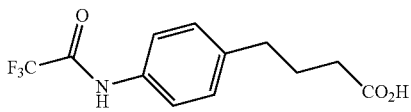

Trifluoroacetic anhydride (0.85 mL, 6.14 mmol) was added to a solution of 4-(4-aminophenyl)butyric acid (0.5 g, 2.79 mmol) in chloroform (10 mL) at 0° C. The mixture was warmed to room temperature and stirred for 3 hours. The mixture was partitioned with chloroform (20 mL) and water (20 mL). The organic layer was dried over MgSO₄, concentrated and the residue was purified with silica gel column chromatography (dichloromethane:acetone, 9:1) to give 4-[4-(2,2,2-Trifluoroacetylamino)phenyl]butanoic acid (Formula 45) (0.53 g, 69%). ¹H NMR δ7.81 (br s, 1H), 7.48 (d, 2H, J=8.5 Hz), 7.22 (d, 2H, J=8.5 Hz), 2.68 (t, 2H, J=7.5 Hz), 2.38 (t, 2H, J=7.5 Hz), 1.96 (p, 2H, J=7.5 Hz).

Formula 46

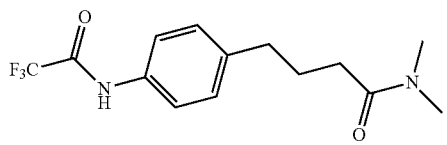

Thionyl chloride (71 mg, 0.60 mmol) was added slowly to a solution of 4-[4-(2,2,2-Trifluoroacetylamino)phenyl]butanoic acid (Formula 45) (0.15 g, 0.55 mmol) in DMF (5 mL) cooled at −5° C. The mixture was stirred for an additional 1 hour at −5° C. Excess dimethylamine (freshly distilled from its 40% aqueous solution) was added to the reaction medium. The second mixture was stirred for an additional 1 hour. Ethyl acetate (50 mL) was added to the mixture, which was washed with brine (2×50 ml). The organic layer was dried over MgSO₄, and concentrated to yield N,N-Dimethyl 4-[4-(2,2,2-Trifluoroacetylamino)phenyl]butanamide (Formula 46) (0.17 g, quant.) as a yellowish solid. ¹H NMR δ 9.70 (br s, 1H), 7.55 (d, 2H, J=8.6 Hz), 7.11 (d, 2H, J=8.6 Hz), 2.91 (s, 3H), 2.89 (s, 3H), 2.60 (t, 2H, J=7.7 Hz), 2.27 (t, 2H, J=7.7 Hz), 1.89 (p, 2H, J=7.7 Hz).

Formula 47

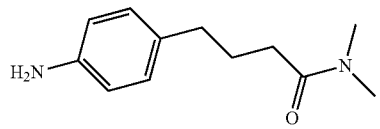

1 N NaOH solution (3 mL) was added to a solution of N,N-Dimethyl 4-[4-(2,2,2-Trifluoroacetylamino)phenyl]butanamide (Formula 46) (0.17 g, 0.55 mmol) in methanol (2 mL) at room temperature. The mixture was stirred for 14 hour. The mixture was partitioned with chloroform (25 mL) and water (25 mL). The organic layer was dried over MgSO₄, and concentrated and the residue was purified with silica gel column chromatography (dichloromethane:acetone, 9:1) to give N,N-Dimethyl 4-(4-aminophenyl)butanamide (Formula 47) (74 mg, 66%) as a white solid. $^1$H NMR δ 6.97 (d, 2H, J=8.3 Hz), 6.61 (d, 2H, J=8.3 Hz), 3.56 (br s, 2H), 2.92 (s, 6H), 2.56 (t, 2H, J=7.7 Hz), 2.28 (t, 2H, J=7.7 Hz), 1.91 (p, 2H, J=7.7 Hz).

Formula 48

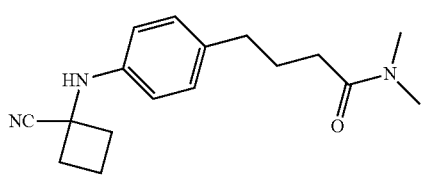

A mixture of N,N-Dimethyl 4-(4-aminophenyl)butanamide (Formula 47) (74 mg, 0.36 mmol), cyclobutanone (54 mg, 0.78 mmol) and TMSCN (77 mg, 0.78 mmol) was heated to 80° C. and stirred for 15 h. To the medium was added ethyl acetate (2×20 mL) and then washed with water (2×20 mL). The organic layer was dried over MgSO₄ and concentrated and the residue was purified with silica gel column chromatography (dichloromethane:acetone, 9:1) to give N,N-Dimethyl 4-[4-(1-cyanocyclobutylamino)phenyl]butanamide (Formula 48) (58 mg, 57%) as a white solid. $^1$H NMR δ 7.07 (d, 2H, J=8.5 Hz), 6.59 (d, 2H, J=8.5 Hz), 3.94 (br s, 1H), 2.94 (s, 3H), 2.93 (s, 3H), 2.75-2.83 (m, 2H), 2.60 (t, 2H, J=7.6 Hz), 2.33-2.42 (m, 2H), 2.30 (t, 2H, J=7.6 Hz), 2.11-2.28 (m, 2H), 1.93 (p, 2H, J=7.6 Hz).

NC56 Formula 49

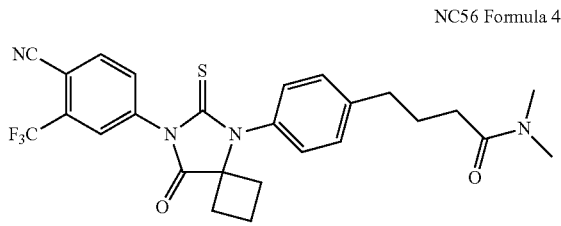 [SMILES: CN(C)C(=O)CCCc1ccc(N2C(=S)N(c3ccc(C#N)c(C(F)(F)F)c3)C(=O)C23CCC3)cc1]

A mixture of N,N-Dimethyl 4-[4-(1-cyanocyclobutylamino)phenyl]butanamide (Formula 48) (58 mg, 0.20 mmol) and 4-isothiocyanato-2-trifluoromethyl benzonitrile (74 mg, 0.32 mmol) in DMF (3 mL) was heated under reflux for 2 hours. To this mixture was added methanol (20 mL) and aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO₄, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]octan-5-yl)phenyl)-N,N-dimethylbutanamide, NC56 (Formula 49) (44 mg, 42%) as a pale yellowish solid. $^1$H NMR δ 7.98 (s, 1H), 7.97 (d, 1H, J=8.2 Hz), 7.86 (d, 1H, J=8.2 Hz), 7.42 (d, 2H, J=8.3 Hz), 7.22 (d, 2H, J=8.3 Hz), 2.99 (s, 3H), 2.96 (s, 3H), 2.78 (t, 2H, J=7.5 Hz), 2.62-2.70 (m, 2H), 2.52-2.63 (m, 2H), 2.40 (t, 2H, J=7.5 Hz), 2.15-2.30 (m, 1H), 2.04 (p, 2H, J=7.5 Hz), 1.62-1.73 (m, 1H).

Example 59

Formula 50

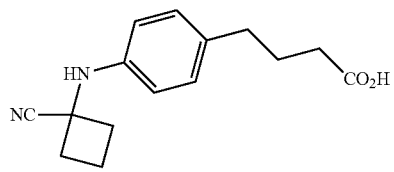

A mixture of 4-(4-aminophenyl)butyric acid (0.20 g, 1.12 mmol), cyclobutanone (0.17 mL, 2.23 mmol) and TMSCN (0.30 mL, 2.23 mmol) was heated to 80° C. and stirred for 13 h. To the medium was added ethyl acetate (2×30 mL) and then washed with water (2×30 mL). The organic layer was dried over MgSO₄ and concentrated and the residue was purified with silica gel column chromatography (dichloromethane: acetone, 9:1) to give 4-[4-(1-Cyanocyclobutylamino)phenyl]butanoic acid (Formula 50) (0.21 g, 74%) as a yellowish solid. $^1$H NMR δ 7.06 (d, 2H, J=8.6 Hz), 6.59 (d, 2H, J=8.6 Hz), 2.75-2.83 (m, 2H), 2.59 (t, 2H, J=7.5 Hz), 2.37 (t, 2H, J=7.5 Hz), 2.33-2.42 (m, 2H), 2.11-2.28 (m, 2H), 1.92 (p, 2H, J=7.5 Hz).

Formula 51

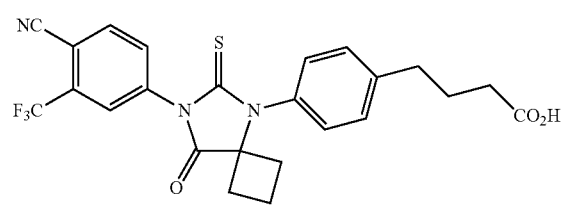

A mixture of 4-[4-(1-Cyanocyclobutylamino)phenyl]butanoic acid (Formula 50) (0.21 g, 0.83 mmol) and 4-isothiocyanato-2-trifluoro benzonitrile (0.25 g, 1.08 mmol) in toluene (10 mL) was heated under reflux for 1 hours. To this mixture was added aq. 1 N HCl (5 mL). The second mixture was refluxed for 1.5 h. After being cooled to room temperature, the reaction mixture was poured into cold water (50 mL) and extracted with ethyl acetate (50 mL). The organic layer was dried over MgSO₄, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]octan-5-yl)phenyl)butanoic acid, NC122 (Formula 51) (60 mg, 15%). $^1$H NMR δ 7.98 (d, 1H, J=1.8 Hz), 7.97 (d, 1H, J=8.3 Hz), 7.86 (dd, 1H, J=8.3, 1.8 Hz), 7.42 (d, 2H, J=8.5 Hz), 7.24 (d, 2H, J=8.5 Hz), 2.79 (t, 2H, J=7.5 Hz), 2.62-2.68 (m, 2H), 2.51-2.59 (m, 2H), 2.47 (t, 2H, J=7.5 Hz), 2.14-2.26 (m, 1H), 2.06 (p, 2H, J=7.5 Hz), 1.60-1.70 (m, 1H).

Example 61

NC57 Formula 53

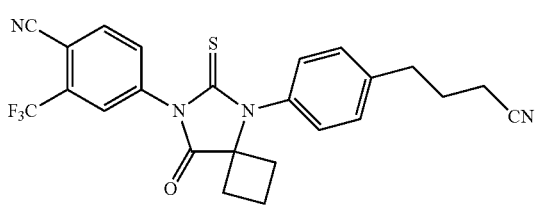

A solution of DMSO (0.01 mL, 0.12 mmol) in dry dichloromethane (1 mL) was added to a stirred solution of oxalyl chloride (0.01 mL, 0.09 mmol) in dry dichloromethane (2 mL) at −78° C. After 15 min, a dichloromethane solution of 4-(4-(7-(4-Cyano-3-(trifluoromethyl)phenyl)-8-oxo-6-thioxo-5,7-diazaspiro[3.4]octan-5-yl)phenyl)butanamide, NC47 (Formula 52) (35 mg, 0.07 mmol) was added to the reaction mixture. Stirring was continued for 20 min at −78° C., and then triethylamine (0.03 mL, 0.22 mmol) was added. After 30 min at −78° C., the reaction mixture was warmed to room temperature and then reaction was quenched with saturated aq. NH$_4$Cl solution. The reaction mixture was diluted with dichloromethane, and extracted with dichloromethane. The organic layer was dried over MgSO$_4$, concentrated and chromatographed (dichloromethane:acetone, 95:5) to yield 4-(5-(4-(3-Cyanopropyl)phenyl)-8-oxo-6-thioxo-5,7-diazaspiro[3.4]octan-7-yl)-2-(trifluoromethyl)benzonitrile, NC57 (Formula 53) (29 mg, 87%) as a viscous oil. $^1$H NMR δ 7.98 (d, 1H, J=1.8 Hz), 7.98 (d, 1H, J=8.3 Hz), 7.86 (dd, 1H, J=8.3, 1.8 Hz), 7.43 (d, 2H, J=8.4 Hz), 7.27 (d, 2H, J=8.4 Hz), 2.90 (t, 2H, J=7.3 Hz), 2.63-2.73 (m, 2H), 2.52-2.62 (m, 2H), 2.42 (t, 2H, J=7.3 Hz), 2.18-2.30 (m, 1H), 2.07 (p, 2H, J=7.3 Hz), 1.63-1.73 (m, 1H).

One skilled in the art could modify and/or combine the syntheses described herein to make other diarylhydantoin compounds.

Pharmacological Examination of the Compounds

Compounds for which synthetic routes are described above were identified through screening on hormone refractory prostate cancer cells for antagonistic and agonistic activities against AR utilizing screening procedures similar to those in PCT applications US04/42221 and US05/05529, which are hereby incorporated by reference. A number of compounds exhibited potent antagonistic activities with minimal agonistic activities for over expressed AR in hormone refractory prostate cancer.

In Vitro Biological Assay

Effect of Compounds on AR by a Reporter Assay

Figure 2:
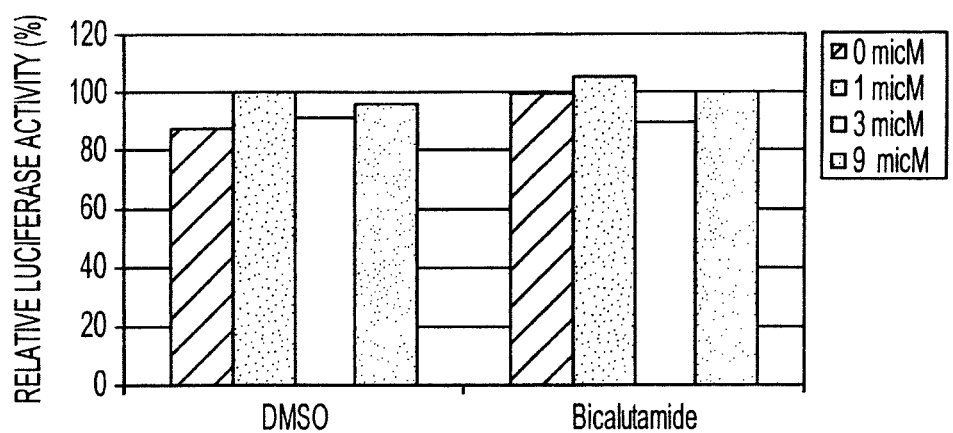
FIG. 2 is a graph depicting an antagonistic assay of bicalutamide on LNCaP-AR. Agonistic activities of bicalutamide in hormone sensitive prostate cancer. LNCaP cells were treated with increasing concentrations of DMSO as vehicle or bicalutamide in the absence of R1881. Activities of AR response reporter were measured.

The compounds were subjected to tests using an artificial AR response reporter system in a hormone refractory prostate cancer cell line. In this system, the prostate cancer LNCaP cells were engineered to stably express about 5-fold higher level of AR than endogenous level. The exogenous AR has similar properties to endogenous AR in that both are stabilized by a synthetic androgen R1881. The AR-over expressed cells were also engineered to stably incorporate an AR response reporter and the reporter activity of these cells shows features of hormone refractory prostate cancer. It responds to low concentration of a synthetic androgen R1881, is inhibited only by high concentrations of bicalutamide (see Table 1), and displays agonistic activity with bicalutamide (FIG. 1 and Table 2). Consistent with published data, bicalutamide inhibited AR response reporter and did not have agonistic activity in hormone sensitive prostate cancer cells (FIG. 2).

TABLE 1

Antagonistic activities against AR in hormone refractory prostate cancer, measured by an AR response reporter and by endogenous PSA expression.

| Example | Name | IC50 (nM) Reporter | IC50 (nM) PSA |
|---|---|---|---|
| Bicalutamide Comparative | N-[4-cyano-3-(trifluoromethyl)phenyl]-3-[(4-fluorophenyl)sulfonyl]-2-hydroxy-2-methylpropanamide | 889 | >1000 |
| 29 Comparative | 4-[3-(4-hydroxybutyl)-4,4-dimethyl-5-oxo-2-thioxoimidazolidin-1-yl]-2-trifluoromethylbenzonitrile | No (*) | No |
| 6-2 (6b) [NC10] | 4-[3-phenyl-4,4-dimethyl-5-oxo-2-thioxoimidazolidin-1-yl]-2-trifluoromethylbenzonitrile | 149 | n/a (**) |
| 5-3b (5c) [NC2] | 4-[3-(4-methylphenyl)-4,4-dimethyl-5-oxo-2-thioxoimidazolidin-1-yl]-2-trifluoromethyl-benzonitrile | 125 | 132 |
| 3-3 (3c) [NC3] | 4-[3-(4-hydroxyphenyl)-4,4-dimethyl-5-oxo-2-thioxoimidazolidin-1-yl]-2-trifluoromethylbenzonitrile | 137 | 122 |
| 2-4 (2d) [NC4] | 4-[3-(4-aminophenyl)-4,4-dimethyl-5-oxo-2-thioxoimidazolidin-1-yl]-2-trifluoromethylbenzonitrile | 273 | n/a |
| 4 (4a) [NC5] | Chloroacetic acid 4-[3-(4-cyano-3-trifluoromethylphenyl)-5,5-dimethyl-4-oxo-2-thioxoimidazolidin-1-yl]phenyl ester | 131 | n/a |
| 8-2 (8b) [NC6] | 4-(4-Oxo-2-thioxo-1-(4-methylphenyl)-1,3-diazaspiro[4.4]non-3-yl)-2-trifluoromethylbenzonitrile | 147 | n/a |
| 7-3b (7c) [NC7] | 4-(8-oxo-6-thioxo-5-(4-methylphenyl)-5,7-diazaspiro[3.4]oct-7-yl)-2-trifluoromethylbenzonitrile | 124 | 128 |
| 9-3 (9c) [NC8] | 4-(4-Oxo-2-thioxo-1-(4-methylphenyl)-1,3-diazaspiro[4.5]dec-3-yl)-2-trifluoromethylbenzonitrile | 194 | n/a |
| 10-3 (10c) [NC9] | 4-(4-oxo-2-thioxo-1-(4-methylphenyl)-1,3-diazaspiro[4.5]undec-3-yl)-2-trifluoromethylbenzonitrile | 232 | n/a |
| 28 Comparative (28a) [NC10] | 4-(8-methyl-4-oxo-2-thioxo-1,3,8-triazaspiro[4.5]dec-3-yl)-2-trifluoromethylbenzonitrile | No | n/a |
| 27-3 (27c) [NC11] | 4-(8-methyl-4-oxo-2-thioxo-1-(4-methylphenyl)-1,3,8-triazaspiro[4.5]dec-3-yl)-2-trifluoromethylbenzonitrile | 638 | n/a |
| 26 (26a) [NC12] | 4-[1-(4-cyanophenyl)-4-oxo-2-thioxo-1,3-diazaspiro[4.4]non-3-yl]-2-trifluoromethylbenzonitrile | 469 | n/a |
| 25 (25a) [NC13] | 4-[1-(4-nitrophenyl)-4-oxo-2-thioxo-1,3-diazaspiro[4.4]non-3-yl]-2-trifluoromethylbenzonitrile | 498 | n/a |
| 12-2 (12b) [NC15] | 4-(8-oxo-6-thioxo-5-(4-biphenyl)-5,7-diazaspiro[3.4]oct-7-yl)-2-trifluoromethylbenzonitrile | 283 | n/a |

TABLE 1-continued

Antagonistic activities against AR in hormone refractory prostate cancer,
measured by an AR response reporter and by endogenous PSA expression.

| Example | Name | IC50 (nM) Reporter | IC50 (nM) PSA |
|---|---|---|---|
| 11-2 (11b) [NC16] | 4-(8-oxo-6-thioxo-5-(4-hydroxyphenyl)-5,7-diazaspiro[3.4]oct-7-yl)-2-trifluoromethylbenzonitrile | 162 | n/a |
| 17 (17a) [NC17] | 4-[3-(4-hydroxyphenyl)-4,4-dimethyl-2,5-dithioxoimidazolidin-1-yl]-2-trifluoromethylbenzonitrile | 278 | 287 |
| 18 (18a) [NC18] | 4-[3-(4-hydroxyphenyl)-4,4-dimethyl-2,5-dioxoimidazolidin-1-yl]-2-trifluoromethylbenzonitrile | 369 | 511 |
| 22-2 (22b) [NC19] | 2-[3-(4-cyano-3-trifluoromethylphenyl)-5,5-dimethyl-4-oxo-2-thioxoimidazolidin-1-yl]benzoic acid | 523 | >500 |
| 20-2 (20b) [NC20] | 4-(4,4-dimethyl-5-oxo-2-thioxo-3-(4-trifluoromethylphenyl)imidazolidin-1-yl)-2-trifluoromethylbenzonitrile | 143 | 144 |
| 21-2 (21b) [NC21] | 4-(4,4-bischloromethyl-5-oxo-2-thioxo-3-(4-methylphenyl)imidazolidin-1-yl)-2-trifluoromethylbenzonitrile | 521 | >500 |
| 19-2 (19b) [NC22] | 4-(4-fluoromethyl-4-methyl-5-oxo-2-thioxo-3-(4-methylphenyl)imidazolidin-1-yl)-2-trifluoromethylbenzonitrile | 126 | 129 |
| 23-2 (23b) [NC23] | 4-(8-oxo-6-thioxo-5-(2-methylphenyl)-5,7-diazaspiro[3.4]oct-7-yl)-2-trifluoromethylbenzonitrile | 258 | 232 |
| 30-2 Comparative (30b) [NC24] | 4-(5-methyl-8-oxo-6-thioxo-5,7-diazaspiro[3.4]oct-7-yl)-2-trifluoromethylenzonitrile | No | No |
| 30-3 Comparative (30c) [NC25] | 4-(5-methyl-6,8-dioxo-5,7-diazaspiro[3.4]oct-7-yl)-2-trifluoromethylbenzonitrile | No | No |
| 31-2 Comparative (31b) [NC26] | 4-(1-methyl-4-oxo-2-thioxo-1,3-diazaspiro[4.4]non-3-yl)-2-trifluoromethylbenzonitrile | No | No |
| 31-3 Comparative (31c) [NC27] | 4-(1-methyl-2,4-dioxo-1,3-diaza-spiro[4.4]non-3-yl)-2-trifluoromethylbenzonitrile | No | No |
| 24-3 Comparative (24c) [NC28] | 4-(4-oxo-2-thioxo-1,3-diazaspiro[4.4]non-3-yl)-2-trifluoromethylbenzonitrile | No | No |
| 15-2 (15b) [NC29] | 4-[4,4-dimethyl-3-(4-pyridin-2-yl)-5-oxo-2-thioxoimidazolidin-1-yl]-2-trifluoromethylbenzonitrile | 723 | n/a |
| 14-2 (14b) [NC30] | 4-[4,4-dimethyl-3-(4-methylpyridin-2-yl)-5-oxo-2-thioxoimidazolidin-1-yl]-2-trifluoromethylbenzonitrile | 457 | n/a |
| 16-2 Comparative (16b) [NC31] | 4-[5-(5-methyl-2H-pyrazol-3-yl)-8-oxo-6-thioxo-5,7-diaza-spiro[3.4]oct-7-yl]-2-trifluoromethyl-benzonitrile | >1000 | n/a |
| 13-2 (12b) [NC32] | 4-(8-oxo-6-thioxo-5-(4-biphenyl)-5,7-diazaspiro[3.4]oct-7-yl)-2-trifluoromethylbenzonitrile | >1000 | n/a |
| 32 (32a) [NC33] | 4-(8-methylimino-6-thioxo-5-p-tolyl-5,7-diaza-spiro[3.4]oct-7-yl)-2-trifluoromethyl-benzonitrile | 222 | 421 |
| 33 (33a) [NC34] | 1-[3-(4-cyano-3-trifluoromethyl-phenyl)-5,5-dimethyl-2-thioxo-1-p-tolyl-imidazolidin-4-ylidene]-3-ethyl-thiourea | 157 | 239 |
| 34 (34a) [NC35] | 1-[7-(4-cyano-3-trifluoromethyl-phenyl)-6-thioxo-5-p-tolyl-5,7-diaza-spiro[3.4]oct-8-ylidene]-3-phenyl-thiourea | 176 | 276 |
| 35 (35a) [NC36] | 1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea | 144 | 158 |
| 36-2 (36b) [NC37] | 4-[8-(4-hydroxymethyl-phenyl)-5-oxo-7-thioxo-6-aza-spiro[3.4[oct-6-yl]-2-trifluoromethyl-benzonitrile | 311 | 337 |
| 37 (37a) [NC38] | 4-[5-(4-formylphenyl)-8-oxo-6-thioxo-5,7-diazaspiro[3.4]oct-7-yl]-2-trifluoromethyl-benzonitrile | n/a | 263 |
| 38 (38a) [NC39] | 4-{5-[4-(1-hydroxyethyl)-phenyl]-8-oxo-6-thioxo-5,7-diazaspiro[3.4]oct-7-yl}-2-trifluoromethyl-benzonitrile | n/a | 187 |
| 39 (39a) [NC40] | 3-{4-[7-(4-cyano-3-trifluoromethylphenyl)-8-oxo-6-thioxo-5,7-diazaspiro[3.4]oct-5-yl]-phenyl}-acrylic acid ethyl ester | n/a | 197 |
| 40 (40a) [NC41] | 4-{5-[4-(3-hydroxypropenyl)-phenyl]-8-oxo-6-thioxo-5,7-diazaspiro[3.4]oct-7-yl]-2-trifluoromethylbenzonitrile | n/a | 114 |
| 41-2 (41b) [NC42] | 3-{4-[7-(4-cyano-3-trifluoromethylphenyl)-8-oxo-6-thioxo-5,7-diazaspiro[3.4]oct-5-yl]-phenyl}-propionic acid methyl ester | No | n/a |
| 41-4 (41d) [NC43] | 3-{4-[7-(4-cyano-3-trifluoromethylphenyl)-8-oxo-6-thioxo-5,7-diaza-spiro[3.4]oct-5-yl]-phenyl}-propionamide | 224 | n/a |
| 41-5 (41e) [NC44] | 3-{4-[7-(4-Cyano-3-trifluoromethylphenyl)-8-oxo-6-thioxo-5,7-diaza-spiro[3.4]oct-5-yl]-phenyl}-N-methyl-propionamide | 234 | n/a |

TABLE 1-continued

Antagonistic activities against AR in hormone refractory prostate cancer, measured by an AR response reporter and by endogenous PSA expression.

| Example | Name | IC50 (nM) Reporter | IC50 (nM) PSA |
|---|---|---|---|
| 41-6 (41f) [NC45] | 3-{4-[7-(4-cyano-3-trifluoromethylphenyl)-8-oxo-6-thioxo-5,7-diaza-spiro[3.4]oct-5-yl]-phenyl}-N-(2-hydroxyethyl)-propionamide | 732 | n/a |
| 42-2 (42b) [NC46] | 4-{4-[7-(4-cyano-3-trifluoromethylphenyl)-8-oxo-6-thioxo-5,7-diazaspiro[3.4]oct-5-yl]-phenyl}-butyric acid methyl ester | 432 | n/a |
| 42-4 (42d) [NC47] | 4-{4-[7-(4-Cyano-3-trifluoromethylphenyl)-8-oxo-6-thioxo-5,7-diaza-spiro[3.4]oct-5-yl]-phenyl}-butyramide | 112 | n/a |
| 42-5 (42e) [NC48] | 4-{4-[7-(4-Cyano-3-trifluoromethylphenyl)-8-oxo-6-thioxo-5,7-diaza-spiro[3.4]oct-5-yl]-phenyl}-N-methyl-butyramide | 92 | n/a |
| 43-4 (43e) [NC49] | 4-[8-Oxo-5-(4-piperazin-1-yl-phenyl)-6-thioxo-5,7-diazaspiro[3.4]oct-7-yl]-2-trifluoromethylbenzonitrile | 718 | n/a |
| 43-5 (43f) [NC50] | 4-{5-[4-(4-methanesulfonylpiperazin-1-yl)-phenyl]-8-oxo-6-thioxo-5,7-diazaspiro[3.4]oct-7-yl}-2-trifluoromethylbenzonitrile | 138 | n/a |
| 44-2 (44b) [NC51] | 44-2) 3-{4-[7-(4-Cyano-3-trifluoromethyl-phenyl)-8-oxo-6-thioxo-5,7-diaza-spiro[3.4]oct-5-yl]-phenyl}-acrylamide, | | 113 |

(*) No: the compound did not inhibit AR response reporter;
(**) n/a: the compound was not examined in this assay.

We examined the antagonistic activity of the compounds for which the synthesis is described above in the presence of 100 pM of R1881. Engineered LNCaP cells (LNCaP-AR, also abbreviated LN-AR) were maintained in Iscove's medium containing 10% fetal bovine serum (FBS). Two days prior to drug treatment, the cells were grown in Iscove's medium containing 10% charcoal-stripped FBS (CS-FBS) to deprive of androgens. The cells were split and grown in Iscove's medium containing 10% CS-FBS with 100 pM of R1881 and increasing concentrations of test compounds. After two days of incubation, reporter activities were assayed.

Table 1 lists the IC50 of these compounds to inhibit AR in hormone refractory prostate cancer. The control substance bicalutamide has an IC50 of 889 nM. Most of the compounds identified (diarylthiohydantoins) have IC50s between 100 to 200 nM in inhibiting AR in hormone refractory prostate cancer. In contrast, antiandrogenic compounds listed as examples in U.S. Pat. No. 5,705,654, such as examples 30-2, 30-3, 31-2, 31-3, and 24-3 (NC24-NC28) have no inhibitory activities on AR in this system.

TABLE 2

Agonistic activities of selective test substances on AR response reporter in hormone refractory prostate cancer

| Example | Name | Fold induction by increasing concentrations of compounds | | |
|---|---|---|---|---|
| | | 0.1 μM | 1 μM | 10 μM |
| DMSO | Dimethyl sulfoxide | 1.00 (*) | 1.00 | 1.00 |
| R1881 | methyltrienolone | 44.33 | n/a (**) | n/a |
| Bicalutamide | N-[4-cyano-3-(trifluoromethyl)phenyl]-3-[(4-fluorophenyl)sulfonyl]-2-hydroxy-2-methylpropanamide | 1.66 | 3.04 | 10.40 |
| 29 Comp. | 4-[3-(4-hydroxybutyl)-4,4-dimethyl-5-oxo-2-thioxoimidazolidin-1-yl]-2-trifluoromethylbenzonitrile | 10.99 | 20.84 | 34.62 |
| 7-3b (7c) [NC7] | 4-(8-oxo-6-thioxo-5-(4-methylphenyl)-5,7-diazaspiro[3.4]oct-7-yl)-2-trifluoromethylbenzonitrile | 0.87 | 1.19 | 0.89 |
| 33 (33a) [NC34] | 1-[3-(4-cyano-3-trifluoromethyl-phenyl)-5,5-dimethyl-2-thioxo-1-p-tolyl-imidazolidin-4-ylidene]-3-ethyl-thiourea | 1.30 | 1.18 | 1.28 |
| 34 (34a) [NC35] | 1-[7-(4-cyano-3-trifluoromethyl-phenyl)-6-thioxo-5-p-tolyl-5,7-diaza-spiro[3.4]oct-8-ylidene]-3-phenyl-thiourea | 1.19 | 1.41 | 1.17 |
| 35 (35a) [NC36] | 1-(4-Cyano-3-trifluoromethyl-phenyl)-3-[7-(4-cyano-3-trifluoromethyl-phenyl)-6-thioxo-5-p-tolyl-5,7-diaza-spiro[3.4]oct-8-ylidene]-thiourea | 1.26 | 1.10 | 1.30 |
| 30-2 Comp. (30b) [NC24] | 4-(5-methyl-8-oxo-6-thioxo-5,7-diazaspiro[3.4]oct-7-yl)-2-trifluoromethylenzonitrile | 14.88 | 19.41 | 35.22 |

TABLE 2-continued

Agonistic activities of selective test substances on AR response
reporter in hormone refractory prostate cancer

| Example | Name | Fold induction by increasing concentrations of compounds | | |
|---|---|---|---|---|
| | | 0.1 µM | 1 µM | 10 µM |
| 30-3 Comp. (30c) [NC25] | 4-(5-methyl-6,8-dioxo-5,7-diazaspiro[3.4]oct-7-yl)-2-trifluoromethylbenzonitrile | 11.39 | 14.26 | 30.63 |
| 31-2 Comp. (31b) [NC27] | 4-(1-methyl-4-oxo-2-thioxo-1,3-diazaspiro[4.4]non-3-yl)-2-trifluoromethylbenzonitrile | 17.03 | 16.63 | 33.77 |
| 31-3 Comp. (31c) [NC27] | 4-(1-methyl-2,4-dioxo-1,3-diaza-spiro[4.4]non-3-yl)-2-trifluoromethylbenzonitrile | 11.99 | 19.77 | 38.95 |
| 24-3 Comp. (24c) [NC28] | 4-(4-oxo-2-thioxo-1,3-diazaspiro[4.4]non-3-yl)-2-trifluoromethylbenzonitrile | 14.88 | 22.48 | 37.09 |

(*) Fold induction: activities induced by a specific test substance over activities in DMSO vehicle;
(**) n/a: the compound was not examined in this assay.

One previously unrecognized property of AR overexpression in hormone refractory prostate cancer is its ability to switch antagonists to agonists. Therefore, only those compounds with minimal or no agonistic activities are qualified to be anti-androgens for this disease. To determine agonistic activities of different compounds, we examined their stimulating activities on AR using the AR response reporter as the measure in the LN-AR system in the absence of R1881. Table 2 lists the agonistic activities of different compounds. Consistent with previous results, bicalutamide activated AR in hormone refractory prostate cancer. The diarylthiohydantoin derivatives such as examples 7-3b (NC7), 33 (NC34), 34 (NC35), and 35 (NC36) have no agonistic activity. In contrast, RU59063, and other anti-androgenic compounds listed as examples in U.S. Pat. No. 5,705,654, such as examples 30-2, 30-3, 31-2, 31-3, and 24-3 (NC24-NC28) strongly activated AR in hormone refractory prostate cancer.

To examine the specificity of AR inhibitors, selective compounds were tested in LNCaP cells with an over expression of glucocorticoid receptor (GR), the closest member of AR in the nuclear receptor family. These cells also carry a GR response reporter and the reporter activity was induced by dexamethasone, a GR agonist and the induction was blocked by RU486, a GR inhibitor. Example 7-3b (NC7) (4-(8-oxo-6-thioxo-5-(4-methylphenyl)-5,7-diazaspiro[3.4]oct-7-yl)-2-trifluoromethyl benzonitrile) had no effect on GR in this system.

Effect of Compounds on AR by Measuring Secreted
Levels of Prostate Specific Antigen (PSA)

It is well established that PSA levels are indicators of AR activities in prostate cancer. To examine if the compounds affect AR function in a physiological environment, we determined secreted levels of endogenous PSA induced by R1881 in the AR-overexpressed LNCaP cells (LNCaP-AR, also abbreviated LN-AR). The LNCaP-AR cells are a line of lymph node carcinoma of prostate cells transduced with a plasmid that makes express androgen receptors. LNCaP-AR cells were maintained in Iscove's medium containing 10% FBS. Two days prior to drug treatment, the cells were grown in Iscove's medium containing 10% CS-FBS to deprive of androgens. The cells were split and grown in Iscove's medium containing 10% CS-FBS with appropriate concentrations of R1881 and the test compounds. After four days incubation, secreted PSA levels were assayed using PSA ELISA kits (American Qualex, San Clemente, Calif.)

The secreted PSA level of LNCaP-AR cells was strongly induced by 25 pM of R1881. In contrast, PSA was not induced in the parental LNCaP cells until concentration of R1881 reached 100 pM. This is consistent with our previous report that the AR in hormone refractory prostate cancer is hyper-sensitive to androgens. A dose-dependent inhibition on AR activity was carried out to determine the IC50s of different compounds in inhibiting PSA expression, and the results were listed in Table 1. IC50s of the selective compounds on PSA expression closely resemble those measured by the reporter assay, confirming that the diarylhydantoin derivatives are strong inhibitors of AR in hormone refractory prostate cancer.

We also examined agonistic activities of selective compounds on AR in hormone refractory prostate cancer using secreted PSA as the surrogate marker. To do this, androgen-starved AR over expressed LNCaP cells were incubated with increasing concentrations of the compounds for which a synthesis is described above in the absence of R1881 and secreted PSA in the culture medium was measured 4 days later.

Table 3 lists the agonistic activities of the selective compounds. Consistent with the results obtained from the reporter assay, the diarylthiohydantoin derivatives such as examples 7-3b (NC7), 33 (NC34), 34 (NC35), and 35 (NC36) have no agonistic activities. In contrast, RU59063, and other antiandrogenic compounds listed as examples in U.S. Pat. No. 5,705,654, such as examples 30-2 (NC24), 30-3 (NC25), and 31-2 (NC26) stimulated PSA expression in hormone refractory prostate cancer.

TABLE 3

Agonistic activities of selective test substances on
endogenous PSA in hormone refractory prostate cancer
Fold induction by increasing concentrations of compounds

| Example | Name | 0.1 µM | 1 µM | 10 µM |
|---|---|---|---|---|
| DMSO | Dimethyl sulfoxide | 1.00 (*) | 1.00 | 1.00 |
| R1881 | methyltrienolone | 20.69 | n/a (**) | n/a |
| Bicalutamide | N-[4-cyano-3-(trifluoromethyl)phenyl]-3-[(4-fluorophenyl)sulfonyl]-2-hydroxy-2-methylpropanamide | 2.00 | 2.55 | 5.55 |
| 29 Comp. | 4-[3-(4-hydroxybutyl)-4,4-dimethyl-5-oxo-2-thioxoimidazolidin-1-yl]-2-trifluoromethylbenzonitrile | 6.88 | 11.50 | 21.50 |
| 7-3b (7c) [NC7] | 4-(8-oxo-6-thioxo-5-(4-methylphenyl)-5,7-diazaspiro[3.4]oct-7-yl)-2-trifluoromethylbenzonitrile | 1.25 | 1.20 | 1.15 |
| 33 (33a) [NC34] | 1-[3-(4-cyano-3-trifluoromethyl-phenyl)-5,5-dimethyl-2-thioxo-1-p-tolyl-imidazolidin-4-ylidene]-3-ethyl-thiourea | 1.06 | 1.30 | 0.85 |
| 34 (34a) [NC35] | 1-[7-(4-cyano-3-trifluoromethyl-phenyl)-6-thioxo-5-p-tolyl-5,7-diaza-spiro[3.4]oct-8-ylidene]-3-phenyl-thiourea | 1.31 | 1.05 | 0.90 |
| 35 (35a) [NC36] | 1-(4-Cyano-3-trifluoromethyl-phenyl)-[7-(4-cyano-3-trifluoromethyl-phenyl)-6-thioxo-5-p-tolyl-5,7-diaza-spiro[3.4]oct-8-ylidene]-thiourea | 1.44 | 1.30 | 1.05 |
| 30-2 Comp. (30b) [NC24] | 4-(5-methyl-8-oxo-6-thioxo-5,7-diazaspiro[3.4]oct-7-yl)-2-trifluoromethylenzonitrile | 6.25 | 17.95 | 25.65 |
| 30-3 Comp. (30c) [NC25] | 4-(5-methyl-6,8-dioxo-5,7-diazaspiro[3.4]oct-7-yl)-2-trifluoromethylbenzonitrile | 7.50 | 15.20 | 23.75 |
| 31-2 Comp. (31b) [NC26] | 4-(1-methyl-4-oxo-2-thioxo-1,3-diazaspiro[4.4]non-3-yl)-2-trifluoromethylbenzonitrile | 8.13 | 18.20 | 17.50 |

(*) Fold induction: activities induced by a specific test substance over activities in DMSO vehicle;
(**) n/a: the compound was not examined in this assay.

Effect of Compounds on AR Mitochondrial Activity
by MTS Assay

LNCaP-AR cells were maintained in Iscove's medium containing 10% FBS. The compounds were examined for their effect on growth of hormone refractory prostate cancer cells. Overexpressed LNCaP cells were used because these cells behave as hormone refractory prostate cancer cells in vitro and in vivo (1). We measured mitochondria activity by MTS assay, a surrogate for growth. LNCaP cells with overexpressed AR (LN-AR) were maintained in Iscove's medium containing 10% FBS. Two days prior to drug treatment, the cells were grown in Iscove's medium containing 10% CS-FBS to deprive of androgens. The cells were then split and grown in Iscove's medium containing 10% CS-FBS with appropriate concentrations of R1881 and increasing concentrations of the test compounds. After four days incubation, cell growth was monitored by MTS (Promega, Madison, Wis.).

Consistent with the reporter assay and PSA assay, growth of the AR-overexpressed LNCaP was stimulated by 25 microM of R1881, but the parental cells were not stimulated until R1881 concentration reached 100 microM. FIG. 2 shows the inhibitory effect of selected compounds on growth of hormone refractory prostate cancer in the presence of 100 pM of R1881. The current clinical drug bicalutamide did not inhibit hormone refractory prostate cancer. In contrast, example 5-3b (NC2) (4-[3-(4-methylphenyl)-4,4-dimethyl-5-oxo-2-thioxoimidazolidin-1-yl]-2-trifluoromethyl-benzonitrile) and example 7-3b (NC7) (4-(8-oxo-6-thioxo-5-(4-methylphenyl)-5,7-diazaspiro[3.4]oct-7-yl)-2-trifluoromethylbenzonitrile) inhibited hormone refractory prostate cancer with high potency.

We examined if growth inhibition in the MTS assay occurs by targeting AR, example 5-3b (NC2) (4-[3-(4-methylphenyl)-4,4-dimethyl-5-oxo-2-thioxoimidazolidin-1-yl]-2-trifluoromethyl-benzonitrile) and example 7-3b (NC7) (4-(8-oxo-6-thioxo-5-(4-methylphenyl)-5,7-diazaspiro[3.4]oct-7-yl)-2-trifluoromethylbenzonitrile) were tested in DU-145 cells, a prostate cancer cell line that lacks AR expression. These compounds had no growth inhibitory effect on DU-145 cells. The compounds did not inhibit cells other than AR-expressed prostate cancer cells, as they had no growth effect on MCF7 and SkBr3, two commonly used breast cancer cells, or 3T3, a normal mouse fibroblast cell line.

Figure 3:
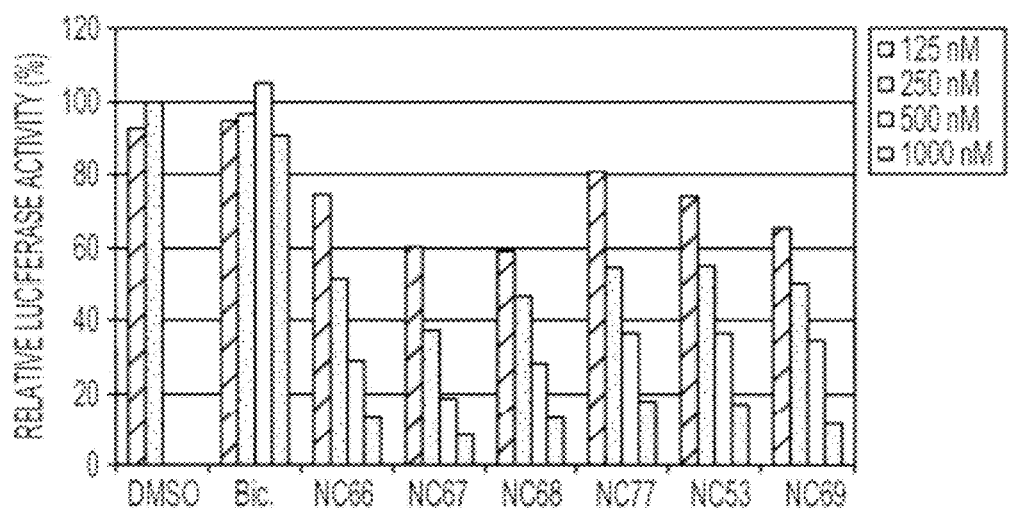
FIG. 3 is a graph depicting the effect of compounds on LNCaP-AR.
Figure 4:
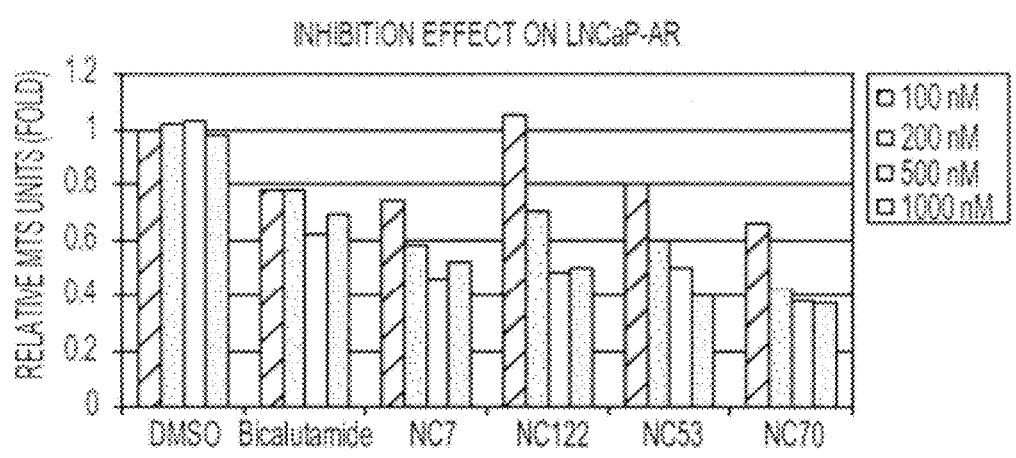
FIG. 4 is a graph depicting the inhibition effect on LNCaP-AR.
Figure 5:
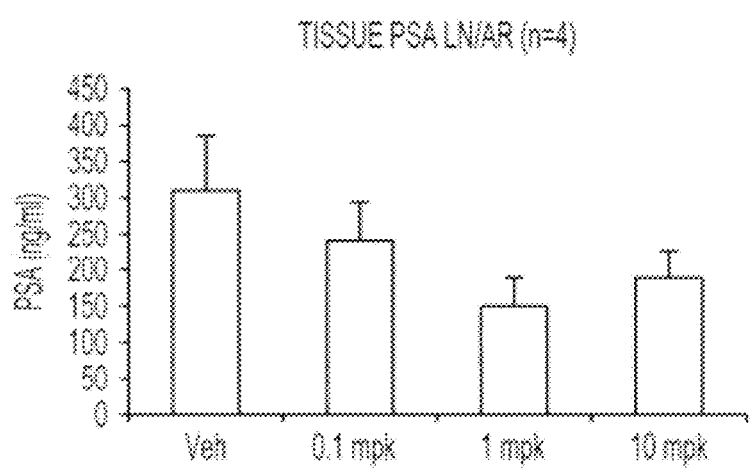
FIG. 5. Inhibitory effect on PSA expression of AR-overexpressed LNCaP xenograft model. Mice were treated with vehicle, 0.1, 1, or 10 mg per kg of example 7-3b (NC7) for 44 days orally once daily. The tumors were taken out from the mice after 44 days of treatment, tumor lysate was extracted, and PSA level in tissue lysate was determined by ELISA.

Examples of in vitro biological activity of diarylthiohydantoin derivatives are shown in the FIGS. 3 and 4. For example, based on relative luciferase activity, FIG. 3 indicates that at a concentration of 500 nM the compounds ranked, in order of most active to least active as follows: NC67>NC68>NC66>NC69>NC77=NC53>bicalutamide. For example, based on relative PSA level, it was found that at a concentration of 500 nM the compounds ranked, in order of most active to least active as follows: NC50> NC48>NC7>NC43>NC44>NC49>NC50>NC45> bicalutamide. For example, based on relative MTS units, FIG. 4 indicates that at a concentration of 500 nM the compounds ranked, in order of most active to least active as follows: NC70>NC7>NC 122>NC53>bicalutamide.

Inhibitory Effect on Hormone Refractory and Hormone Sensitive Prostate Cancer Xenograft Tumors Compounds of the invention are used to examine if the diaryihydantoin derivatives have in vivo effects on hormone refractory prostate cancer. First we examine this compound on xenograft tumors established from AR-overexpressed LNCaP cells. Engineered cells in Matrigel (Collaborative Biomedical) are injected subcutaneously into the flanks of the castrated male SCID mice. Tumor size is measured weekly in three dimensions using calipers. After xenograft tumors established (tumor size at least 40 mm$^3$), mice with tumors are randomized and treated with different doses of compounds orally once daily. The inhibitory effect on growth of AR-overexpressed LNCaP xenograft model is studied as follows. Mice with established LN-AR xenograft tumors are randomized and treated with indicated compounds orally once daily. Tumor size are measured by caliber.

Consistent with clinical observation, current clinical drug bicalutamide did not inhibit growth of hormone refractory prostate cancer (same as vehicle). In contrast, compounds according to the invention inhibit growth of these tumors and the inhibition is dose-dependent. Furthermore, the compounds inhibit PSA expression, the clinical marker for hormone refractory prostate cancer.

Compounds of the invention are also tested in another xenograft model of hormone refractory prostate cancer, hormone refractory LAPC4. This model was established from passaging of hormone sensitive prostate cancer in castrated mice, which mimics the clinical progression of prostate cancer (2). Similar to the finding using AR-overexpressed LNCaP xenograft model, current clinical drug bicalutamide did not inhibit growth and PSA expression in hormone refractory LAPC4 xenograft model (same as vehicle). In contrast, compounds of the invention inhibited growth and PSA expression of these tumors.

Figure 6:
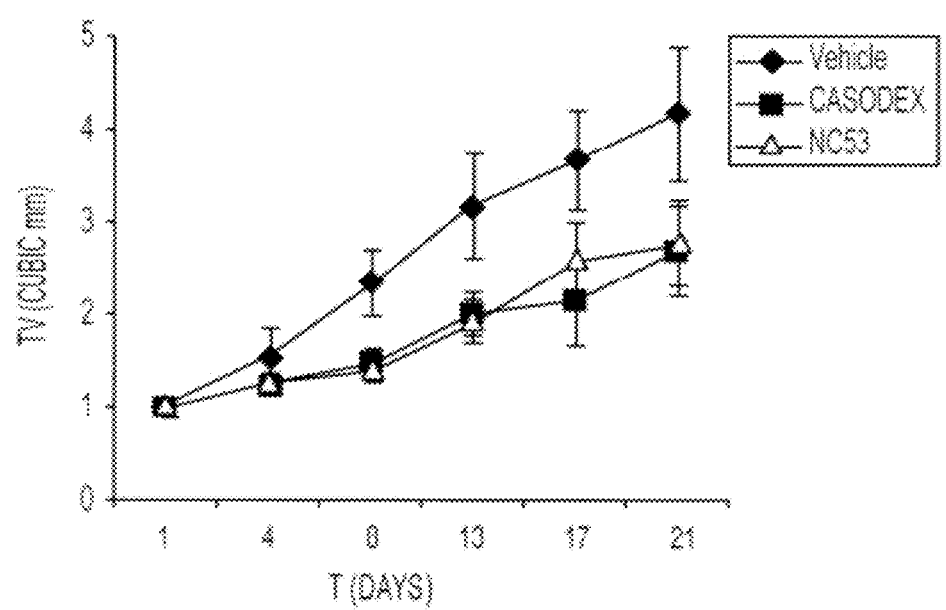
FIG. 6 is a graph of tumor volume as a function of time for treatment with vehicle solution, Casodex, and NC53.

FIG. 6 presents the results of an experiment in which cells from the LNCaP hormone sensitive model were xenografted into mice ($10^6$ cells of LNCaP were injected into mice). A first set of mice was treated with NC53, a second set of mice was treated with Casodex, and a third set of mice was treated with vehicle solution. Each set included 6 mice. The mice were treated with 10 mg/kg per day. FIG. 6 presents the results as a graph of tumor volume as a function of time. Mice treated with vehicle solution as a control exhibited the most rapid increase in tumor volume. Mice treated with Casodex and mice treated with NC53 exhibited similar rates of tumor growth, slower than mice treated with vehicle solution.

Inhibitory Effect on Growth of Hormone Sensitive Prostate Cancer Cells

To determine if the diarylthiahydantoin derivatives also inhibit hormone sensitive prostate cancer cells, we test some selective compounds on growth of LNCaP cells by measuring MTS of mitochondria activities. Androgen starved LNCaP cells are treated with increasing concentrations of DMSO as vehicle or test substances in the presence of 1 pM of R1881. After 4 days of incubation, cell growth is measured by MTS assay. Compounds of the invention inhibit hormone sensitive prostate cancer with a higher potency than bicalutamide.

In Vivo Biological Assay

Figure 7:
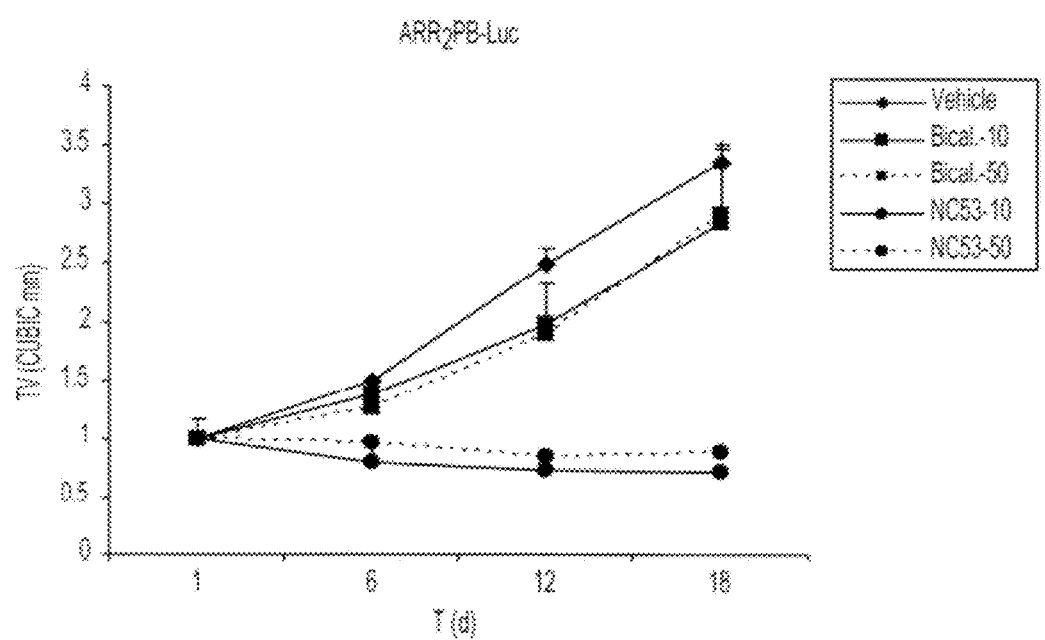
FIG. 7 is a graph of tumor size. AR overexpressing LNCaP cells were injected in the flanks of castrated SCID mice, subcutaneously. When tumors reached about 100 cubic mm, they were randomized into five groups. Each group had nine animals. After they reached this tumor volume, they were given orally with either vehicle, bicalutamide or NC53 at 10 or 50 mg/kg everyday. The tumors were measured three-dimensionally, width, length and depth, using a caliper.
Figure 8C:
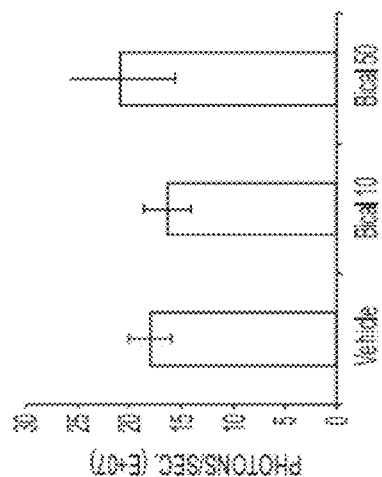
FIG. 8 depicts experimental results of tumor size. At day 18, the animals were imaged via an optical CCD camera, 3 hours after last dose of treatment. A ROI was drawn over the tumor for luciferase activity measurement in photon/second. The right panels is a representation of the ROIs measurements.
Figure 8D:
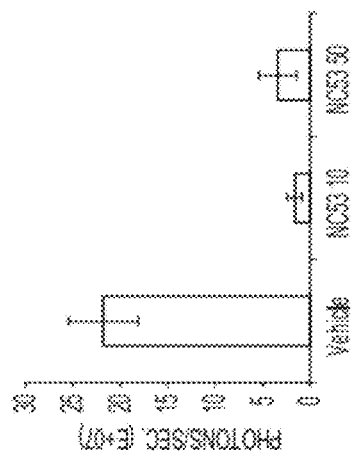
Figure 8A:
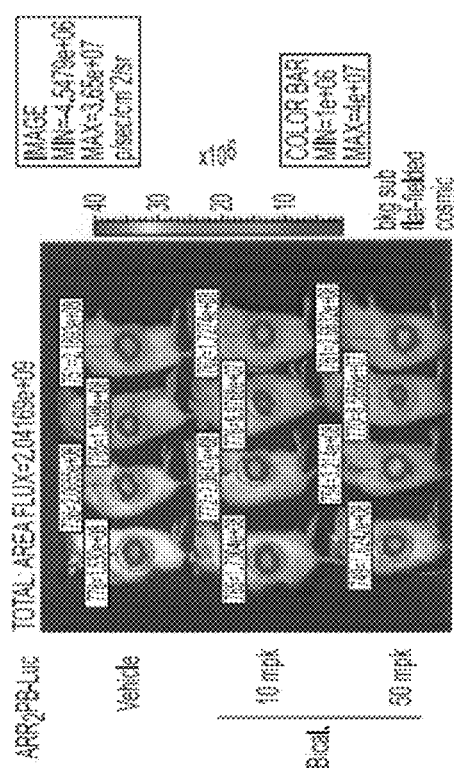
Figure 8B:
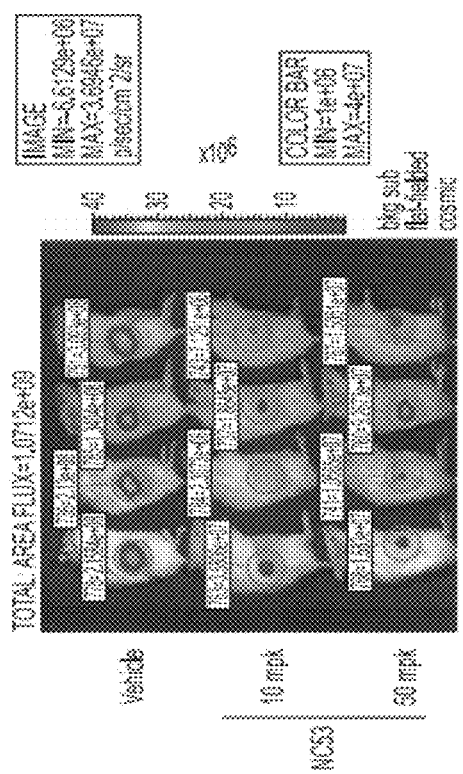

All animal experiments were performed in compliance with the guidelines of the Animal Research Committee of the University of California at Los Angeles. Animals were bought from Taconic and maintained in a laminar flow tower in a defined flora colony. LNCaP-AR and LNCaP-vector cells were maintained in RPMI medium supplemented with 10% FBS. $10^6$ cells in 100 µl of 1:1 Matrigel to RPMI medium were injected subcutaneously into the flanks of intact or castrated male SCID mice. Tumor size was measured weekly in three dimensions (length×width×depth) using calipers. Mice were randomized to treatment groups when tumor size reached approximately 100 mm$^3$. Drugs were given orally every day at 10 mg/kg and 50 mg/kg. To obtain pharmacodynamic readout, the animals were imaged via an optical CCD camera, 3 hours after last dose of the treatment. A ROI is drawn over the tumor for luciferase activity measurement in photon/second. The right panels were a representation of the ROIs measurements. Data are shown in FIGS. 7 and 8. Over 18 days NC53 was effective to prevent tumor growth and even to cause tumor shrinkage, and was distinctly more effective than bicalutamide.

The pharmacokinetics of bicalutamide, 4-[7-(4-cyano-3-trifluoromethylphenyl)-8-oxo-6-thioxo-5,7-diaza-spiro[3.4]oct-5-yl]-toluene[NC7], N-methyl-4-{4-[7-(4-cyano-3-trifluoromethylphenyl)-8-oxo-6-thioxo-5,7-diaza-spiro[3.4]oct-5-yl]phenyl}butanamide[NC48], and N-methyl-4-[7-(4-cyano-3-trifluoromethylphenyl)-8-oxo-6-thioxo-5,7-diaza-spiro[3.4]oct-5-yl]-2-fluorobenzamide (52d) [NC53] were evaluated in vivo using 8 week-old FVB mice which were purchased from Charles River Laboratories. Mice were divided into groups of three for each time points. Two mice were not treated with drug and two other mice were treated with vehicle solution. Each group was treated with 10 mg per kilogram of body weight.

The drug was dissolved in a mixture 1:5:14 of DMSO:PEG400:H$_2$0. (Vehicle solution) and was administered into mice through the tail vein. The animals are warmed under a heat lamp for approximately 20 minutes prior to treatment to dilate their tail vein. Each mouse was placed into a mouse restrainer (Fisher Sci. Cat #01-288-32A) and was injected with 200 µl of drug in vehicle solution into the dilated tail vein. After drug administration, the animals were euthanized via CO$_2$ inhalation at different timepoints: 5 nm, 30 nm, 2 h, 6 h, 16 h. Animals were immediately bleed after exposure to CO$_2$ via cardiac puncture (1 ml BD syringe+27 G ⅝ needle). For oral dosage, the drug was dissolved in a mixture 50:10:1:989 of DMSO:Carboxymethylcellulose:Tween80:H20 before oral administration via a feeding syringe.

The serum samples were analyzed to determine the drug's concentration by the HPLC which (Waters 600 pump, Waters 600 controller and Waters 2487 detector) was equipped with an Alltima C18 column (3µ, 150 mm×4.6 mm). The NC7, NC48, and NC53 compounds were detected at 254 nm wave length and bicalutamide was detected at 270 nm wave length.

The samples for HPLC analysis were prepared according to the following procedure:

Blood cells were separated from serum by centrifugation.

To 400 µl of serum were added 80 µl of a 10 µM solution of an internal standard and 520 µl of acetonitrile. Precipitation occurred.

The mixture was vortexed for 3 minutes and then placed under ultrasound for 30 minutes.

The solid particles were filtered off or were separated by centrifugation.

The filtrate was dried under an argon flow to dryness. The sample was reconstructed to 80 μl with acetonitrile before analyzing by HPLC to determine the drug concentration.

Standard curve of drug was used to improve accuracy.

Figure 9:
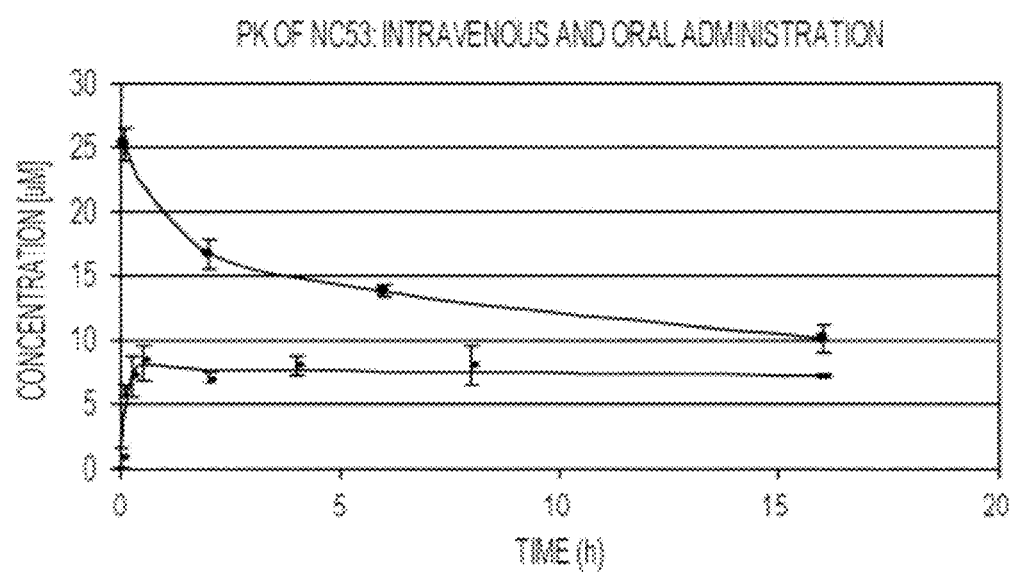
FIG. 9 is a graph depicting the pharmacokinetic curves of NC53 from intravenous (upper curve) and oral administration (lower curve).

The concentration of NC53 in plasma as a function of time resulting from intravenous and from oral administration is shown in FIG. 9. The steady state concentration (Css) of bicalutamide, NC48, and NC53 is shown in Table 4. The concentration at steady state of NC53 is essentially as good as that of bicalutamide, and substantially better than NC48.

TABLE 4

Steady-state concentration of bicalutamide, NC48, and NC53 in mice plasma.

| Name | IC50 [nM] | LogP | Css, 10 mg/kg [μM] | Css, 25 mg/kg [μM] | Css, 50 mg/kg [μM] |
|---|---|---|---|---|---|
| Bic. | 1000 | 2.91 | 10.0 | 11.4 | 11.9 |
| NC48 | 92 | 3.44 | 0.39 | 0.43 | 0.40 |
| NC53 | 122 | 3.20 | 9.9 | 10.7 | 10.2 |

The androgen receptor activity can encompass several aspects of stimulation and of inhibition of androgen receptor behavior, including, but not limited to, the following: inhibitory concentration (IC50) in an AR response reporter system or a prostate specific antigen secreting system; fold induction associated with increasing concentrations in an AR response reporter system or a prostate specific antigen secreting system; associated tumor growth in an animal; the binding affinity of an androgen receptor to a compound; androgen receptor recruitment to a prostate specific antigen enhancer or a prostate specific antigen promoter; androgen receptor nuclear translocation; and destabilization of an androgen receptor protein.

In Vitro Assays

Figure 10:
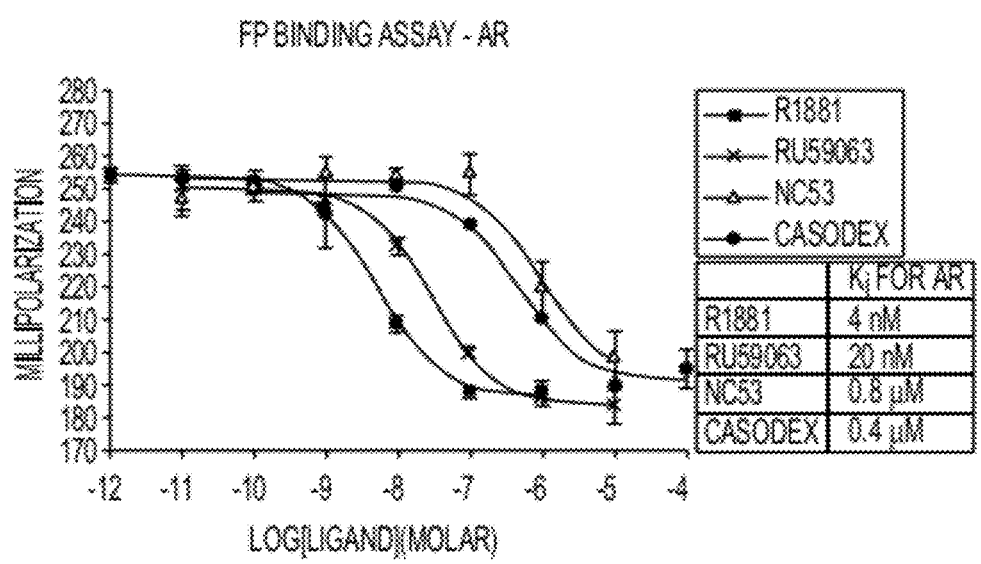
FIG. 10 is a graph of fluorescence absorbance as a function of the logarithm of concentration, which reflects the binding affinities of several compounds to rat androgen receptor.

FIG. 10 presents the relative binding affinities of compounds for the ligand binding domains of rat androgen receptor (rat AR) as determined with competitor assay kits (Invitrogen). Fluorescence polarization was used as a read-out. Each hormone dose was performed in triplicate and the relative error was determined by calculating the standard error of the three values from the mean. The study controlled for minimal competition (vehicle alone), no receptor, no fluorescent ligand, and maximal competition ($10^{-5}$ M R1881, progesterone, E2 or dexamethasone). The curves were fit using a single binding site competition model (the Prism statistical analysis software package was used. R1881 had the lowest equilibrium dissociation constant, Ki=4 nM (and thus the rat androgen receptor had the highest affinity for R1881 of the four compounds tested). RU59063 had an equilibrium dissociation constant of Ki=20 nM, and NC53 had an equilibrium dissociation constant of Ki=0.8 uM. Casodex had an equilibrium dissociation constant of Ki=0.4 uM (and thus the rat androgen receptor had the lowest affinity for Casodex of the four compounds tested). NC53 and Casodex had similar equilibrium dissociation constants, and, thus, rat androgen receptor had a similar affinity for these compounds.

Figure 11:
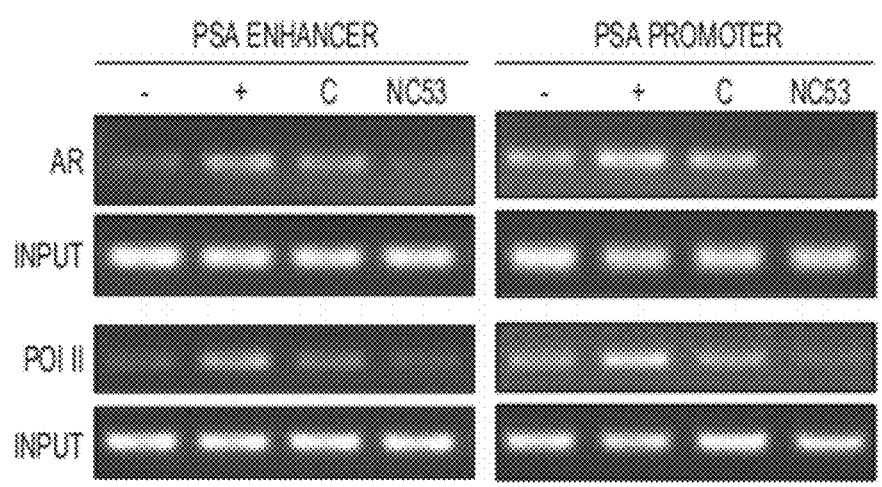
FIG. 11 presents images reflecting the state of complexation of androgen receptor and RNA polymerase II to PSA enhancer and to PSA promoter when Casodex or NC53 are added.

NC53 prevented androgen receptor (AR) recruitment and RNA polymerase II (Pol II) recruitment to PSA enhancer and to PSA promoter. FIG. 11 presents the results of the study. Materials used were Chromatin IP with AR (Upstate, cat #06-680) and Pol II (Covance, cat #MMS-126R). LNCaP (ATCC) cells were plated in full serum. On the day of the experiment, the plate was washed once with 1×PBS and 5% CSS was added for 3 days. For a first set of experiments 10 uM of NC53 was added (R), for a second set of experiments 10 uM of bicalutamide (C) was added, and for a third set of experiments 1 nM of R1881 was added (+). Each of these compounds was added for 6 hours. In a fourth set of experiments, a control, no additional compound was added (−). 6 hours timepoint was run at 28 cycles. ChIP kits from Upstate (cat #17-295) were used. Enhancer and promoter primers were obtained from Louie (PNAS 2003 Vol. 100, pp. 2226-2230) and Shang (Molecular Cell 2002 vol. 9, pp. 601-610), respectively. The darker image for experiments in which NC53 (R) was added indicated that NC53 prevented androgen receptor and prevented RNA polymerase II from forming a transcription complex on the prostate specific antigen (PSA) gene. By contrast, the lighter image for experiments in which bicalutamide (Casodex, C) was added indicated that in the presence of bicalutamide androgen receptor and RNA polymerase II were still recruited to the PSA elements to transcribe PSA mRNA.

Figure 12:
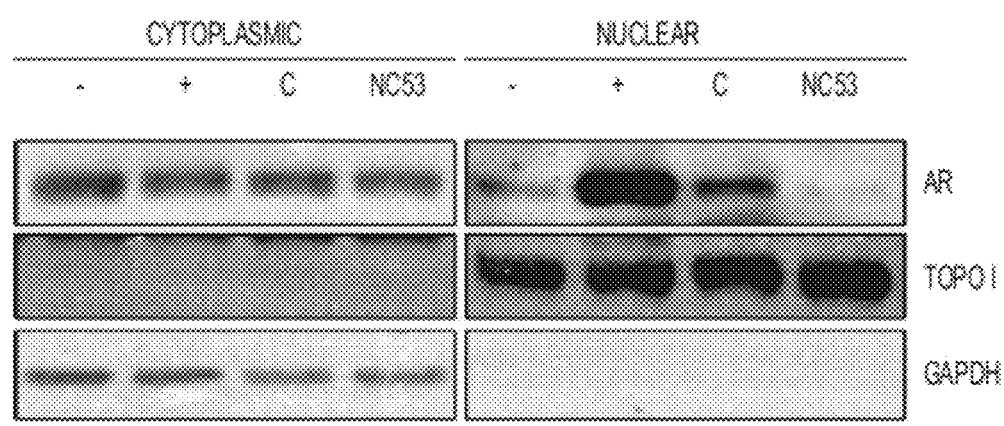
FIG. 12 presents images reflecting that androgen receptor translocates into the nucleus in the presence of Casodex, but not in the presence of NC53.
Figure 13:
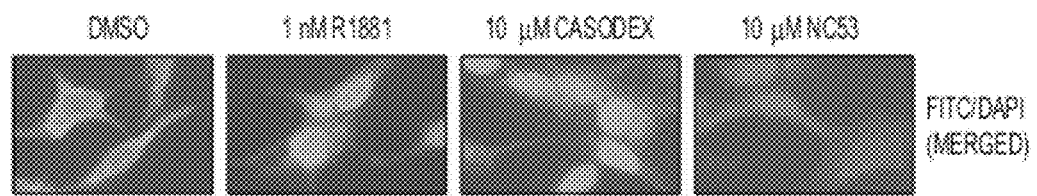
FIG. 13 presents images reflecting that androgen receptor translocates into the nucleus in the presence of Casodex, but not in the presence of NC53.

NC53 inhibited androgen receptor nuclear translocation in LNCaP cells. FIGS. 12 and 13 present the results of the study. LNCaP cells were plated in 5% CSS. A first set of cells was treated with 10 uM NC53 (R), a second set of cells was treated with 10 uM bicalutamide (C), and a third set of cells was treated with 1 nM R1881 (+). A fourth set of cells served as a control (−). TOPO I (Santa Cruz, cat #sc-32736) was used to control for nuclear fraction, and GAPDH (Santa Cruz, cat #sc-20357) was used to control for cytoplasmic fraction. LNCaP cells were harvested for subcellular fractionation or stained with a FITC (Santa Cruz) labeled antibody against androgen receptor (AR) (Santa Cruz, cat #sc-815). From the subcellular fractionation, images were obtained, as shown in FIG. 12. The darker image in the nuclear fraction for the bicalutamide (Casodex, C) treated sample indicated that bicalutamide induced androgen receptor nuclear translocation. The light image for the NC53 (R) treated sample indicated that NC53 abrogated nuclear translocation. For the AR-FITC assay, cover slips were mounted on glass slides using DAPI-containing medium, and cells were imaged 24 hours later using a fluorescence Nikon microscope at X60 with filters for DAPI and FITC. In the AR-FITC assay, the nuclei of the R1881 and of the bicalutamide treated cells were distinctly green, as shown in FIG. 13 indicating that nuclear translocation of the androgen receptor occurred. By contrast, the nuclei of the DMSO and of the NC53 treated cells were less green.

Figure 14:
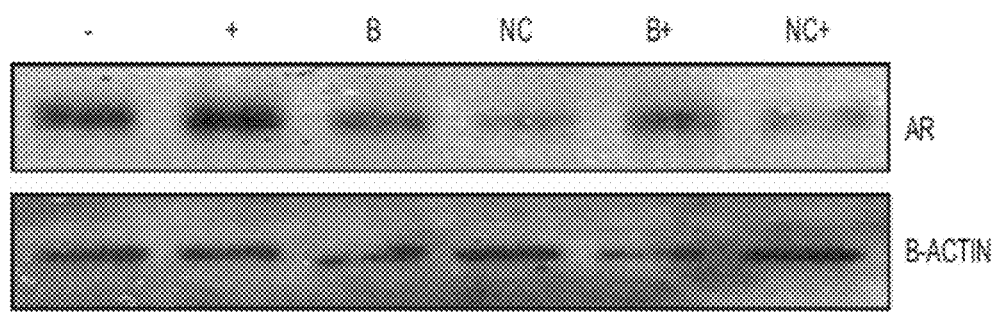
FIG. 14 presents images reflecting that androgen receptor protein is degraded in the presence of NC53.
Figure 15:
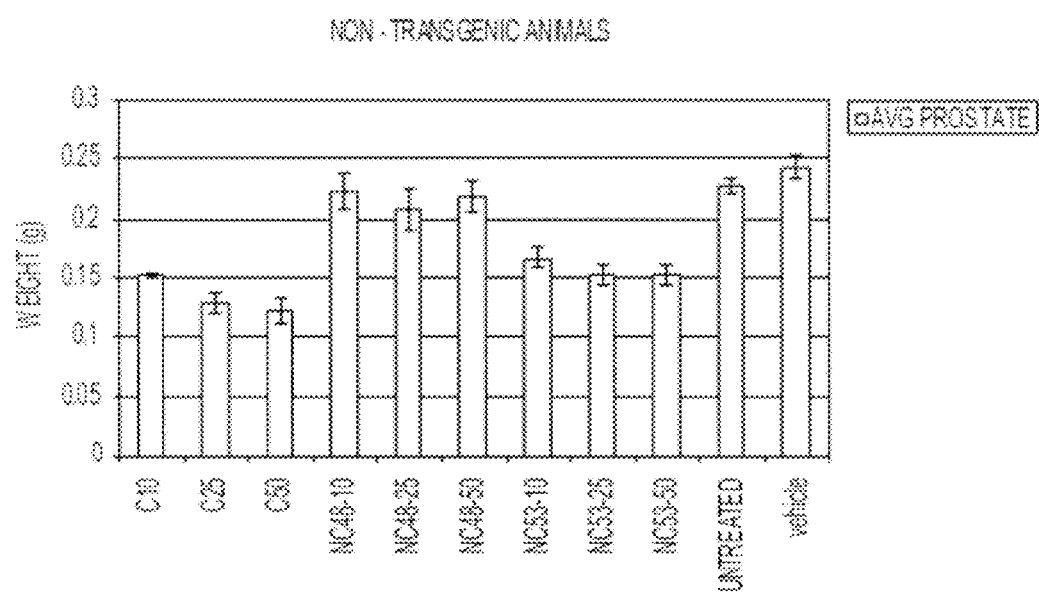
FIG. 15 is a chart depicting prostate weight after treatment with various compounds. 10, 25, or 50 mg of compound per kilogram body weight were administered per day, as indicated by the label of a bar. The compounds were administered to healthy FVB mice. After treatment with compound for 14 days, the urogenital tract weight was determined by removing and weighing the semi-vesicles, prostate, and bladder. Three mice were administered a given compound to obtain the data presented by a bar in the chart. A set of mice was not treated with a compound: data are presented in the bar labeled "untreated". Another set of mice was treated only with vehicle solution: data are presented in the bar labeled "vehicle".

NC53 destabilized androgen receptor proteins in LNCaP cells. FIG. 14 shows the results of the study. The study was conducted by plating $10^5$ LNCaP (fgc) cells in 5% CSS for 3 days. 100 pM of R1881 was added to a first set of cells (+), 10 uM of bicalutamide was added to a second set of cells (B), 10 uM of NC53 was added to a third set of cells (RD), 100 pM of R1881 and 10 uM of bicalutamide was added to a fourth set of cells (B+), and 100 pM of R1881 and 10 uM of NC53 was added to a fifth set of cells (RD+). Neither R1881, bicalutamide, nor NC53 was added to a sixth set of cells (−). The cells were allowed to reside with the added bicalutamide, NC53, and/or R1881 for 24 hours (or in the case of the (−) set, without any of these for 24 hours). In FIG. 14, the dark image for the set to which bicalutamide (B) was added and for the set to which bicalutamide and R1881 (B+) were added indicated that the androgen receptor protein was level when these combinations of compounds were added. By contrast, the light image for the set to which NC53 (RD) was added and for the set to which NC53 and R1881 (RD+) were added indicated that the addition of NC53 resulted in the degradation of androgen receptor proteins, whether or not R1881 was present.

Ranking of Compounds in Tiers

Tables 5-10 present diarylhydantoin compounds grouped into Tiers 1-6. Table 11 presents diarylhydantoin compounds which have not been placed into a tier. The placement of compounds into tiers was based on available data coupled with analytical judgment. Data considered included in vitro assays (AR response reporter system in LNCaP cell line, PSA level measurement, MTS mitochondrial assay) and in vivo experiments (tumor size measured directly or by emission induced by luciferase reporter gene, pharmacokinetic assays based on blood plasma levels). Not every compound was subjected to each assay. Not all data that was generated is shown. Judgment was applied in ranking compounds relative to each other for their utility in treating prostate cancer, in particular when ranking two compounds for which the same experiments were not performed. Characteristics considered in establishing the ranking include AR antagonism activity, lack of AR agonism in hormone refractory cells, prevention of tumor growth, tumor shrinkage, and pharmacokinetic behavior, with a longer residence time in blood being advantageous.

Tier 1

Generally, Tier 1 compounds are diarylthiohydantoins with a disubstituted left hand aryl ring that are disubstituted on the right hydantoin carbon, and have either an oxygen or N substituent on the left hydantoin carbon. It is expected that the amido substituent hydrolyzes to an oxygen in aqueous solutions such as encountered in biological systems, in vitro and in vivo. NC63 has good activity with an iodine instead of a $CF_3$ substituent on the left hand aryl ring.

Tier 1 compounds (see Table 5) were judged to be much better than bicalutamide for treating prostate cancer. However, NC7 and NC48 were found to metabolize fast, that is, have a short residence time in blood. NC53 had desirable pharmacokinetics.

Figure 16:
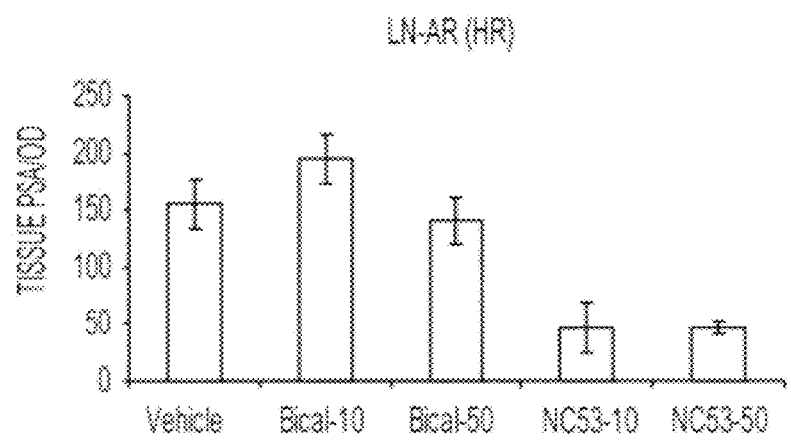
FIG. 16 is a graph presenting a PSA assay performed along with the experimental protocol presented in FIG. 6.
Figure 17:
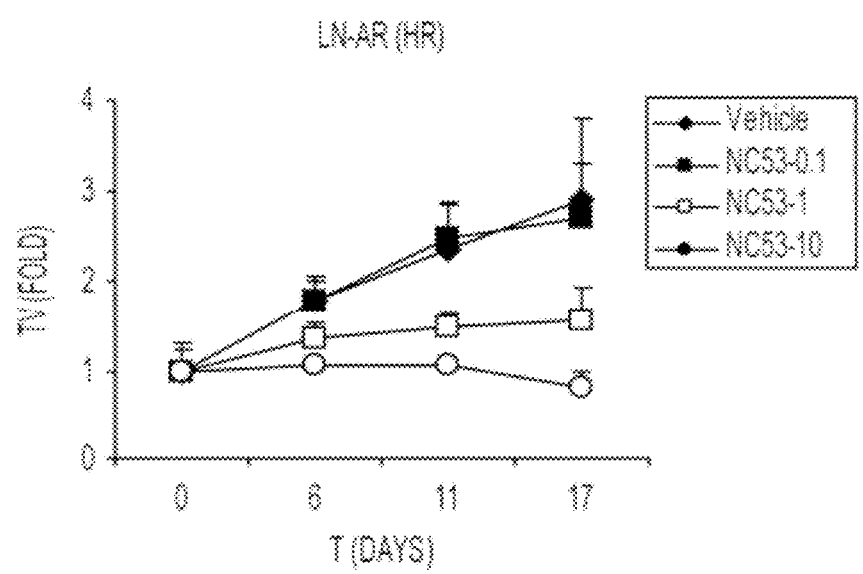
FIG. 17 is a graph presenting the effect of various dose regimens of NC53 on tumor volume.

FIG. 16 shows that under treatment with bicalutamide, PSA levels for LNCaP cells stayed the same or increased relative to treatment with vehicle solution, whereas under treatment with NC53, PSA levels decreased. FIG. 17 illustrates that under treatment with vehicle solution, tumors continued to increase in size. By contrast, under treatment with NC53 at a dose of 1 mg per kg body weight per day, the rate of tumor increase decreased, and the size of the tumor appeared to be stabilizing after about 17 days. Under treatment with NC53 at a dose of 10 mg per kg body weight per day, tumor size decreased with time.

Figure 18A:
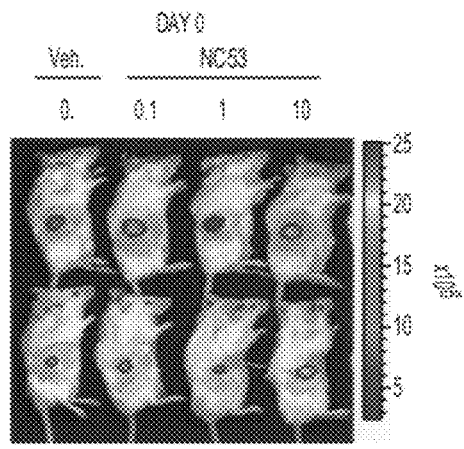
FIG. 18 is a graph presenting the rate of photon emission associated with luciferase activity at day 17 relative to the rate at day 0 after treatment with NC53 at doses of 0.1, 1, and 10 mg per kilogram body weight per day and without treatment with NC53.
Figure 18B:
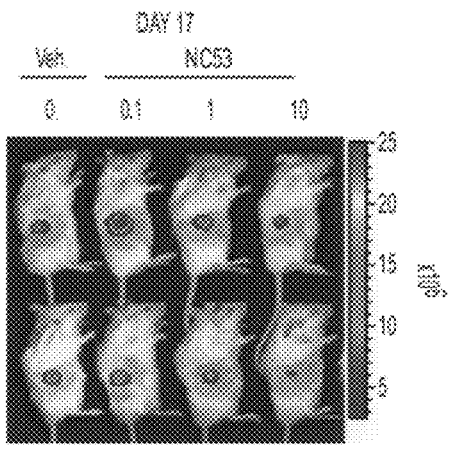
Figure 18C:
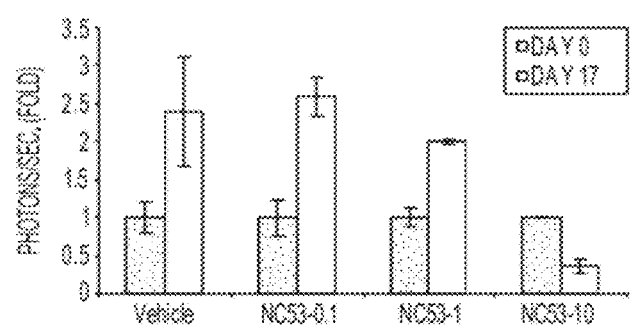
Figure 19A:
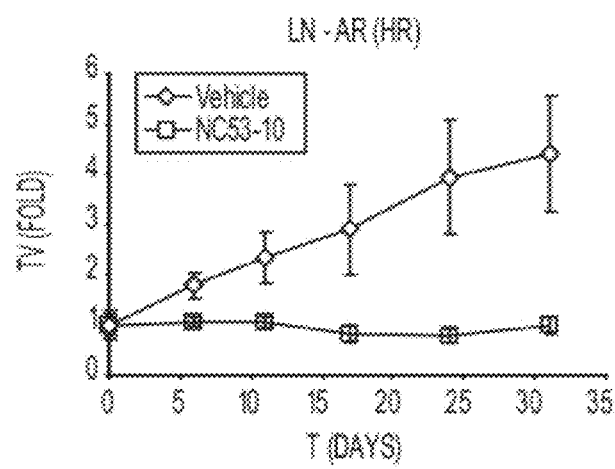
FIG. 19 presents the results of an experiment in which SCID mice were injected with the LN-AR(HR) cell line to induce tumor growth. One set of mice were treated with the compound NC53 at a dose of 10 mg per kilogram body weight per day; the other set of mice were treated only with vehicle solution. (A) The relative tumor volume as a function of time shown for each set of mice. (B) Images of each set of mice with photon emission associated with luciferase activity at day 31 shown as color contours. (C) Rate of photon emission associated with luciferase activity shown at several times for each set of mice.
Figure 19B:
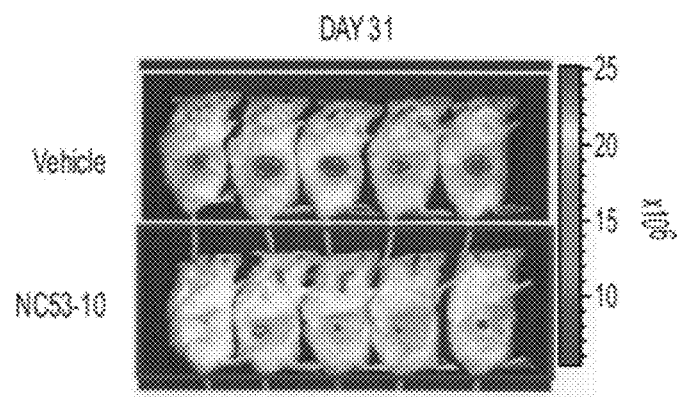
Figure 19C:
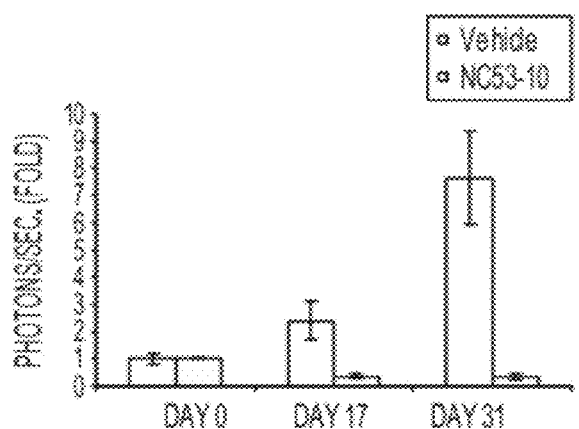

FIG. 18 illustrates that under treatment with NC53 at a dose of 10 mg per kg body weight per day, photon emission associated with luciferase activity decreased. FIG. 19 shows that treatment with NC53 at this dose resulted in a decrease or stabilization of tumor size and a decrease in photon emission associated with luciferase activity.

Figure 20A:
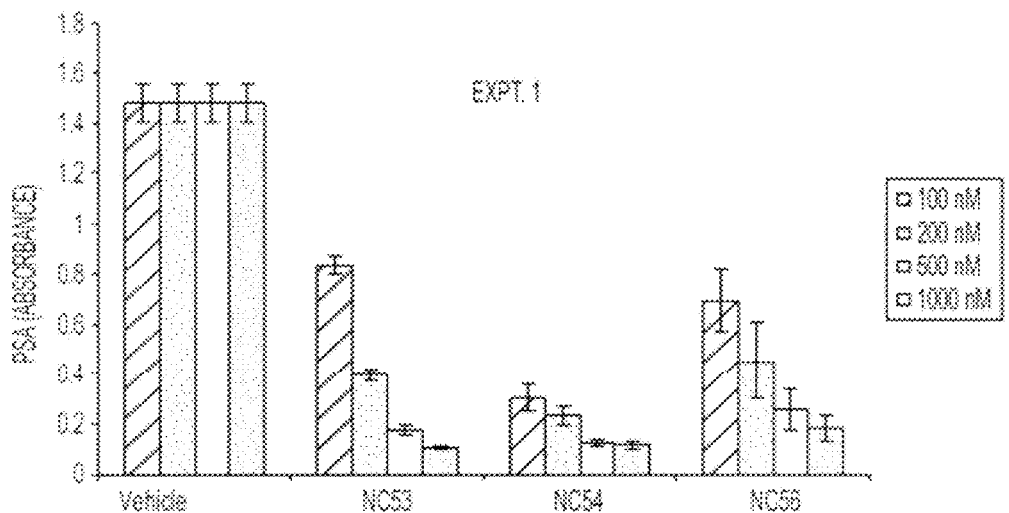
FIG. 20 is a graph presenting PSA absorbance associated with LN-AR cells treated with various concentrations of NC53, NC54, NC55, and NC57 and vehicle solution.
Figure 20B:
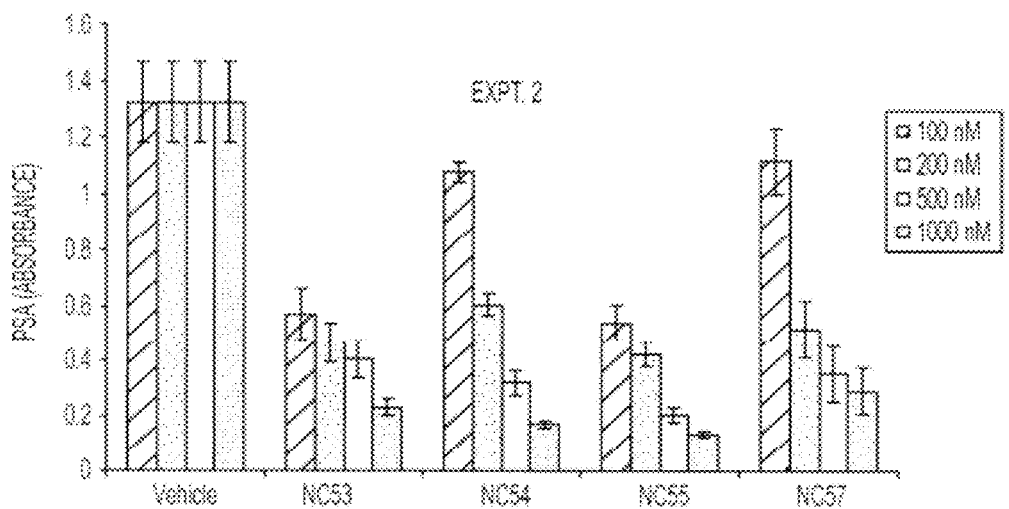
Figure 21:
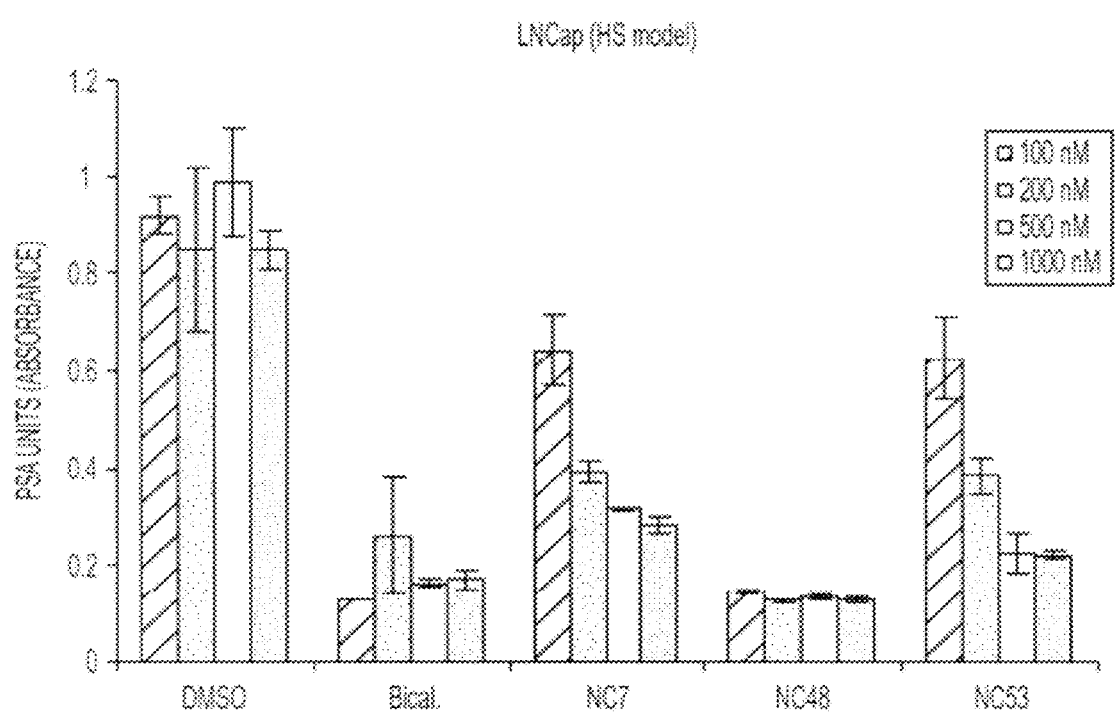
FIG. 21 is a graph presenting PSA absorbance associated with LN-CaP cells treated with various concentrations of NC7, NC48, NC53, bicalutamide, and DMSO.
Figure 22A:
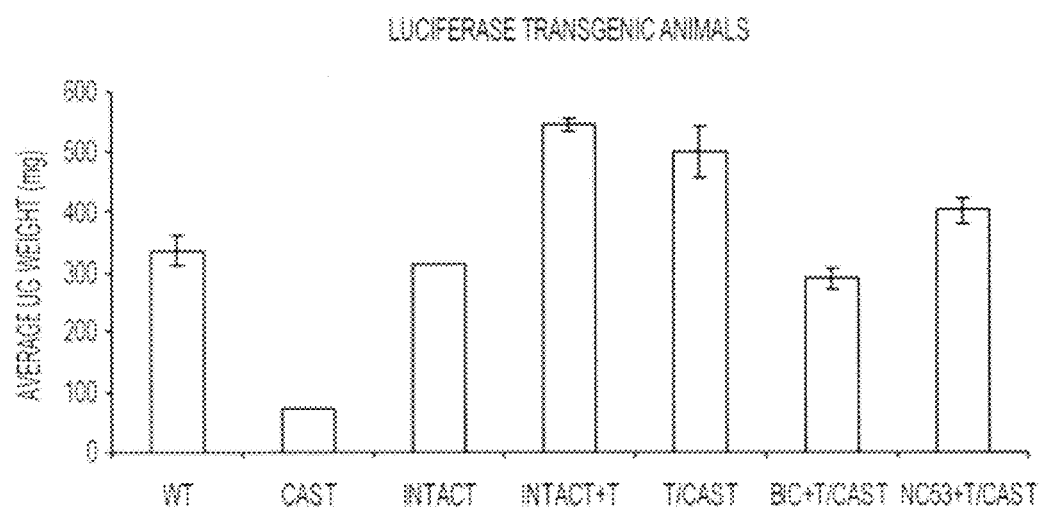
FIG. 22 presents results of an experiment conducted with wild type nontransgenic mice (WT), castrated luciferase transgenic mice (Cast), and non-castrated luciferase transgenic mice (Intact). Data are shown for castrated luciferase transgenic mice treated with an implanted testosterone pellet yielding 12.5 mg per kilogram body weight with a 90 day release period (T/Cast), and data are shown for non-castrated luciferase transgenic mice treated with an implanted testosterone pellet yielding 12.5 mg per kilogram body weight with a 90 day release period (Intact+T). Data are shown for castrated luciferase transgenic mice treated with the implanted testosterone pellet and with bicalutamide (BIC+T/Cast) or with NC53 (NC53+T/Cast) at 10 mg per kilogram body weight per day. (A) Urogenital tract weight at 14 days. (B) Photon emission rate at 14 days. In all cases, a hormone refractory disease state was not induced.
Figure 22B:
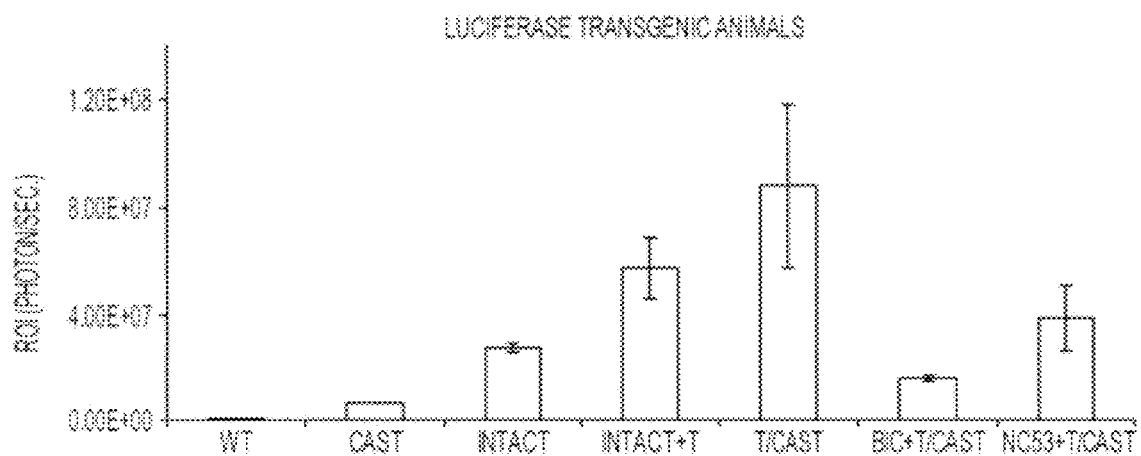

FIG. 20 shows that under treatment with NC53, NC54, NC55, NC56, and NC57 at doses of 100, 200, 500, and 1000 nM, PSA levels of LN-AR cells decreased. Moreover, the higher the dose, the lower the PSA level. FIG. 22 presents urogenital tract weight and rate of photon emission associated with luciferase activity initially and after 14 days of treatment with bicalutamide or with NC53 for intact and castrated mice. The weight and rate of photon emission increased for both intact and castrated mice. Treatment of castrated mice with NC53 resulted in a decrease in weight and photon emission with respect to the untreated castrated mice, as did treatment with bicalutamide.

Thus, Tier 1 compounds are particularly advantageous for use as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as glucocorticoid receptor, estrogen receptor, and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 5

TIER 1 COMPOUNDS

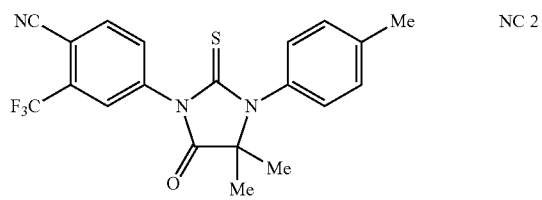

NC 2

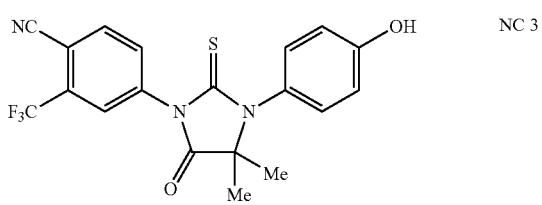

NC 3

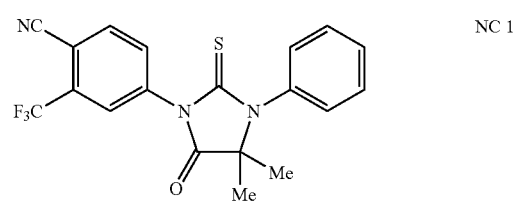

NC 1

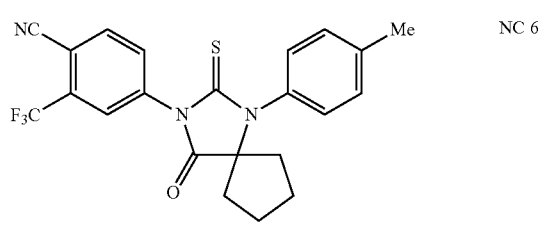

NC 6

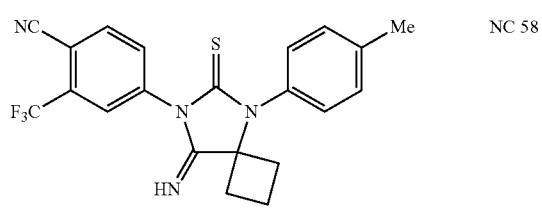

NC 58

TABLE 5-continued

TIER 1 COMPOUNDS

TABLE 5-continued

TIER 1 COMPOUNDS

NC 61, NC 62, NC 63, NC 64, NC 51, NC 41, NC 47, NC 48, NC 66, NC 67, NC 68, NC 69, NC 53

TABLE 5-continued

TIER 1 COMPOUNDS

NC 54

NC 55

NC 70

NC 56

NC 57

Tier 2

Figure 23:
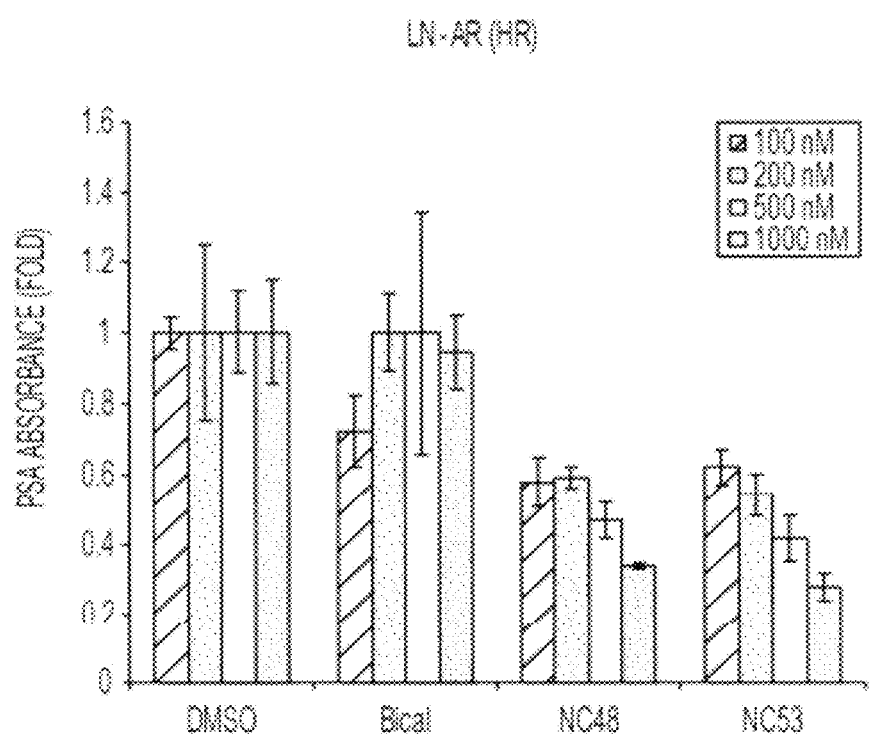
FIG. 23 is a graph depicting PSA absorbance measured for LN-AR cells after treatment with various doses of several compounds.
Figures 24A, 24B:
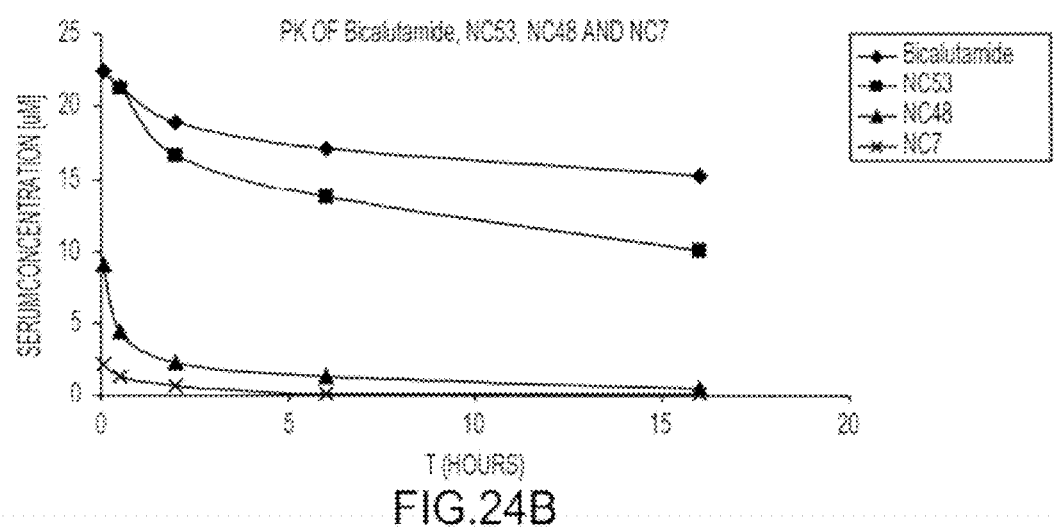
FIG. 24 presents a table providing several characteristics of compounds.

Tier 2 compounds (see Table 6) were significantly better than bicalutamide for treating prostate cancer, although there were indications that NC12 could act as an agonist. FIG. 3 illustrates that compounds NC66, NC67, NC68, NC53, and NC69 in Tier 1 and NC77 in Tier 2 dosed at concentrations ranging from 125 nM to 1000 nM acted to reduce luciferase activity in LNCaP-AR cells whereas control solutions of DMSO and of bicalutamide had little or no effect. It was found that at concentrations of 1000 nM, compounds NC7 and NC48, in Tier 1, caused a greater decrease in PSA level of LNCaP-AR cells than NC43, NC44, and NC50 in Tier 2. FIG. 7 presents tumor volume over time, and illustrates that under treatment with bicalutamide or vehicle solution, tumors continued to grow, whereas under treatment with NC53, in Tier 1, tumors decreased in size. FIG. 8 illustrates that photon emission associated with luciferase activity remained about the same or increased under treatment with bicalutamide relative to treatment with vehicle solution, whereas photon emission decreased under treatment with NC53. FIG. 23 illustrates that under treatment with bicalutamide, there was little or no decrease in PSA levels, whereas under treatment with NC48 and NC53, PSA levels decreased. FIG. 24 illustrates that the $IC_{50}$ for NC7, NC48, and NC53, in Tier 1, was much lower than the $IC_{50}$ for bicalutamide.

Generally, Tier 2 compounds are structurally similar to Tier 1 compounds, but with different substituents on the right hand aryl ring. Tier 2 compounds are advantageous for use as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 6

TIER 2 COMPOUNDS

NC 71

(comparative)

NC 5

NC 8

NC 9

TABLE 6-continued

TIER 2 COMPOUNDS

TABLE 6-continued

TIER 2 COMPOUNDS

NC 39, NC 43, NC 44, NC 50, NC 77 (chemical structures)

Tier 3

Tier 3 compounds (see Table 7) were judged to be slightly better than bicalutamide for treating prostate cancer. NC43, NC44, and NC50 (in Tier 2) caused a greater decrease in PSA level of LNCaP-AR cells than NC45 and NC49, in Tier 3. All of these compounds caused a greater decrease in PSA level than bicalutamide.

Other Tier 3 compounds (not shown) were not diarylthiohydantoins, and were comparable in activity to prior art monoarylhydantoin compounds NC83, NC79, and NC80.

Thus, Tier 3 compounds are useful as AR antagonists, and as therapeutic agents for hormone refractory prostate cancer. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 7

TIER 3 COMPOUNDS

NC 78 (comparative)

NC 79 (comparative)

NC 80 (comparative)

NC 81

NC 82

NC 42

(chemical structures)

TABLE 7-continued

TIER 3 COMPOUNDS

[Structure NC 46: 4-cyano-3-trifluoromethylphenyl thiohydantoin with spirocyclobutyl and aryl-propyl-methyl ester substituent]

[Structure NC 45: 4-cyano-3-trifluoromethylphenyl thiohydantoin with spirocyclobutyl and aryl-propanamide-ethanol substituent]

[Structure NC 49: 4-cyano-3-trifluoromethylphenyl thiohydantoin with spirocyclobutyl and aryl-piperazine substituent]

Tier 4

Tier 4 compounds (see Table 8) were judged to be no better than bicalutamide for treating prostate cancer. Tier 4 NC93 and NC94 and Tier 1 NC7, for example, differ only in the substituent on the lower right carbon of the hydantoin ring. The substituents on the right hand aryl ring may also affect activity.

Some Tier 4 compounds (including those shown and others that are not shown) were not diaryl compounds (lacking the right hand aryl ring), were not thiohydantoins, were not disubstituted on the carbon on the lower right hand of the hydantoin ring, and/or had substituents other than oxygen or amido on the lower left hand carbon of the hydantoin ring. This provides evidence of the surprising advantages of diarylthiohydantoins that are disubstituted on the lower right hand carbon of the hydantoin ring and have oxygen or amido on the lower left hand carbon of the hydantoin ring.

Thus, Tier 4 compounds may be useful as AR antagonists, and as therapeutic agents for hormone refractory prostate cancer, at least to the extent that they are comparable to bicalutamide. They may be useful to treat other AR related diseases or conditions such as benign prostate hyperplasia, hair loss, and acne. These and related compounds may also be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 8

TIER 4 COMPOUNDS

[Structure NC 83: 4-cyano-3-trifluoromethylphenyl dimethyl thiohydantoin with propyl azide substituent] (comparative)

[Structure NC 4: 4-cyano-3-trifluoromethylphenyl dimethyl thiohydantoin with 4-aminophenyl substituent]

[Structure NC 34: 4-cyano-3-trifluoromethylphenyl thiohydantoin with 4-methylphenyl substituent]

[Structure NC 85: 4-cyano-3-trifluoromethylphenyl thiohydantoin with 4-methylphenyl and methyl substituent]

[Structure NC 86: 4-cyano-3-trifluoromethylphenyl thiohydantoin with 4-methylphenyl and ethyl substituent]

[Structure NC 87: 4-cyano-3-trifluoromethylphenyl thiohydantoin with 4-methylphenyl and propyl substituent]

[Structure NC 88: 4-cyano-3-trifluoromethylphenyl thiohydantoin with 4-methoxyphenyl substituent]

TABLE 8-continued
TIER 4 COMPOUNDS
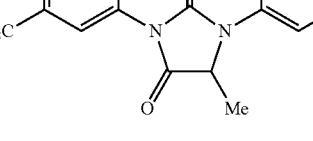

TABLE 8-continued

TIER 4 COMPOUNDS

[Structure NC 97]
[Structure NC 98]
[Structure NC 99]
[Structure NC 100]

Tier 5

Tier 5 compounds (see Table 9) were inactive or nearly inactive, and thus, were worse than bicalutamide for treating prostate cancer. The substituents on the right hand aryl ring are important to determining activity.

Some Tier 5 compounds (some of which are shown and some that are not shown) were not diaryl compounds (lacking the right hand aryl ring), were not thiohydantoins, were not disubstituted on the carbon on the lower right hand of the hydantoin ring, and/or had substituents other than oxygen or amido on the lower left hand carbon of the hydantoin ring. This provides evidence of the surprising advantages of diarylthiohydantoins that are disubstituted on the lower right hand carbon of the hydantoin ring and have oxygen or amido on the lower left hand carbon of the hydantoin ring. In particular, the terminal substituent in NC103, NC104, and NC106 ($CH_2NR_xR_y$, where $R_{x,y}$=H or methyl) is not seen as contributing to activity in these compounds.

Tier 5 compounds would not be desirable for treatment of prostate cancer or as AR antagonists, although these and related compounds may be useful as modulators of other nuclear receptors, such as estrogen receptor and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays e.g. as standards, or as intermediates or prodrugs.

TABLE 9

TIER 5 COMPOUNDS

[Structure NC 101]
[Structure NC 102]
[Structure NC 19]
[Structure NC 31]
[Structure NC 32]
[Structure NC 103]
[Structure NC 104]
[Structure NC 105]

TABLE 9-continued

TIER 5 COMPOUNDS

NC 106

Tier 6

Tier 6 compounds (see Table 10) were inactive or nearly inactive, and furthermore were strong agonists, and thus were much worse than bicalutamide for treating prostate cancer. The comparative compounds ranked very poor relative to the inventive compounds. Notably, NC107 had very poor activity, with a chlorine substituent on the left hand aryl ring, whereas NC2, with a trifluoromethane, and NC63, with iodine, ranked in Tier 1. The results for the Tier 6 compounds provide evidence of the surprising advantages of diarylthiohydantoins that are disubstituted on the lower right hand carbon of the hydantoin ring and have oxygen or amido on the lower left hand carbon of the hydantoin ring, and have certain substituents on the left hand aryl ring.

Tier 6 compounds would not be desirable for treatment of prostate cancer or as AR antagonists.

TABLE 10

TIER 6 COMPOUNDS

NC 107

NC 24 (comparative)

NC 25 (comparative)

TABLE 10-continued

TIER 6 COMPOUNDS

NC 26

NC 27 (comparative)

NC 28

Untiered Compounds

For several compounds, there was insufficient experimental data to rank them. These untiered compounds are presented in Table 11.

Based on the data and methods of the invention, and applying judgment based on review of many compounds, including some not shown here, one can make some observations about the untiered compounds. Comparative example NC108 is expected to be in Tier 3 with comparative examples NC78-NC80. NC113 is expected to hydrolyze to NC7 (Tier 1), and should therefore have comparable activity. NC114 is expected to hydrolyze to NC16 (Tier 1), and should therefore have comparable activity. NC115 is expected to hydrolyze to NC3 (Tier 1), and NC120 and NC121 are expected to hydrolyze to NC50 (Tier 2), and they should therefore have comparable activity.

TABLE 11

UNTIERED COMPOUNDS

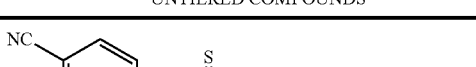

NC 108 (comparative)

TABLE 11-continued

UNTIERED COMPOUNDS

NC 109, NC 10, NC 110, NC 111, NC 112, NC 113, NC 114, NC 115, NC 116, NC 117, NC 118, NC 119, NC 120

TABLE 11-continued

UNTIERED COMPOUNDS

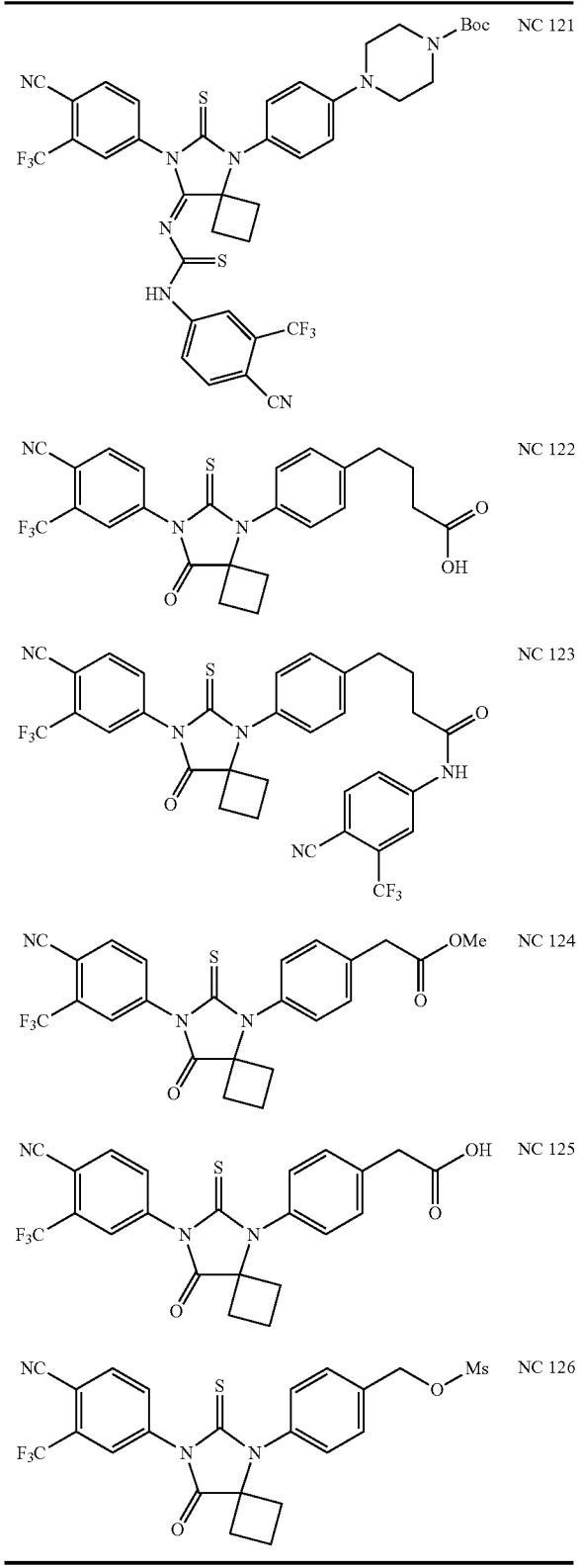

In short, novel compounds which show evidence of being far superior to bicalutamide in treating prostate cancer were identified and produced.

Sensitivity of Anti-Cancer Activity of Compounds to Structural Differences

Figure 25:
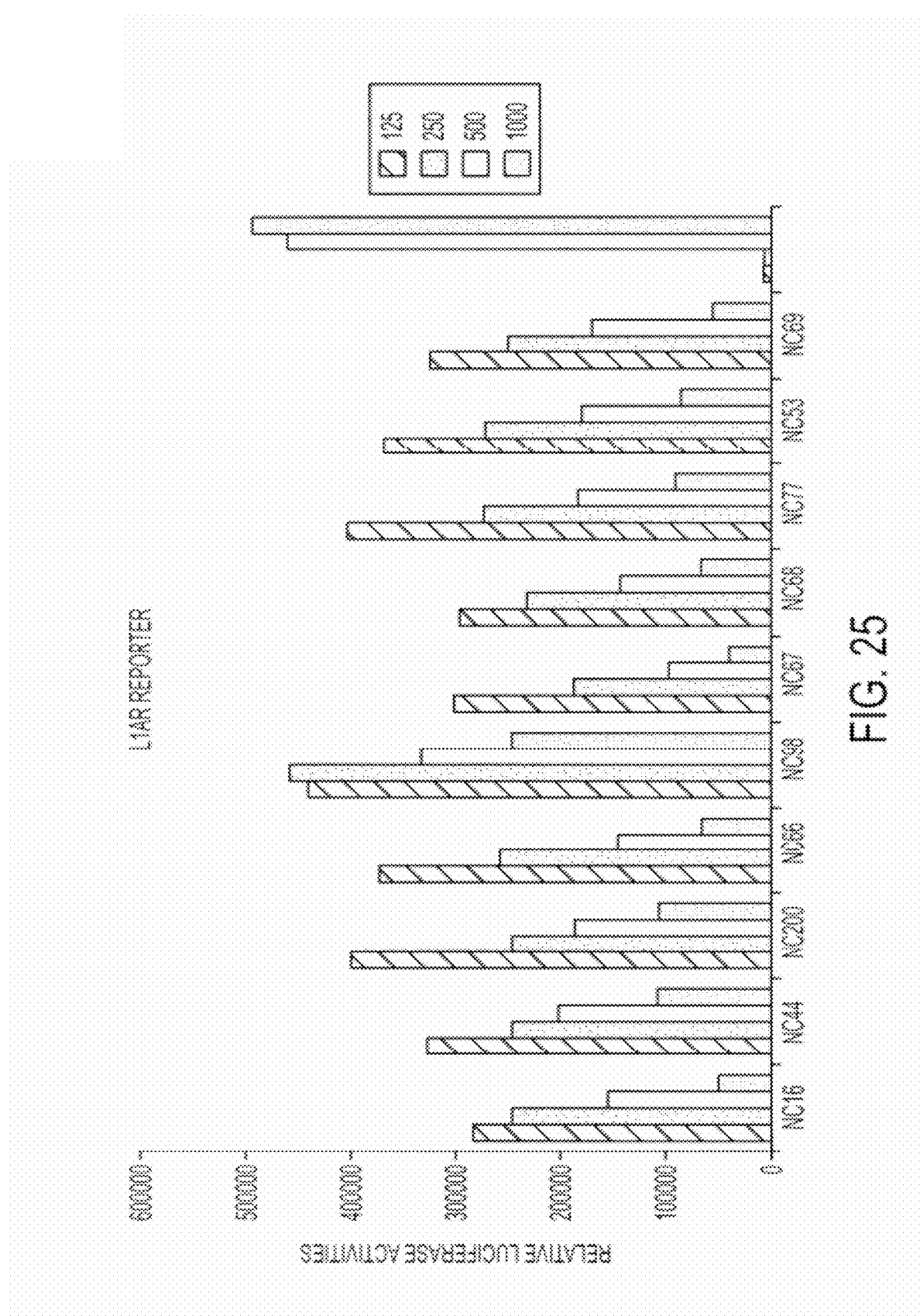
FIG. 25 is a graph of luciferase activity of the LIAR cell line dosed with various compounds administered at concentrations ranging from 125 nmol to 1000 nmol.

The inventors have determined that what might appear to be a small change in the structure of hydantoin compounds may result in a large change in that compound's performance in treating prostate cancer. For example, NC77 and NC53 differ only by a single fluorine substituent on an aryl ring, and NC53 is in Tier 1, while NC77 is in Tier 2, both being better than bicalutamide for the treatment of prostate cancer, but NC53 being superior. However, NC98, which differs from NC77 only in having an additional carbon atom between the methylcarbamoyl group and the aryl ring, is no better than bicalutamide for the treatment of prostate cancer and is ranked in Tier 4. The effect of NC77, NC53, and NC98 on luciferase activity can be seen in FIG. 25. At a given concentration of compound, the luciferase activity upon exposure to NC77 and NC53 is less than the luciferase activity upon exposure to NC98.

NC4 differs from NC3 only in that an amino group is substituted for a hydroxyl group. However, whereas NC3 is in Tier 1, much better than bicalutamide for the treatment of prostate cancer, NC4 is in Tier 4, no better than bicalutamide. The effect of NC3 and NC4 on luciferase activity in the 1AR cell line was studied by administering various compounds at concentrations ranging from 1.25 to 10 μmol and observing PSA levels. For a given dose, the luciferase activity upon exposure to NC3 is less than the luciferase activity upon exposure to NC4. The effect of NC3 and NC4 on luciferase activity in the 4AR cell line was studied by administering various compounds at concentrations ranging from 1.25 to 10 μmol and observing luciferase activity. For a given dose, the luciferase activity upon exposure to NC3 is less than the luciferase activity upon exposure to NC4. The effect of NC3 and NC4 on PSA levels in the LN/AR cell line was studied by administering various compounds at concentrations ranging from 1.25 to 10 μmol and observing luciferase activity. For a given dose, the PSA level upon exposure to NC3 is less than the PSA level upon exposure to NC4.

NC47 and NC48 differ from each other only by a methyl substituent on the end of a carbamoyl group and both compounds are ranked in Tier 1, although NC48 has been found to be particularly advantageous. NC46 is the same as NC47, with the exception of a methoxy group being substituted for an amino group. However, NC46 is ranked in Tier 3. NC42 is similar to NC46, but has one less carbon in the chain linking the ester group to the aryl ring; NC42 is ranked in Tier 3. The effect of NC47, NC48, NC42, and NC46 on PSA levels in the LN/AR cell line was studied by administering various compounds at concentrations ranging from 125 nmol to 1000 nmol and observing PSA levels. For a given concentration, the PSA level upon exposure to NC47 and NC48 is less than the PSA level upon exposure to NC42 and NC46.

NC68 and NC103 differ from each other in that the former has a methylcarbamoyl group attached to an aryl ring and a dimethyl substituent attached to the thiohydantoin group, whereas the latter has a methylamino group attached to the right hand aryl ring and a cyclobutyl substituent attached to the thiohydantoin group. Whereas NC68 is in Tier 1, much better than bicalutamide for the treatment of prostate cancer, NC103 is in Tier 5, inactive or nearly inactive in the treatment of prostate cancer. The effect of NC68 and NC103 on luciferase activity in the LN/AR cell line was studied by administering various compounds at concentrations ranging from 125 nmol to 1000 nmol and observing luciferase activity. For a given concentration, the luciferase activity upon exposure to NC68 is less than the luciferase activity upon exposure to NC103.

NC16 and NC18 differ from each other in the substitution of a thio for an oxo group and a dimethyl substituent for a cyclobutyl substituent. Whereas NC16 is in Tier 1, NC18 is in Tier 4.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The diarylhydantoin compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, diarylhydantoin compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the diarylhydantoin compounds may be combined with one or more excipients and used in the form of ingestible tablets, buccal tablets, troches, capsules, elixirs, suspensions, syrups, wafers, and the like. The diarylhydantoin compounds may be combined with a fine inert powdered carrier and inhaled by the subject or insufflated. Such compositions and preparations should contain at least 0.1% diarylhydantoin compounds. The percentage of the compositions and preparations may, of course, be varied and may conveniently be between about 2% to about 60% of the weight of a given unit dosage form. The amount of diarylhydantoin compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the diarylhydantoin compounds may be incorporated into sustained-release preparations and devices. For example, the diarylhydantoin compounds may be incorporated into time release capsules, time release tablets, and time release pills.

The diarylhydantoin compounds may also be administered intravenously or intraperitoneally by infusion or injection. Solutions of the diarylhydantoin compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the diarylhydantoin compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the diarylhydantoin compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the diarylhydantoin compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the diarylhydantoin compounds can be dissolved or dispersed at effective levels, optionally with the aid of nontoxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the diarylhydantoin compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the diarylhydantoin compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the diarylhydantoin compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The diarylhydantoin compounds are conveniently administered in unit dosage form; for example, containing 0.05 to 10000 mg, 0.5 to 10000 mg, 5 to 1000 mg, or about 100 mg of active ingredient per unit dosage form.

The diarylhydantoin compounds can be administered to achieve peak plasma concentrations of, for example, from about 0.5 to about 75 µM, about 1 to 50 µM, about 2 to about 30 or about 5 to about 25 Exemplary desirable plasma concentrations include at least or no more than 0.25, 0.5, 1, 5, 10, 25, 50, 75, 100 or 200 For example, plasma levels may be from about 1 to 100 micromolar or from about 10 to about 25 micromolar. This may be achieved, for example, by the intravenous injection of a 0.05 to 5% solution of the diarylhydantoin compounds, optionally in saline, or orally administered as a bolus containing about 1-100 mg of the diarylhydantoin compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the diarylhydantoin compounds per kg of body weight.

The diarylhydantoin compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

A number of the above-identified compounds exhibit little or no agonistic activities with respect to hormone refractory prostate cancer cells. Because these compounds are strong AR inhibitors, they can be used not only in treating prostate cancer, but also in treating other AR related diseases or conditions such as benign prostate hyperplasia, hair loss, and acne. Because AR belongs to the family of nuclear receptors, these compounds may serve as scaffolds for drug synthesis targeting other nuclear receptors, such as estrogen receptor and peroxisome proliferator-activated receptor. Therefore, they may be further developed for other diseases such as breast cancer, ovarian cancer, diabetes, cardiac diseases, and metabolism related diseases, in which nuclear receptors play a role.

A sequence for the chemical synthesis of several compounds according to the invention is shown below. The cyanohydrins 10abc are converted into the four different cyanoamines 12abcd by reaction with the three different anilines 11abc (10a and 11a give 12a, 10b and 11a give 12b, 10c and 11b give 12c, and 10c and 11c give 12d). In a separate process the aniline 13 is converted in one step into the isothiocyanate 14. Addition of 12abcd to 14 followed by treatment with mild acid produces the desired thiohydantoins 4 (NC54), 5 (NC55), 6 (NC56), and 7 in good yield.

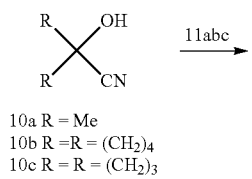

10a R = Me
10b R = R = (CH$_2$)$_4$
10c R = R = (CH$_2$)$_3$

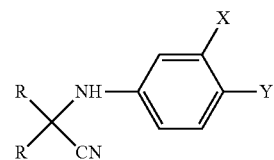

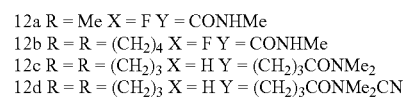

12a R = Me X = F Y = CONHMe
12b R = R = (CH$_2$)$_4$ X = F Y = CONHMe
12c R = R = (CH$_2$)$_3$ X = H Y = (CH$_2$)$_3$CONMe$_2$
12d R = R = (CH$_2$)$_3$ X = H Y = (CH$_2$)$_3$CONMe$_2$CN

-continued

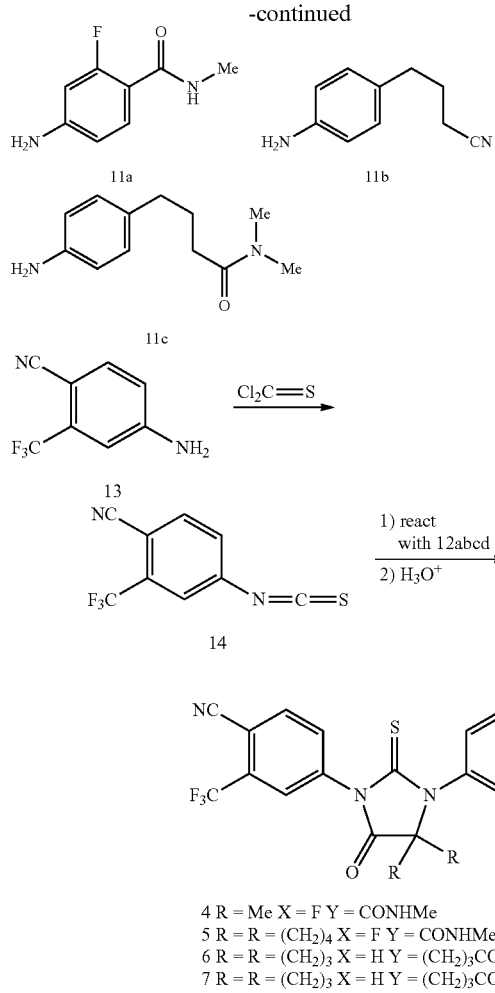

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A compound having the formula

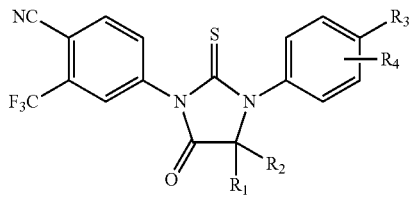

and pharmaceutically acceptable salts thereof,
wherein $R_1$ and $R_2$ are independently methyl or, together with the carbon to which they are linked, a cycloalkyl group of 4 to 5 carbon atoms,
wherein $R_3$ is selected from the group consisting of cyanoalkyl and dialkylcarbamoylalkyl, and
wherein $R_4$ is hydrogen or fluorine.

2. A pharmaceutical composition comprising a therapeutically effective amount of a compound according to claim 1 or a pharmaceutically acceptable salt thereof, and a pharmaceutically acceptable carrier or diluent.

3. The compound of claim 1, having the formula

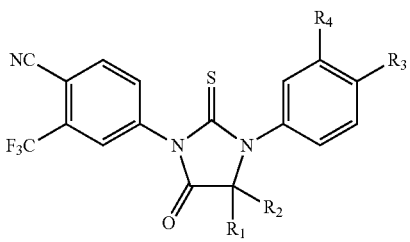

wherein R3 is dialkylcarbamoylalkyl and
wherein R3 is not dimethylcarbamoylalkyl.

4. A pharmaceutical composition comprising a therapeutically effective amount of a compound according to claim 3 or a pharmaceutically acceptable salt thereof, and a pharmaceutically acceptable carrier or diluent.

5. The pharmaceutical composition of claim 2, having a form selected from the group consisting of a solution, dispersion, suspension, powder, capsule, tablet, pill, time release capsule, time release tablet, and time release pill.

6. A method for treating a cancer, comprising administering a therapeutically effective amount of a compound according to claim 1 or a pharmaceutically acceptable salt thereof to a subject in need of such treatment, thereby treating the cancer.

7. The method of claim 6, wherein the composition is administered at a dosage of the compound in the range of from about 0.001 mg per kg body weight per day to about 100 mg per kg body weight per day.

8. The method of claim 6, wherein the composition is administered at a dosage of the compound in the range of from about 0.01 mg per kg body weight per day to about 100 mg per kg body weight per day.

9. The method of claim 6, wherein the composition is administered at a dosage of the compound in the range of from about 0.1 mg per kg body weight per day to about 10 mg per kg body weight per day.

10. The method of claim 6, wherein the composition is administered at a dosage of the compound of about 1 mg per kg body weight per day.

11. A method comprising contacting a mammalian cell capable of expressing prostate specific antigen with a sufficient amount of a compound according to claim 1 to interfere with the transcription of prostate specific antigen mRNA.

12. A method, comprising contacting a mammalian cell with a sufficient amount of a compound according to claim 1 to prevent formation of a transcription complex on a prostate specific antigen gene.

13. A method, comprising contacting a mammalian cell with a sufficient amount of a compound according to claim 1 to prevent an androgen receptor protein from complexing with a prostate specific antigen gene.

14. A method, comprising contacting a mammalian cell with a sufficient amount of a compound according to claim 1 to prevent an RNA polymerase II from complexing with a prostate specific antigen gene.

15. A method, comprising contacting a mammalian cell with a sufficient amount of a compound according to claim 1 to prevent nuclear translocation of an androgen receptor protein and/or to destabilize an androgen receptor protein.

16. The method of claim 6, wherein the compound is administered by intravenous injection, by injection into tissue, intraperitoneally, orally, or nasally.

17. The method of claim 6, wherein the cancer is selected from the group consisting of a metastatic cancer, a hormone refractory cancer, prostate cancer, hormone refractory prostate cancer, hormone sensitive prostate cancer, breast cancer, hormone refractory breast cancer, and ovarian cancer.

18. The method of claim 6, further comprising administering a hormone therapy to the subject before the therapeutically effective amount of the compound is administered.

19. A method for treating a cancer, comprising administering a therapeutically effective amount of a compound having the formula

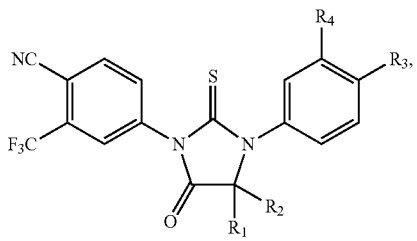

or a pharmaceutically acceptable salt thereof to a subject in need of such treatment, thereby treating the cancer,
wherein $R_1$ and $R_2$ are independently methyl or, together with the carbon to which they are linked, a cycloalkyl group of 4 to 5 carbon atoms,
wherein $R_3$ is selected from the group consisting of dimethylcarbamoylalkyl and cyanoalkyl, and
wherein $R_4$ is hydrogen or fluorine.

20. The method of claim 19, wherein the cancer is a metastatic cancer.

21. The method of claim 19, wherein the cancer is a hormone refractory cancer.

22. The method of claim 19, wherein the cancer is hormone refractory breast cancer.

23. The method of claim 22, wherein the compound is

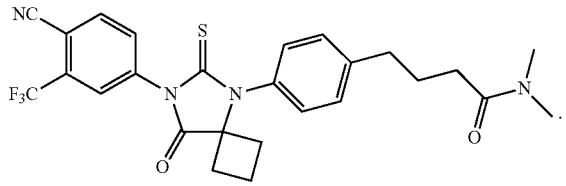

[NC56]

24. The method of claim 22, wherein the compound is

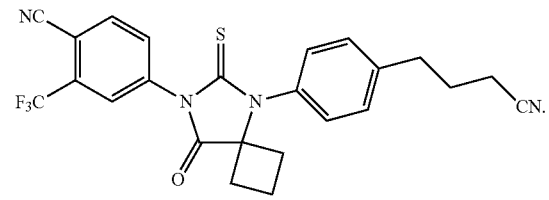

[NC57]

25. The method of claim 19, further comprising administering a hormone therapy to the subject.

26. The method of claim 25, wherein the hormone therapy is administered prior to the therapeutically effective amount of the compound being administered.

27. The method of claim 25,
wherein the cancer is prostate cancer,
wherein the hormone therapy is administered prior to the therapeutically effective amount of the compound being administered, and
wherein the hormone therapy comprises the administration of bicalutamide.

* * * * *